(12) United States Patent
Maisano et al.

(10) Patent No.: US 11,370,826 B2
(45) Date of Patent: Jun. 28, 2022

(54) RECOMBINANT CHIMERIC PROTEIN FOR SELECTINS TARGETING

(71) Applicant: Bracco Suisse SA, Manno (CH)

(72) Inventors: Federico Maisano, Lodi (IT); Federico Crivellin, Caselle Torinese (IT); Thierry Bettinger, Peillonnex (FR); Philippe Bussat, Pers-Jussy (FR); Samir Cherkaoui, Feigeres (FR); Christian Koller, Geneva (CH); Adrian Lobito, Belmont, CA (US)

(73) Assignee: Bracco Suisse SA, Manno (CH)

( * ) Notice: Subject to any disclaimer, the term of this patent is extended or adjusted under 35 U.S.C. 154(b) by 525 days.

(21) Appl. No.: 16/076,664

(22) PCT Filed: Feb. 9, 2017

(86) PCT No.: PCT/EP2017/052821
§ 371 (c)(1),
(2) Date: Aug. 8, 2018

(87) PCT Pub. No.: WO2017/137477
PCT Pub. Date: Aug. 17, 2017

(65) Prior Publication Data
US 2019/0048062 A1 Feb. 14, 2019

(30) Foreign Application Priority Data
Feb. 9, 2016 (EP) .................................... 16154868

(51) Int. Cl.
| | | |
|---|---|---|
| C07K 14/705 | (2006.01) |
| A61K 49/00 | (2006.01) |
| A61K 49/22 | (2006.01) |
| A61K 49/08 | (2006.01) |
| C12N 9/10 | (2006.01) |
| A61K 38/00 | (2006.01) |

(52) U.S. Cl.
CPC .... *C07K 14/70564* (2013.01); *A61K 49/0032* (2013.01); *A61K 49/0056* (2013.01); *A61K 49/0084* (2013.01); *A61K 49/085* (2013.01); *A61K 49/221* (2013.01); *A61K 49/223* (2013.01); *C07K 14/705* (2013.01); *C12N 9/1051* (2013.01); *A61K 38/00* (2013.01); *C12Y 204/01039* (2013.01); *C12Y 204/01068* (2013.01); *G01N 2333/70564* (2013.01)

(58) Field of Classification Search
None
See application file for complete search history.

(56) References Cited

U.S. PATENT DOCUMENTS

| | | |
|---|---|---|
| 4,276,885 A | 7/1981 | Tickner et al. |
| 5,021,556 A | 6/1991 | Srinivasan |
| 5,075,099 A | 12/1991 | Srinivasan et al. |
| 5,118,797 A | 6/1992 | Jurisson et al. |
| 5,183,653 A | 2/1993 | Linder et al. |
| 5,271,928 A | 12/1993 | Schneider et al. |
| 5,362,476 A | 11/1994 | Sherry et al. |
| 5,364,613 A | 11/1994 | Sieving et al. |
| 5,367,080 A | 11/1994 | Toner et al. |
| 5,387,409 A | 2/1995 | Nunn et al. |
| 5,409,689 A | 4/1995 | Winchell et al. |
| 5,413,774 A | 5/1995 | Schneider et al. |
| 5,445,813 A | 8/1995 | Schneider et al. |
| 5,556,610 A | 9/1996 | Yan et al. |
| 5,574,140 A | 11/1996 | Pollack et al. |
| 5,597,549 A | 1/1997 | Schneider et al. |
| 5,608,110 A | 3/1997 | Ramalingam et al. |
| 5,627,286 A | 5/1997 | Ramalingam et al. |
| 5,656,254 A | 8/1997 | Ramalingam et al. |
| 5,659,041 A | 8/1997 | Pollak et al. |
| 5,662,885 A | 9/1997 | Pollak et al. |
| 5,665,329 A | 9/1997 | Ramalingam et al. |

(Continued)

FOREIGN PATENT DOCUMENTS

| | | |
|---|---|---|
| EP | 3324938 A1 | 7/1989 |
| EP | 0554213 A1 | 8/1993 |

(Continued)

OTHER PUBLICATIONS

Chichili et al. (2013) Protein Science 22: 153-167.*
McEvers et al. (1997) J. Clin. Invest. 100:485-492 (Year: 2007).*
Anelli et al. "L-Glutamatic acid and L-Lysine as useful building blocks for the preparation of bifunctional DTPA-like ligands," Bioconj. Chern. 10:137-140 (1999).
Benet, L. et al. "Pharmacokinetics: the dynamics of drug absorption, distribution, and elimination," In: Goodman & Gilman's The Pharmacological Basis of Therapeutics, 9th ed. pp 3-27 (1996).
Chou, et al. "Quantification of interleukin-6 in cell culture medium using surface plasmon resonance biosensors," Cytokine, 51:107-111 (2010).
Cummings, RD, "Structure and function of the selectin ligand PSGL-1," Brazilian Journal of Medical and Biological research, 32:519-528 (1999).

(Continued)

*Primary Examiner* — Michael D Pak
(74) *Attorney, Agent, or Firm* — Vivicar Law, PLLC

(57) ABSTRACT

The invention discloses a recombinant protein (P-selectin glycoprotein ligand-1 and Neural Retina-specific Leucine Zipper) PSGL-1-NRL chimeric protein comprising a Selectin Binding domain and a non-covalent dimerization domain, which is a leucine zipper and is more preferably the leucine zipper domain of the human or mouse Neural Retina-specific Leucine Zipper. The chimeric protein further comprises a covalent dimerization domain with at least one cysteine suitable to form a disulfide bridge with another chimeric protein to form a homodimer. In the chimeric protein, the PSGL-1 domain corresponds to the extracellular region of Human PSGL-1 and is more preferably the selectin binding region of the mature protein. The chimeric protein is correctly post-translationally modified and is efficiently expressed in a mammalian system. It is sulfated, O-linked glycosylated and sialylated and binds P, E and L selectin, allowing in vivo and in vitro targeting for diagnostic or therapeutic purposes.

10 Claims, 5 Drawing Sheets

Specification includes a Sequence Listing.

(56) References Cited

U.S. PATENT DOCUMENTS

| | | | |
|---|---|---|---|
| 5,688,487 A | 11/1997 | Linder et al. | |
| 5,711,933 A | 1/1998 | Bichon et al. | |
| 5,720,934 A | 2/1998 | Dean et al. | |
| 5,780,006 A | 7/1998 | Pollak et al. | |
| 5,827,504 A | 10/1998 | Yan et al. | |
| 5,827,817 A | 10/1998 | Larsen et al. | |
| 5,886,142 A | 3/1999 | Thakur et al. | |
| 5,976,495 A | 11/1999 | Pollak et al. | |
| 6,093,382 A | 7/2000 | Wedeking et al. | |
| 6,143,274 A | 11/2000 | Tweedie et al. | |
| 6,277,975 B1 | 8/2001 | Larsen et al. | |
| 6,333,021 B1 | 12/2001 | Schneider et al. | |
| 6,509,324 B1 | 1/2003 | Franzini et al. | |
| 2003/0166521 A1* | 9/2003 | Eppihimer | C07K 14/70596 424/141.1 |
| 2010/0196284 A1* | 8/2010 | Lindner | A61K 9/0019 424/9.52 |
| 2015/0017169 A1* | 1/2015 | Humphreys | A61P 1/04 424/136.1 |

FOREIGN PATENT DOCUMENTS

| | | |
|---|---|---|
| WO | 9409829 A1 | 5/1994 |
| WO | 2001046207 A1 | 6/2001 |
| WO | 03008394 A1 | 1/2003 |
| WO | 2003008390 A1 | 1/2003 |
| WO | 2004069284 A2 | 8/2004 |
| WO | 2005062828 A2 | 7/2005 |
| WO | 2005105840 A2 | 11/2005 |
| WO | 2008071679 A1 | 6/2008 |
| WO | 2008131217 A1 | 10/2008 |
| WO | 2012020030 A1 | 2/2012 |
| WO | 2013135750 A1 | 9/2013 |
| WO | 2014191467 A1 | 12/2014 |

OTHER PUBLICATIONS

De Kruif, et al., "Leucine zipper dimerized bivalent and bispecific scFv antibodies from a semi-synthetic antibody phage display library," J. Biol. Chem. 271:7630-7634 (1996).

Eisenwiener et al. "A convenient synthesis of novel bifunctional prochelators for coupling to bioactive peptides for radiometal labelling," Bioorg Med Chem Lett. 10: 2133-2135 (2000).

Gibbs, S.L., "Near infrared fluorescence for image-guided surgery," Quant Imaging Med Surg. 2(3):177-187 (2012).

Hermann et al., "Gadolinium (III) complexes as MRI contrast agents: ligand design and properties of the complexes," Dalton Trans., 23:3027-3047 (2008).

Hermanson, Greg T. "Functional Targets," In: Bioconjugate Techniques, 2nd ed. pp. 3-168 (2008).

Lattuada, L. et al. "The synthesis and application of polyamino polycaboxylic bifunctional chelating agents," Chem Soc. Rev. 40:3019-3049 (2011).

Lee, et al. "Bivalent antibody phage display mimics natural immunoglobulin," J. Immunological Methods, 284: 119-132 (2004).

Li et al., "Post-translational modifications of recombinant P-selectin glycoprotein Ligand-1 required for binding to P- anti E-selectin," J. Biol. Chem. 271:3255-3264 (1996).

Lifescience (ThermoFisher Scientific), Freedom™ CHO-S™ Kit User Guide, Publication No. MAN0003505, pp. 1-69 (2015).

Liu et al. "99mTc-labeled small peptides as diagnostic radiopharmaceuticals," Chem Rev, 99:2235-2268 (1999).

Liu et al., "Identification of N-terminal residues on P-selectin glycoprotein ligand-1 required for binding to P-selectin," J Biol. Chem. 273:7078-7087 (1998).

Liu, S. et al. "Bifunctional chelators for therapeutic lanthanide radiopharmaceuticals," Bioconjugate Chem. 12: 7-34 (2001).

PCT Search Report and Written Opinion for PCT/EP2017/052821, dated date Apr. 3, 2017.

Price, EW et al. "Matching chelators to radiometals for radiopharmaceuticals," Chem. Soc. Rev. 43:260-290 (2014).

Sako, D., et al. "A sulfated peptide segment at the amino terminus of PSGL-1 is critical for P-selectin binding," Cell, 33: 323-331 (1995).

Sako, et al. "Expression cloning of a functional glycoprotein ligand for P-selectin," Cell 75:1179-1186 (1993).

Swaroop, et al.,, "A conserved retina-specific gene encodes a basic motif/leucine zipper domain," Proc. Natl. Acad. Sci, 89: 266-270 (1992).

Umeki, S. et al. "Anti-adhesive property of P-selectin glycoprotein Ligand-1 (PSGL-1) due to steric hindrance effect," Journal of Cellular Biochemistry 114:1271-1285 (2013).

Hartley, J.L. "Why Proteins in Mammalian Cells?" In: Protein Expression in Mammalian Cells. Methods in Molecular Biology (Methods and Protocols), Hartley J. (eds), vol. 801, Humana Press (2012).

Riley LG, Ralston GB, Weiss AS, "Multimer formation as a consequence of separate homodimerization domains: the human c-Jun leucine zipper is a transplantable dimerization module," Protein Eng., 9(2):223-30 (1996).

* cited by examiner

SEQUENCE LISTING

```
<160> NUMBER OF SEQ ID NOS: 39

<210> SEQ ID NO 1
<211> LENGTH: 381
<212> TYPE: DNA
<213> ORGANISM: Artificial Sequence
<220> FEATURE:
<223> OTHER INFORMATION: fusion protein CDS
<220> FEATURE:
<221> NAME/KEY: CDS
<222> LOCATION: (1)..(381)
<223> OTHER INFORMATION: variant 1

<400> SEQUENCE: 1 atg gaa tgg agc tgg gtc ttt ctc ttc ttc ctg tca gta acg act ggt      48
Met Glu Trp Ser Trp Val Phe Leu Phe Phe Leu Ser Val Thr Thr Gly
1               5                   10                  15 gtc cac tcc cag gcc acc gaa tat gag tac cta gat tat gat ttc ctg      96
Val His Ser Gln Ala Thr Glu Tyr Glu Tyr Leu Asp Tyr Asp Phe Leu
            20                  25                  30 cca gaa acg gag cct cca gaa atg ctg agg aac agc act gac acc act     144
Pro Glu Thr Glu Pro Pro Glu Met Leu Arg Asn Ser Thr Asp Thr Thr
        35                  40                  45 cct ctg act ggg cct gga acc cct gag tct acc act gtg gag cct gct     192
Pro Leu Thr Gly Pro Gly Thr Pro Glu Ser Thr Thr Val Glu Pro Ala
    50                  55                  60 gcg cgg ccg cac aca tgc cca ccg tgc cca ctg cag cag aga aga ggc     240
Ala Arg Pro His Thr Cys Pro Pro Cys Pro Leu Gln Gln Arg Arg Gly
65                  70                  75                  80 ctg gaa gcc gag aga gcc aga ctg gcc gct cag ctg gat gcc ctg aga     288
Leu Glu Ala Glu Arg Ala Arg Leu Ala Ala Gln Leu Asp Ala Leu Arg
                85                  90                  95 gct gaa gtg gcc cgg ctg gcc aga gag aga gat ctg tac ggc gga ggc     336
Ala Glu Val Ala Arg Leu Ala Arg Glu Arg Asp Leu Tyr Gly Gly Gly
            100                 105                 110 gga gct ggt ggc ggc gga gac tac aag gac gac gac gac aag tga        381
Gly Ala Gly Gly Gly Gly Asp Tyr Lys Asp Asp Asp Asp Lys
        115                 120                 125
```

```
<210> SEQ ID NO 2
<211> LENGTH: 126
<212> TYPE: PRT
<213> ORGANISM: Artificial Sequence
<220> FEATURE:
<223> OTHER INFORMATION: Synthetic Construct

<400> SEQUENCE: 2

Met Glu Trp Ser Trp Val Phe Leu Phe Phe Leu Ser Val Thr Thr Gly
1               5                   10                  15

Val His Ser Gln Ala Thr Glu Tyr Glu Tyr Leu Asp Tyr Asp Phe Leu
            20                  25                  30

Pro Glu Thr Glu Pro Pro Glu Met Leu Arg Asn Ser Thr Asp Thr Thr
        35                  40                  45

Pro Leu Thr Gly Pro Gly Thr Pro Glu Ser Thr Thr Val Glu Pro Ala
    50                  55                  60

Ala Arg Pro His Thr Cys Pro Pro Cys Pro Leu Gln Gln Arg Arg Gly
65                  70                  75                  80

Leu Glu Ala Glu Arg Ala Arg Leu Ala Ala Gln Leu Asp Ala Leu Arg
                85                  90                  95

Ala Glu Val Ala Arg Leu Ala Arg Glu Arg Asp Leu Tyr Gly Gly Gly
            100                 105                 110

Gly Ala Gly Gly Gly Gly Asp Tyr Lys Asp Asp Asp Lys
        115                 120                 125

<210> SEQ ID NO 3
<211> LENGTH: 573
<212> TYPE: DNA
<213> ORGANISM: Artificial Sequence
<220> FEATURE:
<223> OTHER INFORMATION: fusion protein CDS
<220> FEATURE:
<221> NAME/KEY: CDS
<222> LOCATION: (1)..(573)
<223> OTHER INFORMATION: variant 2

<400> SEQUENCE: 3 atg gaa tgg agc tgg gtc ttt ctc ttc ttc ctg tca gta acg act ggt    48
Met Glu Trp Ser Trp Val Phe Leu Phe Phe Leu Ser Val Thr Thr Gly
1               5                   10                  15 gtc cac tcc cag gcc acc gaa tat gag tac cta gat tat gat ttc ctg    96
Val His Ser Gln Ala Thr Glu Tyr Glu Tyr Leu Asp Tyr Asp Phe Leu
            20                  25                  30 cca gaa acg gag cct cca gaa atg ctg agg aac agc act gac acc act   144
Pro Glu Thr Glu Pro Pro Glu Met Leu Arg Asn Ser Thr Asp Thr Thr
        35                  40                  45 cct ctg act ggg cct gga acc cct gag tct acc act gtg gag cct gct   192
Pro Leu Thr Gly Pro Gly Thr Pro Glu Ser Thr Thr Val Glu Pro Ala
    50                  55                  60 gcg cgg ccg cac aca tgc cca ccg tgc cca ggg cag ccc cga gaa cca   240
Ala Arg Pro His Thr Cys Pro Pro Cys Pro Gly Gln Pro Arg Glu Pro
65                  70                  75                  80 cag gtg tac acc ctg ccc cca tcc cgg gat gag ctg acc gct aac cag   288
Gln Val Tyr Thr Leu Pro Pro Ser Arg Asp Glu Leu Thr Ala Asn Gln
                85                  90                  95 gtc agc ctg acc tgc ctg gtc gca ggc ttc tat ccc agc gac atc gcc   336
Val Ser Leu Thr Cys Leu Val Ala Gly Phe Tyr Pro Ser Asp Ile Ala
            100                 105                 110 gtg gag tgg gag agc aat ggg cag ccg gag aac aac tac gct acc acg   384
Val Glu Trp Glu Ser Asn Gly Gln Pro Glu Asn Asn Tyr Ala Thr Thr
        115                 120                 125
```

```
cct ccc gtg ctg gac tcc gac ggc tcc ttc ttc ctc tac agc gca ctc     432
Pro Pro Val Leu Asp Ser Asp Gly Ser Phe Phe Leu Tyr Ser Ala Leu
        130                 135                 140 acc gtg gac gct agc agg tgg cag cag ggg aac gtc ttc tca tgc tcc     480
Thr Val Asp Ala Ser Arg Trp Gln Gln Gly Asn Val Phe Ser Cys Ser
145                 150                 155                 160 gtg atg cat gag gct ctg cac aac cac tac acg cag gca agc ctc tcc     528
Val Met His Glu Ala Leu His Asn His Tyr Thr Gln Ala Ser Leu Ser
                165                 170                 175 ctg tct ccg ggt ggc gga gac tac aag gac gac gac gac aag tga         573
Leu Ser Pro Gly Gly Gly Asp Tyr Lys Asp Asp Asp Asp Lys
                180                 185                 190
```

<210> SEQ ID NO 4
<211> LENGTH: 190
<212> TYPE: PRT
<213> ORGANISM: Artificial Sequence
<220> FEATURE:
<223> OTHER INFORMATION: Synthetic Construct

<400> SEQUENCE: 4

```
Met Glu Trp Ser Trp Val Phe Leu Phe Phe Leu Ser Val Thr Thr Gly
1               5                   10                  15

Val His Ser Gln Ala Thr Glu Tyr Glu Tyr Leu Asp Tyr Asp Phe Leu
                20                  25                  30

Pro Glu Thr Glu Pro Pro Glu Met Leu Arg Asn Ser Thr Asp Thr Thr
            35                  40                  45

Pro Leu Thr Gly Pro Gly Thr Pro Glu Ser Thr Thr Val Glu Pro Ala
    50                  55                  60

Ala Arg Pro His Thr Cys Pro Pro Cys Pro Gly Gln Pro Arg Glu Pro
65                  70                  75                  80

Gln Val Tyr Thr Leu Pro Pro Ser Arg Asp Glu Leu Thr Ala Asn Gln
                85                  90                  95

Val Ser Leu Thr Cys Leu Val Ala Gly Phe Tyr Pro Ser Asp Ile Ala
            100                 105                 110

Val Glu Trp Glu Ser Asn Gly Gln Pro Glu Asn Asn Tyr Ala Thr Thr
        115                 120                 125

Pro Pro Val Leu Asp Ser Asp Gly Ser Phe Phe Leu Tyr Ser Ala Leu
    130                 135                 140

Thr Val Asp Ala Ser Arg Trp Gln Gln Gly Asn Val Phe Ser Cys Ser
145                 150                 155                 160

Val Met His Glu Ala Leu His Asn His Tyr Thr Gln Ala Ser Leu Ser
                165                 170                 175

Leu Ser Pro Gly Gly Gly Asp Tyr Lys Asp Asp Asp Asp Lys
                180                 185                 190
```

<210> SEQ ID NO 5
<211> LENGTH: 273
<212> TYPE: DNA
<213> ORGANISM: Artificial Sequence
<220> FEATURE:
<223> OTHER INFORMATION: fusion protein CDS
<220> FEATURE:
<221> NAME/KEY: CDS
<222> LOCATION: (1)..(273)
<223> OTHER INFORMATION: variant 3

<400> SEQUENCE: 5

```
atg gaa tgg agc tgg gtc ttt ctc ttc ttc ctg tca gta acg act ggt     48
Met Glu Trp Ser Trp Val Phe Leu Phe Phe Leu Ser Val Thr Thr Gly
```

```
                 1               5                  10                 15
gtc cac tcc cag gcc acc gaa tat gag tac cta gat tat gat ttc ctg        96
Val His Ser Gln Ala Thr Glu Tyr Glu Tyr Leu Asp Tyr Asp Phe Leu
                20                  25                  30 cca gaa acg gag cct cca gaa atg ctg agg aac agc act gac acc act       144
Pro Glu Thr Glu Pro Pro Glu Met Leu Arg Asn Ser Thr Asp Thr Thr
            35                  40                  45 cct ctg act ggg cct gga acc cct gag tct acc act gtg gag cct gct       192
Pro Leu Thr Gly Pro Gly Thr Pro Glu Ser Thr Thr Val Glu Pro Ala
        50                  55                  60 gcg cgg tcc gtg gca cag tgc ctg ctg gcc atc ctg atc ctg gcc ctg       240
Ala Arg Ser Val Ala Gln Cys Leu Leu Ala Ile Leu Ile Leu Ala Leu
65                  70                  75                  80 gtg gcc gac tac aag gac gac gac gac aag tga                           273
Val Ala Asp Tyr Lys Asp Asp Asp Asp Lys
                85                  90

<210> SEQ ID NO 6
<211> LENGTH: 90
<212> TYPE: PRT
<213> ORGANISM: Artificial Sequence
<220> FEATURE:
<223> OTHER INFORMATION: Synthetic Construct

<400> SEQUENCE: 6

Met Glu Trp Ser Trp Val Phe Leu Phe Phe Leu Ser Val Thr Thr Gly
1               5                   10                  15

Val His Ser Gln Ala Thr Glu Tyr Glu Tyr Leu Asp Tyr Asp Phe Leu
                20                  25                  30

Pro Glu Thr Glu Pro Pro Glu Met Leu Arg Asn Ser Thr Asp Thr Thr
            35                  40                  45

Pro Leu Thr Gly Pro Gly Thr Pro Glu Ser Thr Thr Val Glu Pro Ala
        50                  55                  60

Ala Arg Ser Val Ala Gln Cys Leu Leu Ala Ile Leu Ile Leu Ala Leu
65                  70                  75                  80

Val Ala Asp Tyr Lys Asp Asp Asp Asp Lys
                85                  90

<210> SEQ ID NO 7
<211> LENGTH: 294
<212> TYPE: DNA
<213> ORGANISM: Artificial Sequence
<220> FEATURE:
<223> OTHER INFORMATION: fusion protein CDS
<220> FEATURE:
<221> NAME/KEY: CDS
<222> LOCATION: (1)..(294)
<223> OTHER INFORMATION: variant 4

<400> SEQUENCE: 7 atg gaa tgg agc tgg gtc ttt ctc ttc ttc ctg tca gta acg act ggt        48
Met Glu Trp Ser Trp Val Phe Leu Phe Phe Leu Ser Val Thr Thr Gly
1               5                   10                  15 gtc cac tcc cag gcc acc gaa tat gag tac cta gat tat gat ttc ctg        96
Val His Ser Gln Ala Thr Glu Tyr Glu Tyr Leu Asp Tyr Asp Phe Leu
                20                  25                  30 cca gaa acg gag cct cca gaa atg ctg agg aac agc act gac acc act       144
Pro Glu Thr Glu Pro Pro Glu Met Leu Arg Asn Ser Thr Asp Thr Thr
            35                  40                  45 cct ctg act ggg cct gga acc cct gag tct acc act gtg gag cct gct       192
Pro Leu Thr Gly Pro Gly Thr Pro Glu Ser Thr Thr Val Glu Pro Ala
        50                  55                  60
```

```
gcg cgg ccg cac aca tgc cca ccg tgc cca gca cct gaa gcc ctg ggg      240
Ala Arg Pro His Thr Cys Pro Pro Cys Pro Ala Pro Glu Ala Leu Gly
 65                  70                  75                  80 gca ccg tca gtc ttc ctc ttc ccc cca gat tac aag gat gac gac gat      288
Ala Pro Ser Val Phe Leu Phe Pro Pro Asp Tyr Lys Asp Asp Asp Asp
                 85                  90                  95 aaa tga                                                              294
Lys

<210> SEQ ID NO 8
<211> LENGTH: 97
<212> TYPE: PRT
<213> ORGANISM: Artificial Sequence
<220> FEATURE:
<223> OTHER INFORMATION: Synthetic Construct

<400> SEQUENCE: 8

Met Glu Trp Ser Trp Val Phe Leu Phe Phe Leu Ser Val Thr Thr Gly
 1               5                  10                  15

Val His Ser Gln Ala Thr Glu Tyr Glu Tyr Leu Asp Tyr Asp Phe Leu
                20                  25                  30

Pro Glu Thr Glu Pro Pro Glu Met Leu Arg Asn Ser Thr Asp Thr Thr
            35                  40                  45

Pro Leu Thr Gly Pro Gly Thr Pro Glu Ser Thr Thr Val Glu Pro Ala
        50                  55                  60

Ala Arg Pro His Thr Cys Pro Pro Cys Pro Ala Pro Glu Ala Leu Gly
 65                  70                  75                  80

Ala Pro Ser Val Phe Leu Phe Pro Pro Asp Tyr Lys Asp Asp Asp Asp
                 85                  90                  95

Lys

<210> SEQ ID NO 9
<211> LENGTH: 360
<212> TYPE: DNA
<213> ORGANISM: Artificial Sequence
<220> FEATURE:
<223> OTHER INFORMATION: fusion protein CDS
<220> FEATURE:
<221> NAME/KEY: CDS
<222> LOCATION: (1)..(360)
<223> OTHER INFORMATION: variant 5

<400> SEQUENCE: 9 atg cct ctg caa ctc ctc ctg ttg ctg atc cta ctg ggc cct ggc aac      48
Met Pro Leu Gln Leu Leu Leu Leu Leu Ile Leu Leu Gly Pro Gly Asn
 1               5                  10                  15 agc ttg cag ctg tgg gac acc tgg gca gat gaa gcc gag aaa gcc ttg      96
Ser Leu Gln Leu Trp Asp Thr Trp Ala Asp Glu Ala Glu Lys Ala Leu
                20                  25                  30 ggt ccc ctg ctt gcc cgg gac cgg aga cag gcc acc gaa tat gag tac     144
Gly Pro Leu Leu Ala Arg Asp Arg Arg Gln Ala Thr Glu Tyr Glu Tyr
            35                  40                  45 cta gat tat gat ttc ctg cca gaa acg gag cct cca gaa atg ctg agg     192
Leu Asp Tyr Asp Phe Leu Pro Glu Thr Glu Pro Pro Glu Met Leu Arg
        50                  55                  60 aac agc act gac acc act cct ctg act ggg cct gga acc cct gag tct     240
Asn Ser Thr Asp Thr Thr Pro Leu Thr Gly Pro Gly Thr Pro Glu Ser
 65                  70                  75                  80 acc act gtg gag cct gct gcg cgg ccg cac aca tgc cca ccg tgc cca     288
Thr Thr Val Glu Pro Ala Ala Arg Pro His Thr Cys Pro Pro Cys Pro
                 85                  90                  95
```

```
gca cct gaa gcc ctg ggg gca ccg tca gtc ttc ctc ttc ccc cca gat    336
Ala Pro Glu Ala Leu Gly Ala Pro Ser Val Phe Leu Phe Pro Pro Asp
            100                 105                 110 tac aag gat gac gac gat aaa tga                                     360
Tyr Lys Asp Asp Asp Asp Lys
        115
```

<210> SEQ ID NO 10
<211> LENGTH: 119
<212> TYPE: PRT
<213> ORGANISM: Artificial Sequence
<220> FEATURE:
<223> OTHER INFORMATION: Synthetic Construct

<400> SEQUENCE: 10

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Pro His Thr Cys Pro Pro Cys Pro
                85                  90                  95

Ala Pro Glu Ala Leu Gly Ala Pro Ser Val Phe Leu Phe Pro Pro Asp
            100                 105                 110

Tyr Lys Asp Asp Asp Asp Lys
        115
```

<210> SEQ ID NO 11
<211> LENGTH: 371
<212> TYPE: PRT
<213> ORGANISM: Homo sapiens
<220> FEATURE:
<221> NAME/KEY: mat_peptide
<222> LOCATION: (1)..(371)
<223> OTHER INFORMATION: PSGL-1 GI:2498904. Mature peptide 42-412

<400> SEQUENCE: 11

```
Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
            20                  25                  30

Gly Pro Gly Thr Pro Glu Ser Thr Thr Val Glu Pro Ala Ala Arg Arg
        35                  40                  45

Ser Thr Gly Leu Asp Ala Gly Gly Ala Val Thr Glu Leu Thr Thr Glu
    50                  55                  60

Leu Ala Asn Met Gly Asn Leu Ser Thr Asp Ser Ala Ala Met Glu Ile
65                  70                  75                  80

Gln Thr Thr Gln Pro Ala Ala Thr Glu Ala Gln Thr Thr Gln Pro Val
                85                  90                  95

Pro Thr Glu Ala Gln Thr Thr Pro Leu Ala Ala Thr Glu Ala Gln Thr
            100                 105                 110

Thr Arg Leu Thr Ala Thr Glu Ala Gln Thr Thr Pro Leu Ala Ala Thr
        115                 120                 125
```

```
Glu Ala Gln Thr Thr Pro Pro Ala Ala Thr Glu Ala Gln Thr Thr Gln
            130                 135                 140

Pro Thr Gly Leu Glu Ala Gln Thr Thr Ala Pro Ala Ala Met Glu Ala
145                 150                 155                 160

Gln Thr Thr Ala Pro Ala Ala Met Glu Ala Gln Thr Thr Pro Pro Ala
                165                 170                 175

Ala Met Glu Ala Gln Thr Thr Gln Thr Thr Ala Met Glu Ala Gln Thr
            180                 185                 190

Thr Ala Pro Glu Ala Thr Glu Ala Gln Thr Thr Gln Pro Thr Ala Thr
        195                 200                 205

Glu Ala Gln Thr Thr Pro Leu Ala Ala Met Glu Ala Leu Ser Thr Glu
210                 215                 220

Pro Ser Ala Thr Glu Ala Leu Ser Met Glu Pro Thr Thr Lys Arg Gly
225                 230                 235                 240

Leu Phe Ile Pro Phe Ser Val Ser Ser Val Thr His Lys Gly Ile Pro
                245                 250                 255

Met Ala Ala Ser Asn Leu Ser Val Asn Tyr Pro Val Gly Ala Pro Asp
            260                 265                 270

His Ile Ser Val Lys Gln Cys Leu Leu Ala Ile Leu Ile Leu Ala Leu
        275                 280                 285

Val Ala Thr Ile Phe Phe Val Cys Thr Val Val Leu Ala Val Arg Leu
290                 295                 300

Ser Arg Lys Gly His Met Tyr Pro Val Arg Asn Tyr Ser Pro Thr Glu
305                 310                 315                 320

Met Val Cys Ile Ser Ser Leu Leu Pro Asp Gly Gly Glu Gly Pro Ser
                325                 330                 335

Ala Thr Ala Asn Gly Gly Leu Ser Lys Ala Lys Ser Pro Gly Leu Thr
            340                 345                 350

Pro Glu Pro Arg Glu Asp Arg Glu Gly Asp Asp Leu Thr Leu His Ser
        355                 360                 365

Phe Leu Pro
    370

<210> SEQ ID NO 12
<211> LENGTH: 237
<212> TYPE: PRT
<213> ORGANISM: Homo sapiens
<220> FEATURE:
<221> NAME/KEY: misc_feature
<223> OTHER INFORMATION: NRL: GI:1709348. Leucine zipper 187-208

<400> SEQUENCE: 12

Met Ala Leu Pro Pro Ser Pro Leu Ala Met Glu Tyr Val Asn Asp Phe
1               5                   10                  15

Asp Leu Met Lys Phe Glu Val Lys Arg Glu Pro Ser Glu Gly Arg Pro
            20                  25                  30

Gly Pro Pro Thr Ala Ser Leu Gly Ser Thr Pro Tyr Ser Ser Val Pro
        35                  40                  45

Pro Ser Pro Thr Phe Ser Glu Pro Gly Met Val Gly Ala Thr Glu Gly
    50                  55                  60

Thr Arg Pro Gly Leu Glu Glu Leu Tyr Trp Leu Ala Thr Leu Gln Gln
65                  70                  75                  80

Gln Leu Gly Ala Gly Glu Ala Leu Gly Leu Ser Pro Glu Glu Ala Met
                85                  90                  95

Glu Leu Leu Gln Gly Gln Gly Pro Val Pro Val Asp Gly Pro His Gly
            100                 105                 110
```

```
Tyr Tyr Pro Gly Ser Pro Glu Glu Thr Gly Ala Gln His Val Gln Leu
            115                 120                 125
Ala Glu Arg Phe Ser Asp Ala Ala Leu Val Ser Met Ser Val Arg Glu
        130                 135                 140
Leu Asn Arg Gln Leu Arg Gly Cys Gly Arg Asp Glu Ala Leu Arg Leu
145                 150                 155                 160
Lys Gln Arg Arg Arg Thr Leu Lys Asn Arg Gly Tyr Ala Gln Ala Cys
                165                 170                 175
Arg Ser Lys Arg Leu Gln Gln Arg Arg Gly Leu Glu Ala Glu Arg Ala
            180                 185                 190
Arg Leu Ala Ala Gln Leu Asp Ala Leu Arg Ala Glu Val Ala Arg Leu
        195                 200                 205
Ala Arg Glu Arg Asp Leu Tyr Lys Ala Arg Cys Asp Arg Leu Thr Ser
    210                 215                 220
Ser Gly Pro Gly Ser Gly Asp Pro Ser His Leu Phe Leu
225                 230                 235
```

<210> SEQ ID NO 13
<211> LENGTH: 1029
<212> TYPE: DNA
<213> ORGANISM: Homo sapiens
<220> FEATURE:
<221> NAME/KEY: CDS
<222> LOCATION: (1)..(1029)
<223> OTHER INFORMATION: FTVII

<400> SEQUENCE: 13

```
atg aat aat gct ggg cac ggc ccc acc cgg agg ctg cga ggc ttg gga        48
Met Asn Asn Ala Gly His Gly Pro Thr Arg Arg Leu Arg Gly Leu Gly
1               5                   10                  15 gtc ctg gcc ggg gtg gct ctg ctc gct gcc ctc tgg ctt ctg tgg ctg        96
Val Leu Ala Gly Val Ala Leu Leu Ala Ala Leu Trp Leu Leu Trp Leu
                20                  25                  30 ctg gga tca gca cct cgg ggt act ccg gca cct cag ccc acg atc acc       144
Leu Gly Ser Ala Pro Arg Gly Thr Pro Ala Pro Gln Pro Thr Ile Thr
            35                  40                  45 atc ctt gtc tgg cac tgg ccc ttc act gac cag cct cca gag ctg ccc       192
Ile Leu Val Trp His Trp Pro Phe Thr Asp Gln Pro Pro Glu Leu Pro
        50                  55                  60 agc gac acc tgc acc cgc tac ggc atc gcc cgc tgc cac ctg agt gcc       240
Ser Asp Thr Cys Thr Arg Tyr Gly Ile Ala Arg Cys His Leu Ser Ala
65                  70                  75                  80 aac cga agc ctg ctg gcc agc gcc gac gcc gtg gtc ttc cac cac cgc       288
Asn Arg Ser Leu Leu Ala Ser Ala Asp Ala Val Val Phe His His Arg
                85                  90                  95 gag ctt cag acc cga cgg tcc cac ctg ccc ctg gcc cag cga ccg cga       336
Glu Leu Gln Thr Arg Arg Ser His Leu Pro Leu Ala Gln Arg Pro Arg
            100                 105                 110 ggg cag ccc tgg gtg tgg gcc tcc atg gag tct cct agc cac acc cac       384
Gly Gln Pro Trp Val Trp Ala Ser Met Glu Ser Pro Ser His Thr His
        115                 120                 125 ggc ctc agc cac ctc cga ggc atc ttc aac tgg gtg ctg agc tac cgg       432
Gly Leu Ser His Leu Arg Gly Ile Phe Asn Trp Val Leu Ser Tyr Arg
    130                 135                 140 cgc gac tcg gac atc ttt gtg ccc tat ggc cgc ctg gag cct cac tgg       480
Arg Asp Ser Asp Ile Phe Val Pro Tyr Gly Arg Leu Glu Pro His Trp
145                 150                 155                 160 gga ccc tcg cca ccg ctg cca gcc aag agc agg gtg gcc gcc tgg gtg       528
Gly Pro Ser Pro Pro Leu Pro Ala Lys Ser Arg Val Ala Ala Trp Val
```

```
                    165                 170                 175
gtc agc aac ttc cag gag cgg cag ctg cgt gcc agg ctg tac cgg cag          576
Val Ser Asn Phe Gln Glu Arg Gln Leu Arg Ala Arg Leu Tyr Arg Gln
        180                 185                 190 ctg gcg cct cat ctg cgg gtg gat gtc ttt ggc cgt gcc aat gga cgg          624
Leu Ala Pro His Leu Arg Val Asp Val Phe Gly Arg Ala Asn Gly Arg
195                 200                 205 cca ctg tgc gcc agc tgc ctg gtg ccc acc gtg gcc cag tac cgc ttc          672
Pro Leu Cys Ala Ser Cys Leu Val Pro Thr Val Ala Gln Tyr Arg Phe
    210                 215                 220 tac ctg tcc ttt gag aac tct cag cac cgc gac tac att acg gag aaa          720
Tyr Leu Ser Phe Glu Asn Ser Gln His Arg Asp Tyr Ile Thr Glu Lys
225                 230                 235                 240 ttc tgg cgc aac gca ctg gtg gct ggc act gtg cca gtg gtg ctg gga          768
Phe Trp Arg Asn Ala Leu Val Ala Gly Thr Val Pro Val Val Leu Gly
                245                 250                 255 cct cca cgg gcc acc tat gag gcc ttc gtg ccg gct gac gcc ttc gtg          816
Pro Pro Arg Ala Thr Tyr Glu Ala Phe Val Pro Ala Asp Ala Phe Val
            260                 265                 270 cat gtg gat gac ttt ggc tca gcc cga gag ctg gcg gct ttc ctc act          864
His Val Asp Asp Phe Gly Ser Ala Arg Glu Leu Ala Ala Phe Leu Thr
        275                 280                 285 ggc atg aat gag agc cga tac caa cgc ttc ttt gcc tgg cgt gac agg          912
Gly Met Asn Glu Ser Arg Tyr Gln Arg Phe Phe Ala Trp Arg Asp Arg
    290                 295                 300 ctc cgc gtg cga ctg ttc acc gac tgg cgg gaa cgt ttc tgt gcc atc          960
Leu Arg Val Arg Leu Phe Thr Asp Trp Arg Glu Arg Phe Cys Ala Ile
305                 310                 315                 320 tgt gac cgc tac cca cac cta cct cgc agc caa gtc tat gag gac ctt         1008
Cys Asp Arg Tyr Pro His Leu Pro Arg Ser Gln Val Tyr Glu Asp Leu
                325                 330                 335 gag ggt tgg ttt cag gcc tga                                              1029
Glu Gly Trp Phe Gln Ala
            340
```

<210> SEQ ID NO 14
<211> LENGTH: 342
<212> TYPE: PRT
<213> ORGANISM: Homo sapiens

<400> SEQUENCE: 14

```
Met Asn Asn Ala Gly His Gly Pro Thr Arg Leu Arg Gly Leu Gly
1               5                   10                  15

Val Leu Ala Gly Val Ala Leu Leu Ala Ala Leu Trp Leu Leu Trp Leu
                20                  25                  30

Leu Gly Ser Ala Pro Arg Gly Thr Pro Ala Pro Gln Pro Thr Ile Thr
            35                  40                  45

Ile Leu Val Trp His Trp Pro Phe Thr Asp Gln Pro Pro Glu Leu Pro
    50                  55                  60

Ser Asp Thr Cys Thr Arg Tyr Gly Ile Ala Arg Cys His Leu Ser Ala
65                  70                  75                  80

Asn Arg Ser Leu Leu Ala Ser Ala Asp Ala Val Val Phe His His Arg
                85                  90                  95

Glu Leu Gln Thr Arg Arg Ser His Leu Pro Leu Ala Gln Arg Pro Arg
            100                 105                 110

Gly Gln Pro Trp Val Trp Ala Ser Met Glu Ser Pro Ser His Thr His
        115                 120                 125

Gly Leu Ser His Leu Arg Gly Ile Phe Asn Trp Val Leu Ser Tyr Arg
```

```
                    130                 135                 140
Arg Asp Ser Asp Ile Phe Val Pro Tyr Gly Arg Leu Glu Pro His Trp
145                 150                 155                 160

Gly Pro Ser Pro Pro Leu Pro Ala Lys Ser Arg Val Ala Ala Trp Val
                165                 170                 175

Val Ser Asn Phe Gln Glu Arg Gln Leu Arg Ala Arg Leu Tyr Arg Gln
            180                 185                 190

Leu Ala Pro His Leu Arg Val Asp Val Phe Gly Arg Ala Asn Gly Arg
        195                 200                 205

Pro Leu Cys Ala Ser Cys Leu Val Pro Thr Val Ala Gln Tyr Arg Phe
    210                 215                 220

Tyr Leu Ser Phe Glu Asn Ser Gln His Arg Asp Tyr Ile Thr Glu Lys
225                 230                 235                 240

Phe Trp Arg Asn Ala Leu Val Ala Gly Thr Val Pro Val Val Leu Gly
                245                 250                 255

Pro Pro Arg Ala Thr Tyr Glu Ala Phe Val Pro Ala Asp Ala Phe Val
                260                 265                 270

His Val Asp Asp Phe Gly Ser Ala Arg Glu Leu Ala Ala Phe Leu Thr
        275                 280                 285

Gly Met Asn Glu Ser Arg Tyr Gln Arg Phe Phe Ala Trp Arg Asp Arg
    290                 295                 300

Leu Arg Val Arg Leu Phe Thr Asp Trp Arg Glu Arg Phe Cys Ala Ile
305                 310                 315                 320

Cys Asp Arg Tyr Pro His Leu Pro Arg Ser Gln Val Tyr Glu Asp Leu
                325                 330                 335

Glu Gly Trp Phe Gln Ala
            340

<210> SEQ ID NO 15
<211> LENGTH: 1287
<212> TYPE: DNA
<213> ORGANISM: homo sapiens
<220> FEATURE:
<221> NAME/KEY: CDS
<222> LOCATION: (1)..(1287)
<223> OTHER INFORMATION: C2GnT

<400> SEQUENCE: 15 atg ctg agg acg ttg ctg cga agg aga ctt ttt tct tat ccc acc aaa        48
Met Leu Arg Thr Leu Leu Arg Arg Arg Leu Phe Ser Tyr Pro Thr Lys
1               5                   10                  15 tac tac ttt atg gtt ctt gtt tta tcc cta atc acc ttc tcc gtt tta       96
Tyr Tyr Phe Met Val Leu Val Leu Ser Leu Ile Thr Phe Ser Val Leu
            20                  25                  30 agg att cat caa aag cct gaa ttt gta agt gtc aga cac ttg gag ctt      144
Arg Ile His Gln Lys Pro Glu Phe Val Ser Val Arg His Leu Glu Leu
        35                  40                  45 gct ggg gag aat cct agt agt gat att aat tgc acc aaa gtt tta cag      192
Ala Gly Glu Asn Pro Ser Ser Asp Ile Asn Cys Thr Lys Val Leu Gln
    50                  55                  60 ggt gat gta aat gaa atc caa aag gta aag ctt gag atc cta aca gtg      240
Gly Asp Val Asn Glu Ile Gln Lys Val Lys Leu Glu Ile Leu Thr Val
65                  70                  75                  80 aaa ttt aaa aag cgc cct cgg tgg aca cct gac gac tat ata aac atg      288
Lys Phe Lys Lys Arg Pro Arg Trp Thr Pro Asp Asp Tyr Ile Asn Met
                85                  90                  95 acc agt gac tgt tct tct ttc atc aag aga cgc aaa tat att gta gaa      336
Thr Ser Asp Cys Ser Ser Phe Ile Lys Arg Arg Lys Tyr Ile Val Glu
```

-continued

|  |  |  |  |  |  |  |  |  |  |  |  |  |  |  |  |  |
|---|---|---|---|---|---|---|---|---|---|---|---|---|---|---|---|---|
|  |  |  | 100 |  |  |  | 105 |  |  |  | 110 |  |  |  |  |  |
| ccc | ctt | agt | aaa | gaa | gag | gcg | gag | ttt | cca | ata | gca | tat | tct | ata | gtg | 384 |
| Pro | Leu | Ser | Lys | Glu | Glu | Ala | Glu | Phe | Pro | Ile | Ala | Tyr | Ser | Ile | Val |  |
|  |  | 115 |  |  |  |  | 120 |  |  |  |  | 125 |  |  |  |  |
| gtt | cat | cac | aag | att | gaa | atg | ctt | gac | agg | ctg | ctg | agg | gcc | atc | tat | 432 |
| Val | His | His | Lys | Ile | Glu | Met | Leu | Asp | Arg | Leu | Leu | Arg | Ala | Ile | Tyr |  |
| 130 |  |  |  |  | 135 |  |  |  |  | 140 |  |  |  |  |  |  |
| atg | cct | cag | aat | ttc | tat | tgc | att | cat | gtg | gac | aca | aaa | tcc | gag | gat | 480 |
| Met | Pro | Gln | Asn | Phe | Tyr | Cys | Ile | His | Val | Asp | Thr | Lys | Ser | Glu | Asp |  |
| 145 |  |  |  |  | 150 |  |  |  |  | 155 |  |  |  |  | 160 |  |
| tcc | tat | tta | gct | gca | gtg | atg | ggc | atc | gct | tcc | tgt | ttt | agt | aat | gtc | 528 |
| Ser | Tyr | Leu | Ala | Ala | Val | Met | Gly | Ile | Ala | Ser | Cys | Phe | Ser | Asn | Val |  |
|  |  |  |  | 165 |  |  |  |  | 170 |  |  |  |  | 175 |  |  |
| ttt | gtg | gcc | agc | cga | ttg | gag | agt | gtg | gtt | tat | gca | tcg | tgg | agc | cgg | 576 |
| Phe | Val | Ala | Ser | Arg | Leu | Glu | Ser | Val | Val | Tyr | Ala | Ser | Trp | Ser | Arg |  |
|  |  |  | 180 |  |  |  |  | 185 |  |  |  |  | 190 |  |  |  |
| gtt | cag | gct | gac | ctc | aac | tgc | atg | aag | gat | ctc | tat | gca | atg | agt | gca | 624 |
| Val | Gln | Ala | Asp | Leu | Asn | Cys | Met | Lys | Asp | Leu | Tyr | Ala | Met | Ser | Ala |  |
|  |  | 195 |  |  |  |  | 200 |  |  |  |  | 205 |  |  |  |  |
| aac | tgg | aag | tac | ttg | ata | aat | ctt | tgt | ggt | atg | gat | ttt | ccc | att | aaa | 672 |
| Asn | Trp | Lys | Tyr | Leu | Ile | Asn | Leu | Cys | Gly | Met | Asp | Phe | Pro | Ile | Lys |  |
|  | 210 |  |  |  |  | 215 |  |  |  |  | 220 |  |  |  |  |  |
| acc | aac | cta | gaa | att | gtc | agg | aag | ctc | aag | ttg | tta | atg | gga | gaa | aac | 720 |
| Thr | Asn | Leu | Glu | Ile | Val | Arg | Lys | Leu | Lys | Leu | Leu | Met | Gly | Glu | Asn |  |
| 225 |  |  |  |  | 230 |  |  |  |  | 235 |  |  |  |  | 240 |  |
| aac | ctg | gaa | acg | gag | agg | atg | cca | tcc | cat | aaa | gaa | gaa | agg | tgg | aag | 768 |
| Asn | Leu | Glu | Thr | Glu | Arg | Met | Pro | Ser | His | Lys | Glu | Glu | Arg | Trp | Lys |  |
|  |  |  |  | 245 |  |  |  |  | 250 |  |  |  |  | 255 |  |  |
| aag | cgg | tat | gag | gtc | gtt | aat | gga | aag | ctg | aca | aac | aca | ggg | act | gtc | 816 |
| Lys | Arg | Tyr | Glu | Val | Val | Asn | Gly | Lys | Leu | Thr | Asn | Thr | Gly | Thr | Val |  |
|  |  |  | 260 |  |  |  |  | 265 |  |  |  |  | 270 |  |  |  |
| aaa | atg | ctt | cct | cca | ctc | gaa | aca | cct | ctc | ttt | tct | ggc | agt | gcc | tac | 864 |
| Lys | Met | Leu | Pro | Pro | Leu | Glu | Thr | Pro | Leu | Phe | Ser | Gly | Ser | Ala | Tyr |  |
|  |  | 275 |  |  |  |  | 280 |  |  |  |  | 285 |  |  |  |  |
| ttc | gtg | gtc | agt | agg | gag | tat | gtg | ggg | tat | gta | cta | cag | aat | gaa | aaa | 912 |
| Phe | Val | Val | Ser | Arg | Glu | Tyr | Val | Gly | Tyr | Val | Leu | Gln | Asn | Glu | Lys |  |
|  | 290 |  |  |  |  | 295 |  |  |  |  | 300 |  |  |  |  |  |
| atc | caa | aag | ttg | atg | gag | tgg | gca | caa | gac | aca | tac | agc | cct | gat | gag | 960 |
| Ile | Gln | Lys | Leu | Met | Glu | Trp | Ala | Gln | Asp | Thr | Tyr | Ser | Pro | Asp | Glu |  |
| 305 |  |  |  |  | 310 |  |  |  |  | 315 |  |  |  |  | 320 |  |
| tat | ctc | tgg | gcc | acc | atc | caa | agg | att | cct | gaa | gtc | ccg | ggc | tca | ctc | 1008 |
| Tyr | Leu | Trp | Ala | Thr | Ile | Gln | Arg | Ile | Pro | Glu | Val | Pro | Gly | Ser | Leu |  |
|  |  |  |  | 325 |  |  |  |  | 330 |  |  |  |  | 335 |  |  |
| cct | gcc | agc | cat | aag | tat | gat | cta | tct | gac | atg | caa | gca | gtt | gcc | agg | 1056 |
| Pro | Ala | Ser | His | Lys | Tyr | Asp | Leu | Ser | Asp | Met | Gln | Ala | Val | Ala | Arg |  |
|  |  |  | 340 |  |  |  |  | 345 |  |  |  |  | 350 |  |  |  |
| ttt | gtc | aag | tgg | cag | tac | ttt | gag | ggt | gat | gtt | tcc | aag | ggt | gct | ccc | 1104 |
| Phe | Val | Lys | Trp | Gln | Tyr | Phe | Glu | Gly | Asp | Val | Ser | Lys | Gly | Ala | Pro |  |
|  |  | 355 |  |  |  |  | 360 |  |  |  |  | 365 |  |  |  |  |
| tac | ccg | ccc | tgc | gat | gga | gtc | cat | gtg | cgc | tca | gtg | tgc | att | ttc | gga | 1152 |
| Tyr | Pro | Pro | Cys | Asp | Gly | Val | His | Val | Arg | Ser | Val | Cys | Ile | Phe | Gly |  |
|  | 370 |  |  |  |  | 375 |  |  |  |  | 380 |  |  |  |  |  |
| gct | ggt | gac | ttg | aac | tgg | atg | ctg | cgc | aaa | cac | cac | ttg | ttt | gcc | aat | 1200 |
| Ala | Gly | Asp | Leu | Asn | Trp | Met | Leu | Arg | Lys | His | His | Leu | Phe | Ala | Asn |  |
| 385 |  |  |  |  | 390 |  |  |  |  | 395 |  |  |  |  | 400 |  |
| aag | ttt | gac | gtg | gat | gtt | gac | ctc | ttt | gcc | atc | cag | tgt | ttg | gat | gag | 1248 |
| Lys | Phe | Asp | Val | Asp | Val | Asp | Leu | Phe | Ala | Ile | Gln | Cys | Leu | Asp | Glu |  |
|  |  |  |  | 405 |  |  |  |  | 410 |  |  |  |  | 415 |  |  |
| cat | ttg | aga | cac | aaa | gct | ttg | gag | aca | tta | aaa | cac | tga |  |  |  | 1287 |

His Leu Arg His Lys Ala Leu Glu Thr Leu Lys His
            420                 425

<210> SEQ ID NO 16
<211> LENGTH: 428
<212> TYPE: PRT
<213> ORGANISM: homo sapiens

<400> SEQUENCE: 16

Met Leu Arg Thr Leu Arg Arg Leu Phe Ser Tyr Pro Thr Lys
1               5                   10                  15

Tyr Tyr Phe Met Val Leu Val Leu Ser Leu Ile Thr Phe Ser Val Leu
                20                  25                  30

Arg Ile His Gln Lys Pro Glu Phe Val Ser Val Arg His Leu Glu Leu
            35                  40                  45

Ala Gly Glu Asn Pro Ser Ser Asp Ile Asn Cys Thr Lys Val Leu Gln
    50                  55                  60

Gly Asp Val Asn Glu Ile Gln Lys Val Lys Leu Glu Ile Leu Thr Val
65                  70                  75                  80

Lys Phe Lys Lys Arg Pro Arg Trp Thr Pro Asp Asp Tyr Ile Asn Met
                85                  90                  95

Thr Ser Asp Cys Ser Ser Phe Ile Lys Arg Arg Lys Tyr Ile Val Glu
            100                 105                 110

Pro Leu Ser Lys Glu Glu Ala Glu Phe Pro Ile Ala Tyr Ser Ile Val
        115                 120                 125

Val His His Lys Ile Glu Met Leu Asp Arg Leu Leu Arg Ala Ile Tyr
    130                 135                 140

Met Pro Gln Asn Phe Tyr Cys Ile His Val Asp Thr Lys Ser Glu Asp
145                 150                 155                 160

Ser Tyr Leu Ala Ala Val Met Gly Ile Ala Ser Cys Phe Ser Asn Val
                165                 170                 175

Phe Val Ala Ser Arg Leu Glu Ser Val Val Tyr Ala Ser Trp Ser Arg
            180                 185                 190

Val Gln Ala Asp Leu Asn Cys Met Lys Asp Leu Tyr Ala Met Ser Ala
        195                 200                 205

Asn Trp Lys Tyr Leu Ile Asn Leu Cys Gly Met Asp Phe Pro Ile Lys
    210                 215                 220

Thr Asn Leu Glu Ile Val Arg Lys Leu Lys Leu Leu Met Gly Glu Asn
225                 230                 235                 240

Asn Leu Glu Thr Glu Arg Met Pro Ser His Lys Glu Glu Arg Trp Lys
                245                 250                 255

Lys Arg Tyr Glu Val Val Asn Gly Lys Leu Thr Asn Thr Gly Thr Val
            260                 265                 270

Lys Met Leu Pro Pro Leu Glu Thr Pro Leu Phe Ser Gly Ser Ala Tyr
        275                 280                 285

Phe Val Val Ser Arg Glu Tyr Val Gly Tyr Val Leu Gln Asn Glu Lys
    290                 295                 300

Ile Gln Lys Leu Met Glu Trp Ala Gln Asp Thr Tyr Ser Pro Asp Glu
305                 310                 315                 320

Tyr Leu Trp Ala Thr Ile Gln Arg Ile Pro Glu Val Pro Gly Ser Leu
                325                 330                 335

Pro Ala Ser His Lys Tyr Asp Leu Ser Asp Met Gln Ala Val Ala Arg
            340                 345                 350

Phe Val Lys Trp Gln Tyr Phe Glu Gly Asp Val Ser Lys Gly Ala Pro
        355                 360                 365

Tyr Pro Pro Cys Asp Gly Val His Val Arg Ser Val Cys Ile Phe Gly
            370                 375                 380

Ala Gly Asp Leu Asn Trp Met Leu Arg Lys His His Leu Phe Ala Asn
385                 390                 395                 400

Lys Phe Asp Val Asp Val Asp Leu Phe Ala Ile Gln Cys Leu Asp Glu
                405                 410                 415

His Leu Arg His Lys Ala Leu Glu Thr Leu Lys His
            420                 425

<210> SEQ ID NO 17
<211> LENGTH: 11
<212> TYPE: PRT
<213> ORGANISM: Artificial Sequence
<220> FEATURE:
<223> OTHER INFORMATION: spacer
<220> FEATURE:
<221> NAME/KEY: PEPTIDE
<222> LOCATION: (1)..(11)
<223> OTHER INFORMATION: spacer

<400> SEQUENCE: 17

Gly Gly Gly Gly Ala Gly Gly Gly Lys Gly
1               5                   10

<210> SEQ ID NO 18
<211> LENGTH: 20
<212> TYPE: PRT
<213> ORGANISM: Mus musculus
<220> FEATURE:
<221> NAME/KEY: SIGNAL
<222> LOCATION: (1)..(20)

<400> SEQUENCE: 18

Met Glu Trp Ser Trp Trp Val Phe Leu Phe Phe Leu Ser Val Thr Thr
1               5                   10                  15

Gly Val His Ser
            20

<210> SEQ ID NO 19
<211> LENGTH: 24
<212> TYPE: DNA
<213> ORGANISM: Mus musculus
<220> FEATURE:
<221> NAME/KEY: CDS
<222> LOCATION: (1)..(24)
<223> OTHER INFORMATION: Hinge region

<400> SEQUENCE: 19 ccg cac aca tgc cca ccg tgc cca                                   24
Pro His Thr Cys Pro Pro Cys Pro
1               5

<210> SEQ ID NO 20
<211> LENGTH: 8
<212> TYPE: PRT
<213> ORGANISM: Mus musculus

<400> SEQUENCE: 20

Pro His Thr Cys Pro Pro Cys Pro
1               5

<210> SEQ ID NO 21
<211> LENGTH: 19
<212> TYPE: PRT
<213> ORGANISM: Mus musculus

```
<220> FEATURE:
<221> NAME/KEY: SIGNAL
<222> LOCATION: (1)..(19)

<400> SEQUENCE: 21

Met Ala Trp Thr Ser Leu Ile Leu Ser Leu Leu Ala Leu Cys Ser Gly
1               5                   10                  15

Ala Ser Ser

<210> SEQ ID NO 22
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 22

Met Gly Trp Ser Trp Ile Phe Leu Phe Leu Leu Ser Gly Thr Ala Gly
1               5                   10                  15

Val His Ser

<210> SEQ ID NO 23
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 23

Met Gly Trp Ser Cys Ile Ile Leu Phe Leu Val Ala Thr Ala Thr Gly
1               5                   10                  15

Val His Ser

<210> SEQ ID NO 24
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 24

Met Gly Trp Ser Cys Ile Ile Leu Phe Leu Val Ala Thr Ala Thr Gly
1               5                   10                  15

Val His Ser

<210> SEQ ID NO 25
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 25

Met Ala Val Leu Gly Leu Leu Phe Cys Leu Val Thr Phe Pro Ser Cys
1               5                   10                  15

Val Leu Ser

<210> SEQ ID NO 26
<211> LENGTH: 19
<212> TYPE: PRT
```

```
<213> ORGANISM: Mus musculus
<220> FEATURE:
<221> NAME/KEY: SIGNAL
<222> LOCATION: (1)..(19)

<400> SEQUENCE: 26

Met Gly Trp Ser Cys Ile Ile Leu Phe Leu Val Ala Ala Ala Asn Gly
1               5                   10                  15

Val His Ser

<210> SEQ ID NO 27
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 27

Met Gly Thr Val Ser Arg Ala Ala Leu Ile Leu Ala Cys Leu Ala Leu
1               5                   10                  15

Ala Ser Ala

<210> SEQ ID NO 28
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 28

Met Gly Trp Ser Cys Ile Met Leu Phe Leu Ala Ala Thr Ala Thr Gly
1               5                   10                  15

Val His Ser

<210> SEQ ID NO 29
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 29

Met Asn Pro Ala Ile Ser Val Ala Leu Leu Leu Ser Val Leu Gln Val
1               5                   10                  15

Ser Arg Gly

<210> SEQ ID NO 30
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 30

Met Ala Leu Met Leu Val Leu Phe Phe Leu Ala Ala Val Leu Pro Pro
1               5                   10                  15

Ser Leu Leu

<210> SEQ ID NO 31
<211> LENGTH: 19
```

```
<212> TYPE: PRT
<213> ORGANISM: Mus musculus
<220> FEATURE:
<221> NAME/KEY: SIGNAL
<222> LOCATION: (1)..(19)

<400> SEQUENCE: 31

Met Gly Trp Ser Phe Ile Phe Leu Phe Leu Leu Ser Val Thr Ala Gly
1               5                   10                  15

Val His Ser

<210> SEQ ID NO 32
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 32

Met Ile Leu Phe Asn Arg Val Gly Tyr Phe Val Ser Leu Phe Ala Thr
1               5                   10                  15

Val Ser Cys

<210> SEQ ID NO 33
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 33

Met Val Val Met Leu Arg Tyr Val Trp Pro Leu Leu Leu Cys Ser Pro
1               5                   10                  15

Cys Leu Leu

<210> SEQ ID NO 34
<211> LENGTH: 19
<212> TYPE: PRT
<213> ORGANISM: Mus musculus
<220> FEATURE:
<221> NAME/KEY: SIGNAL
<222> LOCATION: (1)..(19)

<400> SEQUENCE: 34

Met Gly Trp Arg Trp Ile Phe Leu Phe Leu Leu Ser Gly Thr Ala Gly
1               5                   10                  15

Val His Cys

<210> SEQ ID NO 35
<211> LENGTH: 7
<212> TYPE: PRT
<213> ORGANISM: Artificial Sequence
<220> FEATURE:
<223> OTHER INFORMATION: Flag seq
<220> FEATURE:
<221> NAME/KEY: BINDING
<222> LOCATION: (1)..(7)

<400> SEQUENCE: 35

Asp Tyr Asp Asp Asp Asp Lys
1               5

<210> SEQ ID NO 36
```

```
<211> LENGTH: 363
<212> TYPE: DNA
<213> ORGANISM: artificial sequence
<220> FEATURE:
<223> OTHER INFORMATION: protein 1A
<220> FEATURE:
<221> NAME/KEY: CDS
<222> LOCATION: (1)..(363)
<223> OTHER INFORMATION: Variant 1A
<220> FEATURE:
<221> NAME/KEY: misc_feature
<222> LOCATION: (1)..(57)
<223> OTHER INFORMATION: signal peptide
<220> FEATURE:
<221> NAME/KEY: misc_feature
<222> LOCATION: (58)..(360)
<223> OTHER INFORMATION: Sequence encoding Variant 1A no signal
<220> FEATURE:
<221> NAME/KEY: misc_feature
<222> LOCATION: (58)..(198)
<223> OTHER INFORMATION: sequence encoding PSGL-1 aa 1-47
<220> FEATURE:
<221> NAME/KEY: misc_feature
<222> LOCATION: (199)..(222)
<223> OTHER INFORMATION: sequence encoding covalent dimerization domain
      comprising at least one Cys
<220> FEATURE:
<221> NAME/KEY: misc_feature
<222> LOCATION: (223)..(327)
<223> OTHER INFORMATION: Sequence encoding NRL leucine zipper comprising
      at least NRL aa 187-208
<220> FEATURE:
<221> NAME/KEY: misc_feature
<222> LOCATION: (328)..(360)
<223> OTHER INFORMATION: sequence encoding a glycine spacer

<400> SEQUENCE: 36 atg gaa tgg agc tgg gtc ttt ctc ttc ttc ctg tca gta acg act ggt        48
Met Glu Trp Ser Trp Val Phe Leu Phe Phe Leu Ser Val Thr Thr Gly
1               5                   10                  15 gtc cac tcc cag gcc acc gaa tat gag tac cta gat tat gat ttc ctg        96
Val His Ser Gln Ala Thr Glu Tyr Glu Tyr Leu Asp Tyr Asp Phe Leu
            20                  25                  30 cca gaa acg gag cct cca gaa atg ctg agg aac agc act gac acc act       144
Pro Glu Thr Glu Pro Pro Glu Met Leu Arg Asn Ser Thr Asp Thr Thr
        35                  40                  45 cct ctg act ggg cct gga acc cct gag tct acc act gtg gag cct gct       192
Pro Leu Thr Gly Pro Gly Thr Pro Glu Ser Thr Thr Val Glu Pro Ala
50                  55                  60 gcg cgg ccg cac aca tgc cca ccg tgc cca ctg cag cag aga aga ggc       240
Ala Arg Pro His Thr Cys Pro Pro Cys Pro Leu Gln Gln Arg Arg Gly
65                  70                  75                  80 ctg gaa gcc gag aga gcc aga ctg gcc gct cag ctg gat gcc ctg aga       288
Leu Glu Ala Glu Arg Ala Arg Leu Ala Ala Gln Leu Asp Ala Leu Arg
                85                  90                  95 gct gaa gtg gcc cgg ctg gcc aga gag aga gat ctg tac ggc gga ggc       336
Ala Glu Val Ala Arg Leu Ala Arg Glu Arg Asp Leu Tyr Gly Gly Gly
            100                 105                 110 gga gct ggt ggc ggc gga aag ggt tga                                   363
Gly Ala Gly Gly Gly Gly Lys Gly
        115                 120

<210> SEQ ID NO 37
<211> LENGTH: 120
<212> TYPE: PRT
<213> ORGANISM: artificial sequence
<220> FEATURE:
<223> OTHER INFORMATION: Synthetic Construct

<400> SEQUENCE: 37
```

-continued

```
Met Glu Trp Ser Trp Val Phe Leu Phe Phe Leu Ser Val Thr Thr Gly
1               5                   10                  15

Val His Ser Gln Ala Thr Glu Tyr Glu Tyr Leu Asp Tyr Asp Phe Leu
                20                  25                  30

Pro Glu Thr Glu Pro Pro Glu Met Leu Arg Asn Ser Thr Asp Thr Thr
            35                  40                  45

Pro Leu Thr Gly Pro Gly Thr Pro Glu Ser Thr Thr Val Glu Pro Ala
    50                  55                  60

Ala Arg Pro His Thr Cys Pro Pro Cys Pro Leu Gln Gln Arg Arg Gly
65              70                  75                  80

Leu Glu Ala Glu Arg Ala Arg Leu Ala Ala Gln Leu Asp Ala Leu Arg
                85                  90                  95

Ala Glu Val Ala Arg Leu Ala Arg Glu Arg Asp Leu Tyr Gly Gly Gly
            100                 105                 110

Gly Ala Gly Gly Gly Gly Lys Gly
        115                 120
```

<210> SEQ ID NO 38
<211> LENGTH: 101
<212> TYPE: PRT
<213> ORGANISM: Artificial Sequence
<220> FEATURE:
<223> OTHER INFORMATION: variant 1A mature and processed
<220> FEATURE:
<221> NAME/KEY: MOD_RES
<222> LOCATION: (5)..(5)
<223> OTHER INFORMATION: SULFATATION
<220> FEATURE:
<221> NAME/KEY: MOD_RES
<222> LOCATION: (7)..(7)
<223> OTHER INFORMATION: SULFATATION
<220> FEATURE:
<221> NAME/KEY: MOD_RES
<222> LOCATION: (10)..(10)
<223> OTHER INFORMATION: SULFATATION
<220> FEATURE:
<221> NAME/KEY: CARBOHYD
<222> LOCATION: (16)..(16)
<223> OTHER INFORMATION: Sialyl-Lewis -X (O-Glycan)
<220> FEATURE:
<221> NAME/KEY: MOD_RES
<222> LOCATION: (90)..(90)
<223> OTHER INFORMATION: SULFATATION
<220> FEATURE:
<221> NAME/KEY: MISC_FEATURE
<222> LOCATION: (100)..(100)
<223> OTHER INFORMATION: either Lys or Cys for conjugation

<400> SEQUENCE: 38

```
Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
                20                  25                  30

Gly Pro Gly Thr Pro Glu Ser Thr Thr Val Glu Pro Ala Ala Arg Pro
            35                  40                  45

His Thr Cys Pro Pro Cys Pro Leu Gln Gln Arg Arg Gly Leu Glu Ala
    50                  55                  60

Glu Arg Ala Arg Leu Ala Ala Gln Leu Asp Ala Leu Arg Ala Glu Val
65              70                  75                  80

Ala Arg Leu Ala Arg Glu Arg Asp Leu Tyr Gly Gly Gly Gly Ala Gly
                85                  90                  95

Gly Gly Gly Lys Gly
            100
```

```
<210> SEQ ID NO 39
<211> LENGTH: 44
<212> TYPE: PRT
<213> ORGANISM: Artificial Sequence
<220> FEATURE:
<223> OTHER INFORMATION: Chimeric PSGL-1-NRL protein
<220> FEATURE:
<221> NAME/KEY: MISC_FEATURE
<222> LOCATION: (1)..(1)
<223> OTHER INFORMATION: any aa or aa sequence (PSGL-1 aa 1-4)
<220> FEATURE:
<221> NAME/KEY: MISC_FEATURE
<222> LOCATION: (2)..(13)
<223> OTHER INFORMATION: PSGL-1 aa 5-16 (selectin binding region)
<220> FEATURE:
<221> NAME/KEY: MISC_FEATURE
<222> LOCATION: (14)..(14)
<223> OTHER INFORMATION: any aa or aa sequence (PSGL-1 aa 17-47)
<220> FEATURE:
<221> NAME/KEY: MISC_FEATURE
<222> LOCATION: (15)..(15)
<223> OTHER INFORMATION: covalent dimerization domain flanking region
<220> FEATURE:
<221> NAME/KEY: DISULFID
<222> LOCATION: (16)..(16)
<220> FEATURE:
<221> NAME/KEY: MISC_FEATURE
<222> LOCATION: (17)..(17)
<223> OTHER INFORMATION: covalent dimerization domain flanking region
<220> FEATURE:
<221> NAME/KEY: MISC_FEATURE
<222> LOCATION: (18)..(18)
<223> OTHER INFORMATION: any aa or aa sequence (from NRL aa 181-186)
<220> FEATURE:
<221> NAME/KEY: MISC_FEATURE
<222> LOCATION: (19)..(40)
<223> OTHER INFORMATION: NRL aa 187-208
<220> FEATURE:
<221> NAME/KEY: MISC_FEATURE
<222> LOCATION: (41)..(41)
<223> OTHER INFORMATION: any aa or aa sequence (from NRL aa 209-215)
<220> FEATURE:
<221> NAME/KEY: MISC_FEATURE
<222> LOCATION: (42)..(42)
<223> OTHER INFORMATION: spacer
<220> FEATURE:
<221> NAME/KEY: MISC_FEATURE
<222> LOCATION: (43)..(43)
<223> OTHER INFORMATION: Lys or Cys
<220> FEATURE:
<221> NAME/KEY: MISC_FEATURE
<222> LOCATION: (44)..(44)
<223> OTHER INFORMATION: any aa with exclusion of Cys or Lys, preferably
      Gly or Ala

<400> SEQUENCE: 39

Xaa Tyr Glu Tyr Leu Asp Tyr Asp Phe Leu Pro Glu Thr Xaa Xaa Cys
1               5                   10                  15

Xaa Xaa Leu Glu Ala Glu Arg Ala Arg Leu Ala Ala Gln Leu Asp Ala
            20                  25                  30

Leu Arg Ala Glu Val Ala Arg Leu Xaa Xaa Xaa Xaa
        35                  40
```

RECOMBINANT CHIMERIC PROTEIN FOR SELECTINS TARGETING

CROSS-REFERENCE TO RELATED APPLICATIONS

This application is the national stage application of corresponding international application number PCT/EP2017/052821, filed Feb. 9, 2017, which claims priority to and the benefit of European application no. 16154868.0, filed Feb. 9, 2016, all of which are hereby incorporated by reference in their entirety.

FIELD OF THE INVENTION

The present invention relates to the preparation of a novel Selectin targeting protein for diagnostic and therapeutic uses.

STATE OF THE ART

P-selectin glycoprotein ligand-1 (PSGL-1) is a leukocyte adhesion molecule that mediates cell tethering and rolling on activated endothelium cells under physiological blood flow. This activity is an important initial step in leukocyte extravasation. PSGL-1 was initially identified as a ligand for P-selectin, and subsequent work has revealed that PSGL-1 is also a ligand for E-selectin and L-selectin (see, e.g., U.S. Pat. No. 6,277,975).

Two members of the selectin family have particular relevance in the context of molecular imaging: P-selectin and E-selectin. Up-regulation or expression of P- and E-selectin on the vascular endothelium is known to occur under conditions of inflammation, while the presence of endothelial selectins under resting conditions is generally low to nil. Disease states in which selectins are useful molecular imaging targets include post-ischemic injury, acute coronary syndrome, arthritis, inflammatory bowel disease including ileitis and colitis, atherosclerosis, myocarditis, thrombosis and multiple sclerosis. However, selectin molecular imaging may be useful to delineate and identify tissues in which selectin expression occurs under normal conditions, such as the skin microvasculature.

Up-regulation of P-selectin (also called CD62P) is known to occur very rapidly (within minutes), making P-selectin a potential marker of early stages of inflammatory disease. P-selectin is also found on the surface of activated platelets, making it a marker of thrombosis. E-selectin (CD62E) is also expressed on inflamed vasculature, although generally later in the inflammatory response than P-selectin. E-selectin is thus a useful marker of inflammation at later stages of the disease.

Among selectins' ligands, PSGL-1 plays an important role in the recruitment of white blood cells into inflamed tissues. White blood cells normally do not interact with the endothelium of blood vessels. However, inflammation causes the expression of cell adhesion molecules (CAM) such as P-selectin on the surface of the blood vessel wall. White blood cells present in flowing blood can interact with CAM. The first step in this interaction process is carried out by PSGL-1 interacting with P-selectin and/or E-selectin on endothelial cells and adherent platelets. This interaction results in "rolling" of the white blood cell on the endothelial cell surface followed by stable adhesion and transmigration of the white blood cell into the inflamed tissue.

Human PSGL-1 (GenBank Acc. No Q14242.1; GI 2498904) is a mucin-like, homodimeric, disulfide-bonded, glycoprotein that is expressed on the surface of most hematopoietic cells, including, e.g., neutrophils, monocytes, lymphocytes, dendritic cells, and platelets.

The amino acid sequence of human PSGL-1 shows an amino terminal signal peptide (amino acid residues 1-17) and a propeptide (amino acid residues 18-41) with a consensus cleavage site for paired basic amino acid converting enzymes (PACE). The N-terminal extracellular region of the mature protein begins at residue 42. The extracellular domain of the PSGL-1 molecule contains several serine/threonine rich decameric repeats containing multiple O-glycosylation linkage sites and also some N-glycosylation linkage sites. This region of the molecule, which folds into a rod-like structure, is responsible for the mucin-like characteristics of PSGL-1. On neutrophils, this rod-like structure and the localization of PSGL-1 on the tips of microvilli facilitates the binding of PSGL-1 to selectin-expressing cells. The decameric repeat region of PSGL-1 is followed by the transmembrane region (residues 268-292) and the cytoplasmic domain (residues 293-361).

The expression of recombinant PSGL-1 first achieved by Sako et al. (Cell, 1993, 75(6), 1179-1186) has allowed to define regions and modifications relevant to selectins binding, which have been reported, just to mention some in: Liu et al J. Biol. Chem. 1998, 12:7078-7087, Cummings R D, Brazilian Journal of Medical and Biological research, 1999, 32:519-528, Sako et al. Cell, 1995, 83: 323-331 etc., cited ahead. From the overall studies on PSGL-1, regions important for selectins binding have been mapped in the N-terminal portion of the mature PSGL-1 and encompass residue 5-16 with the three tyrosine sulfation sites and the O-linked oligosaccharide bearing sLe$^x$ located at Thr 16.

The complex post-translational modification pattern of PSGL-1 (the protein requires two distinct post-translational modifications for the $Ca^{2+}$-dependent recognition by the lectin domain of P-selectin: tyrosine sulfation and a specific core 2 O-linked glycosylation by fucose and sialic acid) requires this molecule to be expressed in recombinant eukaryotic systems. Fugang Li et al. J. Biol. Chem, 1996, 271:3255-3264 describe the requirements for the recombinant expression of the correctly glycosylated form of rPSGL-1. U.S. Pat. Nos. 5,827,817 and 6,277,975 describe several variants of the PSGL-1 protein, among which the PSGL-1-Fc IgG1 fusion protein, and their expression in CHO and COS cells in combination with a fucosyl-transferase gene (FT). Thus, PSGL-1 chimerae with portions of the immunoglobulin Fc fragment have already been expressed either in CHO or COS carrying suitable enzyme(s) for correct glycosylation.

The same Applicant has already found that a shorter variant of such a PSGL-1 IgG1 Fc fusion protein, covalently bound to phospholipids of ultrasound imaging microvesicles, shows an improved binding to the target and increases microbubbles stability. These findings are disclosed in WO2012/020030 by the same Applicant of the present invention.

The present Application discloses the recombinant expression of a PSGL-1 chimeric protein which relies on a non-covalent dimerization domains for the production a homodimeric form of the PSGL-1 fusion protein, by which the use of antibody Fc fragments and the drawbacks of the presence of such fragments are avoided. In fact, the recombinant construct of the present invention exploits the use of functional fragments of DNA regulatory proteins, the "leucine zippers", which promote protein-protein interactions and homo- or hetero-dimers/multimers, form under which they act as Transcription Factors, able to interact with DNA and regulate its expression.

Leucine zippers are protein domains with leucine repetitions at every $7^{th}$ (sometimes $4^{th}$) amino acid position, able to form a right-handed α helix by which they promote oligomerization with identical or different counterpart(s), thus generating homo- or hetero-dimers/multimers and the DNA expression regulatory properties.

The use of leucine zippers as dimerization domains in *E. coli* has been exploited to produce dimeric antibodies or their functional fragments, ScFv, F(ab')2. The preparation of bi-functional ScFv in De Kruif, J. and Logtenberg T., J. Biol. Chem., 1996, 271:7630-7634.

GCN4, a yeast leucine zipper has been used in Chingwei V. Lee et al., J. Immunological Methods, 2004, 284: 119-132, for the phage display of F(ab')$_2$ fragments in the M13 system in *E. coli*.

WO2005/105840, dealing with recombinant CD40, proposes the use of so called "fusion partners", to induce oligomerization of CD40 variants in eukaryotic cells. Mannose Binding Protein, the collagen binding domain of tetranectin and leucine zippers, including the Neural Retina-specific Leucine zipper, NRL (GenBank Acc. N. M81840), are enlisted as possible fusion partners.

The Applicant has now found that when PSGL-1 functional fragments are cloned upstream of a NRL sequence, they are not only correctly processed and expressed as functional homodimers, but also expression and secretion occur very efficiently, much more than that observed for PSGL-1 Fc-derived constructs with the standard IgG backbone carrying the Hinge region and the Fc, commonly used for dimeric protein expression, which has become the reference standard of PSGL-1 homodimer expression.

The present invention allows now the preparation of a P/E Selectin specific reagent in suitable quantities and with a standard quality for in vivo use in either therapeutic or diagnostic applications.

The chimeric protein can be expressed at high levels in the CHO cell system, recognized with safe use properties for the production of recombinant proteins and which can provide the glycosylation and post-translational processing required for selectins binding. The high expression levels and the functional post-translational processing allow now the industrial scale-up of this reagent.

The fluorescent images were obtained two hours after liposome injection (left paw: inflamed paw; right paw: contralateral paw).

Figure 5:
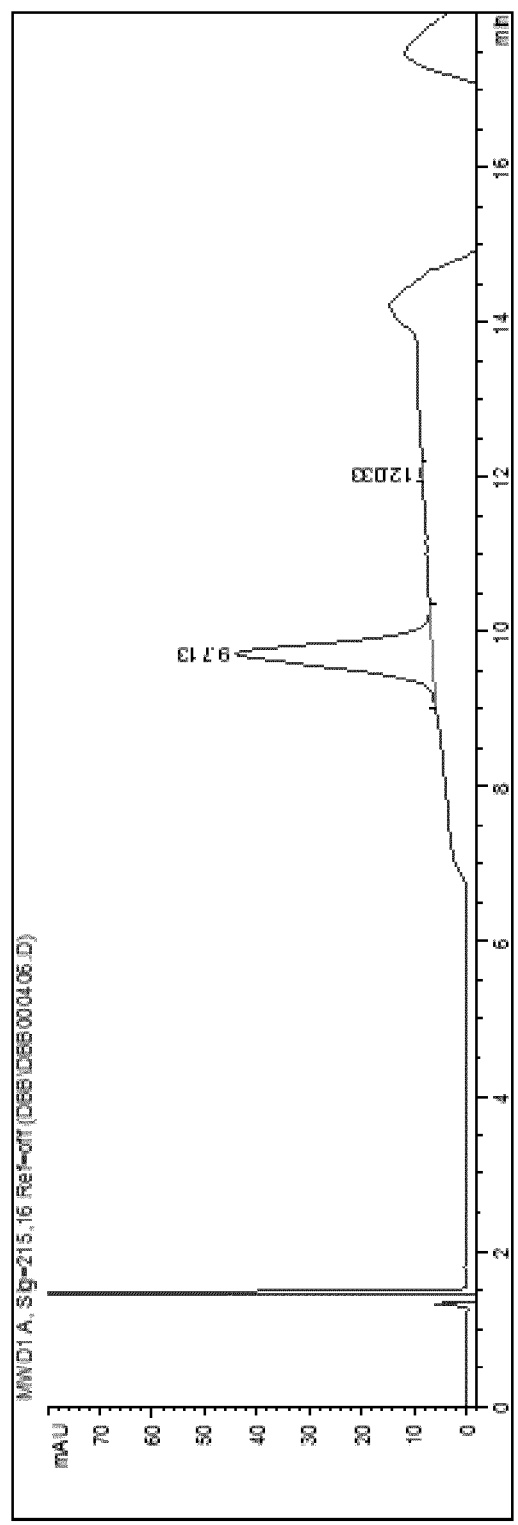

FIG. 5. RP-HPLC analysis of the final pool of fractions after HA purification described in Example 13 (negative). The Retention time (Rt) of the target protein is about 9.7 min.

SUMMARY OF THE INVENTION

The present invention disclose a recombinant chimeric P-Selectin Glycoprotein Ligand-1 (PSGL-1) protein comprising at least a selectin Binding domain, a leucine zipper domain and a disulfide bonds promoting region, where the selectin binding region preferably comprises at least aa 5-16 of SEQ ID NO:11.

The leucine zipper domain comprises an amino acid sequence at least 90% homologous or identical to aa 187-208 of SEQ ID NO:12 (Neural Retina-specific Leucine Zipper), or more preferably at least 90% homologous or identical to aa 181-215 of SEQ ID NO:12.

In the recombinant chimeric PSGL-1 protein of the invention, the disulfide bonds promoting region (covalent dimerization domain) comprises an amino acid sequence defined by the following general formula:

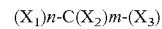

wherein:
- $X_1$, $X_2$ represents any amino acid or amino acid sequence with the exclusion of cysteine (Cys),
- C is Cys
- $X_3$ is any amino acid and
- n, m are integer numbers comprised from 1-6, or is preferably (SEQ ID NO:20).

The recombinant chimeric protein is a dimeric protein comprising two recombinant chimeric PSGL-1 monomers as defined above, covalently linked to each other by at least a disulfide bond and is preferably a homodimer.

It is expressed in a mammalian system where it is correctly post-translationally modified and secreted into the culture medium at high levels as a soluble dimer.

The invention further comprises the DNA sequence encoding for the recombinant chimeric protein as defined above and eukaryotic expression vectors driving its expression in a mammalian system, preferably CHO cells. The mammalian expression system further comprises the glycosylating enzymes beta 1,6 N-acetylglucosaminyltransferase (C2GnT) and fucosyl-transferase VII (FTVII) on a different or the same expression vector for proper glycosilation.

Accordingly, the invention further comprises the mammalian cell transformed with the DNA encoding for the chimeric recombinant PSGL-1 protein or the vector as defined above and the isolated purified protein secreted by the mammalian cell.

The isolated chimeric protein is homodimeric, O-linked glycosylated at least on Thr at position 16 and sulfated at least on Tyr at positions 5, 7 and 10 of SEQ ID NO:11.

The protein is a useful targeting agent for diagnostic or therapeutic moieties to which it can be conjugated by linker or spacer comprising the amino acid Cys or Lysine, preferably present and placed at the C-terminus.

Diagnostically useful moieties are preferably selected from the group consisting of: a radiolabel, an enzyme, a fluorescent label a luminescent label, a metal chelating compound, a gas-filled lipid microvesicle and combination of the diagnostically active moieties, and are more preferably metal chelating compounds or gas-filled microvesicles. These conjugates are useful for imaging by ultrasound, magnetic resonance, optoacoustic, scintigraphy, Single Photon Emission Computed Tomography (SPECT), Positron Emission Tomography (PET), X-Ray, radiofrequency acoustic and optical and in pathologic conditions characterized by overexpression of a selectin, such as: Acute Coronary Syndrome (ACS), Inflammatory Bowel Disease (IBD), Ulcerative colitis, Crohn's disease, neo-angiogenesis associated with tumors, rheumatoid arthritis, ischemia reperfusion injury, graft rejection or, more in general, of any organ or tissue expressing P-selectin and/or E-selectin above physiological levels. More preferably the pathologic condition is IBD, ACS, tumour detection or graft rejection.

More preferably, the chimeric protein of the invention is a useful targeting agent for IBD, ACS, tumour detection and graft rejection.

The therapeutically active moiety is preferably selected in the group consisting of: cytokine, cytostatic agent, toxin, anti-inflammatory agent, immunomodulator, antiaggregant, corticosteroid, monoclonal antibody, growth factor or radiotherapic agents comprising metal chelating moieties to carry a radionuclide.

Further comprised in the invention are pharmaceutical compositions comprising the recombinant chimeric protein or its conjugates for diagnostic or therapeutic purposes, as defined above.

A further embodiment of the invention is a process for preparing the recombinant chimeric protein of the invention which comprises transforming a eukaryotic cell with the DNA sequence encoding for it or the eukaryotic expression vector comprising said DNA sequence to achieve a recombinant system stably expressing the chimeric protein, harvesting the culture medium and purifying the recombinant protein from said culture medium.

The invention further relates to a purification process of the recombinant soluble protein, comprising hydroxyapatite as the last chromatographic step. Hydroxyapatite, preferably Ceramic Hydroxyapatite is preferably carried out after a strong anion exchange and a hydrophobic interaction chromatography.

Further embodiments of the invention are methods for the therapeutic treatment of a pathologic condition characterized by the overexpression of a selectin, using the targeting conjugates comprising the recombinant soluble chimeric protein according to the invention and the diagnostic imaging of a pathologic condition characterized by overexpression of a selectin, which comprises pre-administering the diagnostic conjugates or the pharmaceutical compositions to a subject and recording the image by an imaging method. Such imaging methods are preferably selected in the group consisting of: ultrasound, magnetic resonance, optoacoustic, scintigraphy, Single Photon Emission Computed Tomography (SPECT), Positron Emission Tomography (PET), X-Ray, radiofrequency acoustic and optical.

Pathologic conditions characterized by overexpression of a selectin are preferably selected in the group consisting of: Acute Coronary Syndrome (ACS), Inflammatory Bowel Disease (IBD), Ulcerative colitis, Crohn's disease, neo-angiogenesis associated with tumors, rheumatoid arthritis, ischemia reperfusion injury, graft rejection or, more in general, of any organ or tissue expressing P-selectin and/or E-selectin above physiological levels. More preferably the pathologic condition is IBD, ACS, cancer or graft rejection.

DETAILED DESCRIPTION OF THE INVENTION

Definitions

Unless otherwise provided, the amino acid and nucleotide sequence of the human PSGL-1 to which the present invention refers, is identified by GenBank Acc. N° Q14242.1. This Acc. Number identifies also functional domains, such as the signal peptide region of PSGL-1, comprised from aa 1-17, the pro-peptide region comprised from aa 18 to 41, which identifies the start of the mature protein at aa 42 (corresponding to aa 1 of SEQ ID NO:11), the N- and O-glycosylation sites and the sulfation sites.

The neural Retina-specific leucine zipper (NRL) amino acid sequence is identified by NCBI Acc. No NP_006168.1 (GI:1709348, human). In the present invention reference to Neural Retina-specific Leucine zipper protein (NRL) comprises all amino acid sequences at least 90% homologous in the leucine zipper region of NRL, including mouse NRL (P54846).

NRL, first isolated and characterized by Swaroop et al. Proc. Natl. Acad. Sci., 1992, 89: 266-270, single Nucleotide Polymorphisms have been identified: they are comprised, if functional, in the present invention; in the NP_006168.1 sequence, the Leucine Zipper domain has been identified between amino acids 187-208. Flanking amino acids at the N-term or the C-term of this region, derived from the NRL sequence, may also be part of the functional domain (non-covalent dimerization motif).

As used herein, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, transfected cell, polypeptide or polynucleotide includes such molecules, constructs, vectors, cells, polypeptides or polynucleotides even if they have a partial sequence identical to the naturally occurring molecule.

The term "polypeptide" is used to refer to a compound of two or more amino acids joined through the main chain (as opposed to side chain) by a peptide amide bond (—C(:O)NH—). The term "peptide" is used interchangeably herein with "polypeptide" but is generally used to refer to polypeptides having fewer than 40, and preferably fewer than 25 amino acids.

The term "protein" is used to refer to a compound of more than 40 amino acids joined through the main chain (as opposed to side chain) by a peptide amide bond (—C(:O)NH—).

The term "chimeric protein" or "fusion protein" or "chimera" as used in the present invention comprises a PSGL-1 polypeptide operatively linked to at least one non-PSGL-1 polypeptide. A "PSGL-1 polypeptide" shares the amino acid sequence of PSGL-1, preferably human, whereas the "non-PSGL-1 polypeptide" has an amino acid sequence which is not substantially homologous to PSGL-1 and which is derived from the same or different organism. In a preferred embodiment, the "PSGL-1 polypeptide" comprises the extracellular portion of PSGL-1, or shorter fragments thereof, still binding selectins (in particular P and E selectin), such as the 1-47 fragment of PSGL-1 (SEQ ID NO:11) encompassing aa 5-16, region which defines the selectin binding region. The selectin binding region may optionally comprise flanking amino acid(s) at the N- or C-terminus of aa 5-16 derived from the PSGL-1 sequence.

The "fusion" or "chimeric protein" is expressed and produced in a recombinant system by operatively linking the DNA sequence encoding the PSGL-1 polypeptide to the DNA sequence encoding the non-PSGL-1 polypeptide fused in frame to each other under the control of regulatory regions of eukaryotic expression, such as a promoter or a polyadenylation site.

The term "binding" refers to the determination by standard assays, including those described herein, that a binding polypeptide recognizes and binds reversibly to a given target. Such standard assays include, but are not limited to, equilibrium dialysis, gel filtration, surface plasmon resonance, immuno affinity assays, including competitive immunoassays and the monitoring of spectroscopic changes that result from binding.

A "labeling group" or "detectable label," as used herein, is a group or moiety capable of generating a detectable signal. Particularly preferred are labels useful for diagnostic imaging, i.e. labels detectable by magnetic resonance, radioactive detection, ultrasound, X-ray, light (either UV, infrared, fluorescent, etc.) or carrying a moiety, such as a radioactive metal or other entity, that may be used in radiotherapy or other forms of therapy. Specific labels will be detailed in the following.

The term "specificity" refers to a binding polypeptide having a higher binding affinity for one target over another. Binding specificity may be characterized by a dissociation equilibrium constant ($K_D$) or an association equilibrium constant ($K_a$) for the two tested target materials. In a preferred embodiment, binding polypeptides of the invention have a dissociation constant for a desired target that is lower than about 10 µM, more preferably lower than about 1 µM, and most preferably less than about 0.5 µM or even lower. The term "selectin specificity" refers to a PSGL-1 binding moiety having a higher affinity for at least one selectin among P, L, E selectin than an irrelevant target.

The term "patient" as used herein refers to any mammal, especially humans.

The term "pharmaceutically acceptable" carrier or excipient refers to a non-toxic carrier or excipient that may be administered to a patient, together with a compound of this invention, and which does not destroy the pharmacological activity thereof.

The term "target" or "target molecule" refers to any substance that a binding moiety or binding polypeptide can bind to, such as proteins or polypeptides, cells, receptors, carbohydrates, lipids, etc. As used herein, "target" includes the family of Selectins either in the isolated form or expressed in or on the surface of a cell, tissue or organ. Accordingly, "targeting" moiety as used herein, refers to a PSGL-1 protein or functional fragments thereof capable of binding to selectins, preferably P and E-selectins, if not specified differently.

The terms "therapeutic agent" or "therapeutic" refer to a compound or an agent having a beneficial, therapeutic or cytotoxic effect for i.e. malignant cells in vivo. Therapeutic agents include those compositions referred to as, for example, bioactive agents, cytotoxic agents, drugs, chemotherapy agents, radiotherapeutic agents, genetic material, etc.

The term "positively charged" amino acid refers to amino acids in the following group: Arginine, Histidine, Lysine. These amino acids are usually considered as "interchangeable" meaning that substitution of a residue with another in the same group is usually well tolerated within a protein or polypeptide, even if this may not apply when the residue is comprised in a critical domain of the protein (such as a alpha-helix, a binding pocket, a sterically-dependent constraint etc.)

The term "negatively charged" amino acid refers to amino acids in the following group: aspartic acid and glutamic acid. These amino acid are usually considered as "interchangeable" meaning that the substitution of a residue with another in the same group is usually well tolerated within a protein or polypeptide, even if this may not apply when the residue is comprised in a critical domain of the protein (such as a binding pocket or a sterically-dependent region constraint, etc.)

The term amino acid with "polar uncharged side chain" refers to amino acids in the following group: Serine, Threonine, Asparagine and Glutamine. These amino acids are usually considered as "interchangeable" meaning that the substitution of a residue with another in the same group is usually well tolerated within a protein or polypeptide, with the above mentioned exemplary exceptions.

The term amino acid with "hydrophobic side chain" refers to amino acids in the following group: Alanine, Valine, Isoleucine, Leucine, Methionine, Phenylalanine, Tyrosine and Tryptophan. These amino acids are usually considered as "interchangeable" meaning that the substitution of a residue with another in the same group is usually well tolerated within a protein or polypeptide, even if this may not apply when the residue is comprised in a critical domain of the protein (such as a alpha-helix, a binding pocket, a sterically-dependent constraint etc.).

Amino acids with specific functions in the protein are those comprised in the following group: Cysteine, Glycine and Proline. Depending on whether the function is performed due to the size of the residue, glycine may be replaced by other small sized residues, such as Serine or Alanine. At variance, Cysteine may not be replaced when involved in a disulfide bridge.

By covalent dimerization domain, the Applicant refers to a sequence of amino acids comprising a Cysteine which can be engaged in a disulfide bridge with another cysteine on a different polypeptide chain (extra-chain disulfide bridge), stable in the extracellular environment.

By non-covalent dimerization domain the Applicant refers to a sequence of amino acids able to determine and/or favor protein-protein interactions. Preferred non-covalent dimerization domains are structural alpha-helix, determined by periodic repetition of leucine residues, usually referred to in the art as "leucine zippers".

Leucine zipper amino acid regions which can be used according to the invention, are preferably devoid of any lysine (K or Lys). Leucine zipper domain are usually easily identified in eukaryotic "regulatory" proteins, by a periodic repetition of the aa leucine. Among them, i.e. the leucine zipper of Q9Y2D1, corresponding to aa 236-250, or the leucine zipper of the Activating transcription factor 5 (GI: 114678546).

However, preferred leucine zippers according to the present invention are selected in the group consisting of:

a Neural Retina-specific Leucine zipper protein fragment, isolated from mammals and sharing a homology degree ≥90% with fragment 187-208 of the human NRL protein, even more preferably the leucine zipper domains of mouse NRL (Q543Y0) or human NRL, isophorm 2 (P54845-2) or bovine protein F1N4J1.

Detailed Description

The invention refers to a recombinant PSGL-1 chimeric protein comprising a Selectin Binding domain and a non-covalent dimerization domain, which is a leucine zipper and is more preferably the leucine zipper domain of the human or mouse Neural Retina-specific Leucine Zipper, preferably corresponding to at least region 187-208 of NP_006168.1 (SEQ ID NO: 12), or more preferably, at least region 181-215 of SEQ ID NO:12. Alternatively, the non-covalent dimerization domain shares a homology degree z 90% with fragment 187-208 of the human NRL protein, even more preferably is the leucine zipper domains of mouse NRL (Q543Y0) or human NRL, isophorm 2 (P54845-2) or bovine protein F1N4J1.

By P-selectin Binding Domains, we herein refer to peptides or polypeptides comprising an amino acid sequence with binding affinity for selectins ("active sequences"), particularly for P-selectin; said active sequences comprise at least amino acids 5-16 (Cummings R D, Brazilian Journal of Medical and Biological research, 1999, 32:519-528) or are preferably selected among fragments 1-19, 5-41 and 1-47 of SEQ ID NO: 11 where amino acid 1 represents the first amino acid of the mature PSGL-1 protein and corresponds to aa 42 of the GenBank record Acc. N. Q14242.1.

The PSGL-1 protein is a transmembrane homodimer linked by a disulfide bond at Cys 320, close to the transmembrane domain, as defined in the GenBank record.

Up to now, dimerization of recombinant PSGL-1 has been achieved by introducing the IgG1 Fc domain downstream a PSGL-1 selectin-binding domain. The Fc domain comprises a Hinge region carrying at least two cysteines, engaged in disulfide bridges to covalently associate the chimeric protein in homodimers. The immunoglobulin Fc region has been used in several recombinant systems to improve or to facilitate dimerization that is essential for selectins binding.

However, the presence of the Fc domain presents some drawbacks. First, it was demonstrated that the PSGL-1 fused to a Fc domain, bound at the surface of the gas microvesicles elicits the formation of aggregates (WO2012/020030). Moreover, the Fc domain might also trigger immune reaction, through specific recognition of Fc-Receptor expressed by macrophages. This could lead either to the clearance of the molecule carrying the Fc protein fragment from the blood circulation, or trigger an immune response such as allergic reactions.

As a matter of fact, the same Applicant of the present invention has found that a shorter Fc region provides improved properties to the derivatives used for microbubble preparation. Such drawbacks have been overcome by the present invention, wherein the Leucine zipper domain of human NRL replaces the Fc region. This region is preferably the leucine zipper domain of Neural Retina-specific Leucine Zipper, comprising at least aa 187-208 of NP_006168.1 or preferably aa 186-209, 185-210, 184-211, 183-212, 182-213, 181-214, 181-215, 186-208, 186-210, 187-208 or any fragment comprising at least aa 187-208 plus additional 1, 2, 3, 4, 5, 6 or 7 flanking amino acids at the N- or C-terminus or both, from region 181-215 of the sequence NP_006168.1 (SEQ ID NO:12).

The Applicant has found that the leucine zipper domain of the DNA regulatory proteins NRL, not only allows an efficient covalent dimerization of the chimeric monomer by favouring disulfide bridge formation, but also provides for a very efficient expression and secretion of the dimeric functional protein in mammalian recombinant systems.

Even more surprisingly, this new chimeric protein is correctly post-translationally modified, i.e. is correctly 0-glycosylated and sulfated at Tyr in the expected PSGL-1 region, is dimeric and covalently bound by disulfide bridge(s) and binds selectin targets with an affinity superior or at least equivalent to optimized Fragment 1 (Fr-1), described in WO2012/020030. These conclusions have been obtained by a number of data which have been better detailed in the experimental part.

The above findings are quite surprising since the present chimeric protein (P-selectin glycoprotein ligand-1 and Neural Retina-specific Leucine Zipper), herein named sPSGL-1-NRL, is the combination of domains from unrelated proteins and is even more peculiar when compared to the expression levels of other chimeric proteins engineered to carry the PSGL-1 selectin binding domain as the N-terminal region, fused in frame with other dimerization domains commonly used in the art, such as the IgG1 Fc fragment.

Specifically, in one of the preferred embodiments of the invention, the PSGL-1 domain 1-47 of SEQ ID NO:11 has been fused in frame with:
  a covalent dimerization domain, comprising at least a cysteine as below defined, preferably followed or alternatively preceded and fused in frame with a non-covalent dimerization domain (or stabilization domain), such as the NRL leucine zipper, instead of the Fc or CH3 domain of human IgG1;
  optionally and preferably a spacer at the C-terminus, to avoid any sterical hindrance with groups or moieties which are to be linked at the C-term, and
  a signal peptide for secretion at the N-terminus of the chimeric protein, which is suitable to be cleaved off in the mature chimeric protein and which is preferably not the endogenous PSGL-1 signal and pro-peptide sequence.

Among the several Variants that have been produced and tested for expression in a mammalian system: Variant 1 and 1A representing preferred embodiments of the present PSGL-1-NRL chimeric protein invention (SEQ ID NO:2 and SEQ ID NO:37), Variant 2 (SEQ ID NO:4), which corresponds to the PSGL-1 fused in frame with the human IgG1 Hinge and CH3 domain, used respectively as a covalent and non-covalent dimerization (or stabilization) domains, or Variant 5 (SEQ ID NO:10), comprising the same functional domains of the optimized Fragment 1 described in WO2012/020030 prepared for comparative purposes. Of note, in the protein variants of interest, the sequence listings mentioned above identify a signal peptide which is cleaved off in the expressed mature form.

In particular, it has been observed that only the NRL leucine zipper containing Variant 1, provides expression levels which are suitable for the production of a pharmaceutical agent. Comparative data of the relative expression of Variants 1-5, expressed in the same cell-system, is given in FIG. 1, where the expression level of tagged chimeric proteins has been evaluated by transient expression, SDS-PAGE in denaturing and non-denaturing conditions and Western-blot with an antibody directed to a common tag (i.e. the FLAG octapeptide) placed at the C-terminus.

Therefore, without being linked to a particular theory, it is believed that the presence of a non-covalent dimerization domain such as a leucine zipper and more preferably the leucine zipper of NRL which favours protein-protein interaction, in a protein which is physiologically a dimer (the PSGL-1), results, by either a favourable folding or a stabilization effect of the final chimeric protein of the present invention, in improved expression levels, which can be further optimized by single clone isolation and stabilization in culture. Titers provided after a preliminary clonal selection are well above 0.1 g/L.

In the chimeric protein of the present invention, the covalent dimerization domain, alternatively called disulfide bond(s) promoting region, comprises at least one Cys residue available to form a disulfide bond with another Cys in a monomeric chimeric protein counterpart, so that the two chimeric protein monomers are covalently bound through at least one disulfide bridge.

A general formula encompassing the covalent dimerization domain is:

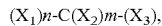

$(X_1)n$-$C(X_2)m$-$(X_3)$,

Wherein $X_1$ and $X_2$ represent any amino acid or amino acid sequence with the exclusion of Cys; C is cysteine, $X_3$ is any amino acid and n and m are integer numbers comprised from 1-6. $X_1$ preferably comprises a Proline, Histidine or Threonine. $X_1$ even more preferably comprises a Proline and a Histidine or a Histidine and a Threonine or a Proline and a Threonine. According to a preferred embodiment, $X_1$ comprises a Proline, a Histidine and a Threonine, preferably in this order, and n is at most 5. $X_2$ is any amino acid or amino acid sequence with the exclusion of Cys and preferably comprises Proline. Preferably $X_2$ is Pro-Pro; $X_3$ is preferably Cysteine and comprises at least a Proline. More preferably, the cysteine carrying region is the IgG1 Hinge region, or functional fragments thereof. A preferred disulfide bonds promoting region is: PHTCPPCP (SEQ ID NO:20).

According to a preferred embodiment, the chimeric protein further comprises a spacer at the C-term, which comprises a residue suitable for covalent bio-conjugation with other peptide or chemical moieties, such as imaging and/or therapeutic moieties. Exemplary amino acids for bio-conjugation are cysteine and lysine. The spacer is about 4-20 amino acids in length and comprises one or more amino acid selected from the group consisting of: Gly, Ser, Pro, Ala, Val, Leu; it carries a cysteine or a lysine at its C-terminus, preferably in the penultimate position. The spacer is preferably a poly-glycine embedding an alanine or other neutral amino acid, such as valine or similar and it carries a cysteine or a lysine, preferably a lysine, wherein said conjugation amino acid is followed by Gly, Ser, Pro, Ala, Val, Leu, preferably at least one Gly. The spacer has preferably sequence $G_4AG_4KG$ (SEQ ID NO:17). Alternatively, the chimeric protein comprises a Flag sequence at its C-terminus, i.e. for identification and purification purposes. Flag sequences are commonly used by the skilled artisan and known in the field. One example is the DYDDDDK sequence (SEQ ID NO:35), which allows protein recognition and/or purification by immuno-affinity with suitable antibodies.

According to a preferred embodiment, the monomeric protein is translated as a precursor with the signal peptide and is then processed and finally secreted into the culture medium (conditioned medium) as a homodimer after cleavage of the signal peptide.

A signal peptide for secretion is present at the N-terminus of the precursor of the chimeric protein. Preferably, the signal peptide is the mouse IgH signal peptide, which has sequence: MEWSWWVFLFFFLSVTTGVHS (SEQ ID NO:18). Other signal peptides (or leader peptides) may be used, such as the PSGL-1 endogenous signal peptide sequence or other heterologous signal peptides sequences commonly used in the art of recombinant protein expression, allowing secretion of post-translationally processed recombinant proteins. An example of some signal (or leader) peptides known in the field has been provided in Table 1.

TABLE 1

Leader signal peptide sequences.

| Acc. N | Name | Gene | Specie | Sequence |
|---|---|---|---|---|
| P01728 | LV2A_MOUSE | Ig lambda-2 chain V region | Mus musculus | MAWTSLILSLLALCSGASS SEQ ID NO: 21 |
| P01758 | HVM14_MOUSE | Ig heavy chain V region 108A | Mus musculus | MGWSWIFLFLLSGTAGVHS SEQ ID NO: 22 |
| P01750 | HVM06_MOUSE | Ig heavy chain V region 102 | Mus musculus | MGWSCIILFLVATATGVHS SEQ ID NO: 23 |
| P01749 | HVM05_MOUSE | Ig heavy chain V region 3 | Mus musculus | MGWSCIILFLVATATGVHS SEQ ID NO: 24 |
| P01821 | HVM45_MOUSE | Ig heavy chain V region MC101 | Mus musculus | MAVLGLLFCLVTFPSCVLS SEQ ID NO: 25 |
| P01748 | HVM04_MOUSE | Ig heavy chain V region 23 | Mus musculus | MGWSCIILFLVAAANGVHS SEQ ID NO: 26 |
| Q61508 | ECM1_MOUSE | Extracellular matrix protein 1 | Mus musculus | MGTVSRAALILACLALASA SEQ ID NO: 27 |
| P01751 | HVM07_MOUSE | Ig heavy chain V region B1-8/186-2 | Mus musculus | MGWSCIMLFLAATATGVHS SEQ ID NO: 28 |
| P01831 | THY1_MOUSE | Thy-1 membrane glycoprotein | Mus musculus | MNPAISVALLLSVLQVSRG SEQ ID NO: 29 |
| Q03402 | CRIS3_MOUSE | Cysteine-rich secretory protein 3 | Mus musculus | MALMLVLFFLAAVLPPSLL SEQ ID NO: 30 |
| P01746 | HVM02_MOUSE | Ig heavy chain V region 93G7 | Mus musculus | MGWSFIFLFLLSVTAGVHS SEQ ID NO: 31 |
| P26262 | KLKB1_MOUSE | Plasma kallikrein | Mus musculus | MILFNRVGYFVSLFATVSC SEQ ID NO: 32 |
| P11627 | L1CAM_MOUSE | Neural cell adhesion molecule L1 | Mus musculus | MVVMLRYVWPLLLCSPCLL SEQ ID NO: 33 |

TABLE 1-continued

Leader signal peptide sequences.

| Acc. N | Name | Gene | Specie | Sequence |
|---|---|---|---|---|
| P06327 | HVM52_MOUSE | Ig heavy chain V region VH558 A1/A4 | Mus musculus | MGWRWIFLFLLSGTAGVHC SEQ ID NO: 34 |

As an alternative to SEQ ID NO:18 any of the above signal peptides from SEQ ID NO:24 to SEQ ID NO:34 may be used to achieve secretion of the recombinant protein.

The PSGL-1-NRL chimeric recombinant protein of the present invention binds efficiently P/E selectin in a dimeric form where each monomer is the recombinant PSGL-1 as defined above and is produced in a properly glycosylated and sulfated form. Several studies published until now, have reviewed the PSGL-1 post-translational requirements for P/E/L selectin binding i.e. the glycosylation, sulfation, and mapped the residues important for this processing and for selectin binding (R. D Cumming, Braz. J. Biol. Res., 1999, 32(5): 520-528 and D. Sako Cell, 1995, 83: 323-331).

In the preferred embodiment of the chimeric protein according to the present invention, sialylation (presence of sialic acid) has been evaluated by Liquid Chromatography coupled to Mass Spectrometry (LC-MS) after a mild acidic treatment. The content of sialyl residues of the recombinant proteins of the invention can be comprised from about 5% to 30% w/w, 10% to 28% w/w, 15% to 25% w/w more preferably 15% to 25%.

In order to characterize the recombinant chimeric protein, peptide mapping has been carried out with Asp-N and Chymotrypsin enzymatic digestion.

N-terminal glutamine (Gln) cyclization to pyroglutamine (pGlu), Tyr sulfation, Thr O-glycosylation (presence of Core 2 SLe$^x$) and dimeric structure have been also assessed and better detailed in the experimental part.

The dimeric structure of the proteins has been confirmed by chymotrypsin cleavage, which provides a (TCPPCPL)$_2$ fragment according to a preferred embodiment of the recombinant protein.

Sulfation of N-terminal tyrosine (Y) residues 5, 7 and 10 has been confirmed by Asp-N digestion. O-glycosilation with a SLe$^x$ tetrasaccharide motif has been confirmed on threonine 16 by chymotrypsin cleavage.

From all of the above it can be concluded that, in the chimeric proteins the N-terminal domain of PSGL-1 important for Selectin binding, is properly sulfated at Tyr residues corresponding to position 5, 7 and 10 of the mature PSGL-1 protein, and glycosylated, in particular O-linked glycosylated at threonine residue in position 16; O-linked glycans typically comprise sugar residues such as N-acetylgalactosamine (GalNac), N-acetylglucosamine (GlcNAc), fucose, glucose, galactose, mannose (Man), hexose, xylose, sialic acid or mixtures thereof.

These post-translational modifications (PTM) have been summarized in SEQ ID NO:38.

The O-linked glycans preferably present on the PSGL-1 portion of the chimeric protein of the present invention are preferably GalNac, GlcNAc, fucose, sialic acid and galactose. O-linked glycans on PSGL-1 are preferably sialylated and fucosylated and preferably consist of sialyl Lewis X glycan structure (sLe$^x$, sialic acid-galactopyranosyl-fucose-N-acetylglucosamine) bound to threonine residues.

This type of post-translational modification has been described as essential for P-selectin binding (R. D Cumming, Braz. J. Biol. Res., 1999, 32(5): 520-528 and D. Sako Cell, 1995, 83: 323-331).

Dimers are formed and each monomer is covalently linked by at least one disulfide bridge to the other.

Correct post-translational processing of the chimeric proteins has been achieved by expression in mammalian cells such as HEK-293, COS-1 or CHO cells, which have been used in the past for PSGL-1 expression. In any case, PSGL-1 is preferably co-expressed in mammalian cells together with C2GnT (core 2 β1-6-N acetylglucosaminyltransferase) and either a fucosyl-transferase enzyme such as one of the following: Fuc-TIII (Fuc-T: fucosyltransferase), Fuc-IV or Fuc TVII (Fugang Li et al. J. Biol. Chem, 1996, 271:3255-3264) or their functional fragments. Preferably, Fuc TVII or functional fragments thereof are used. Cells, preferably CHO adapted to suspension growth, are allowed to grow for at least 7 days, usually up to 14 days, using OptiCHO™ (LifeTechnology) medium (other serum-free chemically defined media can be successfully used, e.g., ActiCHO™ by GE/PAA, FortiCHO™, CellVento™ CHO 200 and CellVento™ CHO 220 by Millipore, 83836C by SAFC, BalanCD™ by Irvine, EX-CELL® by Sigma-Aldrich and the like) and in the absence of selection pressure. Glutamine (or the analogue GlutMax™) was supplemented at 1-10 mM, preferably 4-8 mM. OptiCHO™ and ActiCHO™ (LifeTechnology) are preferred for expression purposes.

The chimeric protein can be purified to the required purity level by a three steps chromatography comprising: an anion-exchange, a hydrophobic interaction and size-exclusion or hydroxyapatite (HA) chromatography. Purification comprising a HA column as the last purification step is preferred and provides a therapeutic grade pure chimeric protein.

Therefore according to a further embodiment, the present invention comprises a purification process for the chimeric protein as above defined, comprising as the final step a hydroxyapatite (HA) chromatography. More preferably, the purification process comprises a first chromatography carried out on a strong anion exchange (AE), a second chromatography carried out on a hydrophobic interaction (HI) solid phase and a third step carried out on HA, preferably Ceramic hydroxyapatite.

More generally, the present invention refers to a process for the purification of any soluble PSGL-1-containing fusion or chimeric protein, wherein said PSGL-1 comprises at least aa 5-16 of the mature PSGL-1 (SEQ ID NO:11), further comprising one or more flanking amino acid at the N- or C-term of such 5-16 fragment.

More preferably, the PSGL-1 fragment in the chimeric protein comprises all flanking amino acids up to at least aa 1-47 of the mature PSGL-1. Even more preferably, the chimeric protein further comprises at least aa 187-208 of SEQ ID NO:12 (Neural Retina-specific Leucine Zipper) or an amino acid sequence at least 90% homologous or identical to said 187-208 region and a covalent dimerization domain as above defined by the general formula. A general embodiment for the chimeric protein has SEQ ID NO:39.

However, the purification process of the invention comprising HA as the last step can be successfully applied to any chimeric or recombinant protein carrying at the N-terminus, the N-terminal region of mature PSGL-1 comprising at least aa 5-16 or 1-47 of PSGL-1.

The process comprising HA as the last purification step allows to achieve purity of the PSGL-1 higher than 95%, preferably 96%, 97%, 98% or 99% from other proteins and substantially free of contaminating DNA, as measured i.e.

by commercial DNA quantitation assays, such as the DNA Quantitation Kit, Fluorescence Assay (Sigma).

As for the final yields, the target protein is recovered by the process described above with yields above 50% of the total chimeric target protein content, typically above 60% and generally about or above 70%. These yields represent a good result and, most importantly for an industrial process, they are quite standardized and reproducible with very low variations.

Standard commercial resins or columns with these features may be used according to the manufacturer's instruction. Ceramic HA is commercially available i.e. from BIO-RAD. Purification and elution conditions may be adjusted as known to the skilled man.

For ease of scale-up, the gradient elution can be advantageously substituted with discrete step elution, in order to limit the number of in-process analyses and reduce the overall process time. The purified protein (purity z 90%), in the preferred embodiments of Variant 1 and 1A described below, was characterized and:

- The correct removal of the leader peptide was confirmed;
- The N-term structure of the PSGL Variant 1A glycoprotein is mainly in the pyroglutamic form pQATEYEYL. In fact, the use of Asp N digestion enzyme allowed detecting N-term Gln cyclization, the process by which the Gln residue present at the N-term, tend to undergo spontaneous cyclization to form pyroglutamic acid;
- The dimeric character of the PSGL Variant 1A has been confirmed by gel electrophoresis in reducing and non-reducing conditions and enzymatic digestion followed by fragment characterization using LC-MS. Experimental data shows that PSGL Variant-1A could be entirely under its dimeric form;
- The presence of the O-glycan moiety on Thr16 has been confirmed and its structure identified. The expected Sialyl-Lewis-X motif, a Core 2 structure comprising N-Acetylgalactosamine, N-Acetylglucosamine, galactose, fucose and sialic acid has been demonstrated, as better detailed in the experimental part;
- Sulfation of residues Y5, Y7 and Y10 of the mature protein important for binding to both L- and P-selectin has been also confirmed. Monitoring of glycoprotein sulfation was performed by mass spectrometry. As known by the skilled man, sulfation of Tyrosines 5, 7 and 10, demonstrated in the present target chimeric protein is extremely important for PSGL-1 and Variant 1A bioactivity.

Additional protein characterization data have been reported in the present Application and better detailed in the experimental part.

Therefore, according to the main aspect, the invention refers to an isolated and purified PSGL-1 chimeric protein, as above defined, able to bind P, L and E selectins, preferably P selectin.

The isolated recombinant protein is a homodimer wherein each homodimer has a primary sequence comprising or preferably consisting, of the following amino acid sequences, more preferably in this order:

- amino acid 1-47 of mature PSGL-1 protein (SEQ ID NO:11) at the N-terminus;
- at least an amino acid sequence comprising or consisting of a cysteine suitable for a disulfide bridge with formula: $(X_1)n-C(X_2)m-(X_3)$, as defined above, more preferably SEQ ID NO:20;
- at least aa 181-215 of the NRL (SEQ ID NO:12);
- optionally, an amino acid spacer up to 15 aa long, carrying: at least one or more Gly and/or Ala and preferably an amino acid such as Lys or Cys at the C-terminus or, more preferably, in the penultimate position. More preferably such a spacer is a poly-glycine, made of 4, 5, 6, 7, 8, 9 or 10 glycines preferably comprising and embedding at least an alanine, more preferably further comprising a lysine in the penultimate position for further chemical conjugation. Even more preferably the amino acid spacer is SEQ ID NO:17. Therefore, in a particularly preferred embodiment, the chimeric protein has sequence SEQ ID NO:37, where the signal peptide, cleaved off in the mature protein, is still represented. A post-translationally modified, chimeric target protein monomer is represented in SEQ ID NO:38 as a preferred embodiment.

A general formula of the chimeric variant protein with motifs or regions essential for:

- selectin binding, as thoroughly defined above,
- covalent dimerization (namely a Cys comprising motif with flanking regions),
- non-covalent dimerization (namely a motif comprising at least NRL aa 187-208), preferably comprising residue(s) for conjugating the chimeric protein, preferably in ultimate or penultimate position (namely Lys or Cys) has been also reported in SEQ ID NO:39.

Purity of the isolated and purified PSGL-1 chimeric protein can be determined by UPLC-UV or Surface Plasmon Resonance on, i.e., a Biacore apparatus as better detailed in the Experimental Part.

The present invention also refers to any DNA sequence encoding the above protein in the monomeric form, preferably comprising the nucleotide sequence encoding for amino acid 1-118 of SEQ ID NO:2 of the chimeric protein as defined above. According to a particularly preferred embodiment the nucleotide sequence encompasses nt 1-354 of SEQ ID NO:36 and preferably consists of nucleotide 1-360.

Alternatively, the DNA sequence encoding the chimeric protein of the present invention comprises at least the nucleotide sequence encoding the P-selectin Binding domain of PSGL-1, preferably aa 1-47 of SEQ ID NO:11 and the nucleotide sequence encoding at least aa 187-208 of the Neural Retina-specific Leucine zipper domain (SEQ ID NO:12), optionally comprising 1, 2, 3, 4, 5, 6 flanking amino acids at the N- or C-terminus, or, more preferably, encoding at least aa 181-215 of the NRL (SEQ ID NO:12).

The redundancy of the genetic code allows different codons to be used for a single amino acid, thus different combinations of codons, i.e. different DNA sequences, allow to express the protein with the same primary amino acid sequence and to produce the same recombinant protein. Such different DNA sequences, which may be designed to optimize expression in the selected recombinant system by using preferential codons for each organism, are therefore all comprised within the scope of the present invention.

A particularly preferred recombinant chimeric protein encompasses aa 1-118 of SEQ ID NO:2, encoded by nt 1-354 of SEQ ID NO:1. Amino acids 1-118 of SEQ ID NO:2 optionally further comprise at the C-terminus at least an amino acid suitable for chemical conjugation with reactive groups of a labelling or therapeutic moieties, wherein said amino acid is Lysine or Cysteine. More preferably, such reactive amino acid is followed by at least another non-charged amino acid, preferably Glycine. Even more preferably, the amino acid suitable for conjugation is placed at the C-terminus of an amino acid sequence of up to 15 aa and is followed by at least one neutral or non-charged amino acid, such as Glycine.

The invention further comprises an expression vector comprising said DNA sequence and the transfected cell clone carrying the recombinant sequence, either transiently or stably integrated into the genome. Preferred cell clones are those carrying stably integrated DNA copies of the vector, such as those obtained in CHO cells, more preferably, in suspension-growth adapted CHO cells, which are commercially available, i.e. in the Freedom™ CHO-S™ kit by Lifescience (ThermoFisher Scientific) together with an expression vector standardly used for mammalian cells expression.

Suspension-adapted CHO cells can be amplified and grown to a density of about $2.10^7$ cells/L, in order to achieve high efficiency secretion of the recombinant protein.

According to a further aspect, the invention comprises the process for preparing the recombinant chimeric protein as defined above, which comprises transforming a eukaryotic cell with the DNA sequence encoding it or the vector comprising the DNA sequence encoding it to achieve a recombinant eukaryotic system, preferably a CHO cell system stably expressing the chimeric protein and where said chimeric protein is preferably secreted into the medium, harvesting the culture medium and recovering the recombinant protein from the said culture medium by purification.

The purified recombinant chimeric protein can then be successfully conjugated through the C-term residue to diagnostic and/or therapeutic moieties or used as such, i.e. in combination with suitable ingredients or excipients in pharmaceutical compositions.

Conjugates of the Chimeric Protein for Diagnostic and Therapeutic Applications

The chimeric protein of the present invention is used to target diagnostically and therapeutically active moieties linked thereto, to selectin-expressing tissues, cells or organs. The specificity of the chimeric protein that is provided by the PSGL-1 region or fragments thereof, targets selectins if properly post-translationally modified (Liu et al. J. Biol. Chem., 1998, 273:7078-7087). It has been confirmed in this expression system, that the binding strength to the target is not altered by the presence of non-covalent dimerization domains such as leucine zippers which are endowed by a very peculiar secondary structure.

Therefore, according to one of the main embodiments, the present invention is directed to conjugates comprising the chimeric protein as the targeting agent of imaging moieties to selectin expressing cells, tissues, organs etc.

By "imaging moieties" we refer to any moiety detectable by diagnostic imaging procedures, i.e. any diagnostically effective moiety able to provide, to improve or, in any way, to advantageously modify the signal detected by an imaging diagnostic technique presently in use, including: ultrasound (US), computed tomography (CT), magnetic resonance imaging (MRI), positron emission tomography (PET), single photon emission computed tomography (SPECT), X-ray imaging, photoacoustic imaging, fluorescence and optical imaging, which in the present invention, comprises intraoperative imaging, i.e any technique enabling the registration of diagnostically useful, preferably contrasted, images. Hybrid imaging methods are also contemplated in the present invention, where the chimeric protein is linked to at least two moieties detectable with different imaging methods. Example of hybrid imaging are PET/CT, SPECT/CT, MR/PET, MR/SPECT; ultrasound and MR, ultrasound and CT; MR and CT.

The imaging moiety may comprise any possible combination of the imaging moieties for dual detection, for example for MRI/PET it may comprise a paramagnetic metal chelating unit and a radionuclide chelating unit. Examples of diagnostically effective moieties according to the invention comprise, for instance, chelated gamma ray or positron emitting radionuclides; paramagnetic metal ions in the form of chelated or polychelated complexes, X-ray absorbing agents including atoms having atomic number higher than 20; a dye molecule; a fluorescent molecule; a phosphorescent molecule; a molecule absorbing in the UV spectrum; a quantum dot; a molecule capable of absorption within near or far infrared radiations and, in general, all the moieties which generate a detectable signal or interact specifically with a detection system. From all of the above, it is known to the person skilled in the art that the imaging modality to be used has to be selected according to the imaging detectable moiety the diagnostic compounds of the invention are bound to. So that for example for a fluorescent imaging moiety such as CyC5 linked to the chimeric protein, a fluorescence light detection system will be appropriate.

The table below provides some exemplary contrast producing agent and the preferred imaging modality.

TABLE 2

Exemplary contrast producing agents and preferred imaging modality

| Modality | Contrast-Producing Agent |
| --- | --- |
| Ultrasound | Microbubble, acoustically active liposome |
| CT/X-Ray | Gold nanoparticles, iodinated nanoparticles, |
| MRI | Hyperpolarized neon/xenon/helium, gadolinium, iron oxide |
| PET | $^{18}F, ^{11}C$ |
| SPECT | $^{99m}Tc, ^{123}I, ^{111}In$ |
| Optical Imaging | Methylene-blue, fluorescent dye such as cyanine-dyes (Cy7, CyC5, indocyanine green) NIR dyes, IRDye800 ® CW, GFP, AlexaFluor ® dyes, microbubble, nanoparticle such as liposomes comprising fluorescent dyes DiR, NIR dyes, IRDye800 ® CW, GFP, AlexaFluor ® dyes |
| Photoacoustic Imaging | Carbon single-wall nanotubes (SWINT), indocyanine green, gold nanoparticles, zinc phthalocyanine. |

Conjugation of the Chimeric Protein to Diagnostic and Therapeutic Moieties for Molecular Targeting.

Preparation of conjugates of the chimeric protein of the invention is usually carried out by chemical means.

The reactive groups of the conjugation partners, i.e. the chimeric protein and the group(s) to be conjugated to it, are present or are prepared in a "protected" form. In the present description, unless otherwise indicated, the term "protecting group" designates a protective group adapted to preserve the characteristic chemical function of the functional group to which it is bound. Specifically, in the present context, protective groups are used to preserve amino or carboxyl functions. Appropriate protective groups may thus include, for example, Fmoc, benzyl, benzyloxycarbonyl or alkyl esters or other groups commonly intended for the protection of such functions and known to the skilled man.

Other chemical groups, able to chemically react with the N-terminal (—NH$_2$) or the C-terminal (—COOH) group of a polypeptide unit, such as the chimeric protein of the invention transforming such group, through a chemical reaction, into a suitable derivative maintaining the specificity of the corresponding polypeptide/protein toward selectin, but unable to chemically react with, respectively, a carboxyl or an amino functionality on a different moiety, are called "de-activating groups". Deactivating groups should not be involved in carboxamido cross-linking reactions. One example is represented by the acetyl-group [also referred to as CH₃(CO)— or even Ac], used to deactivate the amino terminus of a peptide chain by converting it into the corresponding unreactive acetylated AcHN— group.

On the other end, amino groups themselves and derivatives thereof such as, for instance, —NH₂, —NH(CH₃) or H₂NOC—CH₂—NH— may be used as "de-activating groups" for the free carboxyl group, by providing the corresponding —CONH₂, —CONH(CH₃) or —CONH—CH₂—CONH₂ unreactive amides, respectively.

For instance, if the chimeric protein includes a reactive amino group (e.g. a primary amino group of Lysine), it can be reacted with a diagnostic moiety, such as a microvesicle's component containing a suitable corresponding reactive moiety, such as an isothiocyanate group (to form a thiourea bond), a reactive ester (to form an amide bond), a carbonyl group (to form an imine bond, which may be reduced to an amine bond), an activated hydroxyl group, e.g., in the form of a tosylate, tresylated or cyanate, a vinyl sulfone or an epoxide.

Alternatively, when the targeting ligand of the present invention includes a reactive thiol group, suitable complementary reactive moiety on the diagnostic or therapeutic moiety, i.e. a microvesicle's component may include haloacetyl derivatives, maleimides (to form a thioether bond) or a mixed disulfide comprising a sulphide in the form of a 2-pyridylthio (PDT) group (which, upon reaction with a thiol derived from the targeting ligand, results in the formation of a stable disulfide bond), an activated hydroxyl group, e.g., in the form of a tosylate, tresylated or cyanate, a vinyl sulfone or an epoxide.

Alternatively, according to an embodiment of the invention, a targeting ligand containing an amino reactive moiety (e.g. a primary amino group, in particular the terminal —NH₂ group) can be first reacted with a sulphur-containing compound, to introduce a reactive thiol moiety in the targeting ligand, which is then reacted with a corresponding complementary moiety on the diagnostic component, i.e. a microvesicle's component as above illustrated. Examples of suitable sulphur-containing compounds useful for introducing a reactive thiol moiety in a targeting ligand containing a reactive amino moiety include, for instance: thioimidate (such as Traut's reagent) N-succinimidyl-S-acetylthioacetate (SATA), N-succinimidyl-S-acetylthiopropionate (SATP) or N-succinimidyl 3-(2-pyridyldithio)propionate (SPDP). Detailed description of S-containing agents and respective thiolation reactions can be found, for instance, in the book by Greg T. Hermanson: "Bioconjugate Techniques", Elsevier ed., 2$^{nd}$ ed. (April 2008), chapter 1, section 4-1. For instance, one may prepare a maleimide-derivatized phospholipid (e.g. phosphatidylethanolamine—PE—or pegylated PE) and react it with a targeting ligand (e.g. SEQ ID NO:3) where a primary amino group (e.g. the —NH₂ of Lysine side chain) has been previously reacted with a sulphur-containing compound (such as those previously illustrated), to introduce a reactive thiol moiety; the obtained compound can then be used in the preparation of targeted gas-filled microvesicles.

According to a further alternative, when the targeting ligand includes a reactive carboxylic group, suitable reactive moieties on the diagnostic or therapeutic group, i.e. microveside's component can be amines and hydrazides (to form amide or N-acyl, N'-alkylhydrazide functions).

According to the above preferred embodiment, the targeting ligand containing an amino reactive moiety (e.g. on a Lysine residue), can be first reacted with a maleimide-containing compound, to introduce a reactive maleimide moiety in the targeting ligand, which is then reacted with a corresponding complementary moiety on the microvesicle's component. Maleimide-containing agents useful for introducing a reactive maleimide moiety in a targeting ligand containing a reactive amino moiety and respective reaction of addition of maleimide group are well known in the art. Examples of suitable maleimide-containing compounds include, for instance: AMAS (N-(α-maleimidoacetoxy)succinimide ester), BMPS (N-(β-maleimidopropoxyl)succinimide ester), EMCS (N-(ε-maleimidocaproyloxy)succinimide ester), GMBS (N-(γ-maleimidobutyryloxy)succinimide ester), LC-SMCC (succinimidyl-4-(N-maleimidomethyl)-cyclohexane-1-carboxy-(6-amidocaproate)), MBS (m-maleimidobenzoyl-N-hydroxysuccimide ester), SMCC (succinimidyl-4-(N-maleimidomethyl)cyclohexane-1-carboxylate), SMPB (succinimidyl-4-(p-maleimidophenyl)butyrate), SM(PEG)n reagent (succinimidyl-(N-maleimidopropionamido)-ethyleneglycol) ester), SMPH (succinimidyl-6-((β-maleimidopropionamido) hexanoate)), sulfo-EMCS (N-(ε-maleimidocaproyloxy) sulfosuccinimide ester), sulfo-GMBS (N-(γ-maleimidobutyroyloxy)sulfosuccinimide ester), sulfo-KMUS (N-(κ-maleimidoundecanoyloxy)-sulfosuccinimide ester), sulfo-MBS (m-maleimidobenzoyl-N-hydroxysulfo-succinimide ester), sulfo-SMCC (sulfosuccinimidyl 4-(N-maleimidomethyl)-cyclohexane-1-carboxylate), sulfo-SMPB (sulfosuccinimidyl 4-(p-maleimidophenyl(butyrate)).

Other analogous reagents may contain sulfhydryl reactive groups different from maleimide, e.g., LC-SPDP (succinimidyl 6-[3-2-pyridyldithio)propionamido]hexanoate, NHS-Bromoacetate (N-hydroxysuccinimidyl bromoacetate), NHS-Iodoacetate (N-hydroxysuccinimidyl iodoacetate), SPDP (N-succinimidyl-3-(2-pyridyldithio)propionate), SULFO-LC-SPDP (sulfosuccinimidyl-6-[3-(2-pyridyldithio)propionamido]hexanoate).

According to the microvesicles embodiment for ultrasound diagnostic imaging, one may react a thiol-containing phospholipid (e.g. thiolated phosphatidylethanolamine—PE—or pegylated PE) with the targeting ligand where a primary amino group (e.g. the NH₂ of lysine side chain) has been previously reacted with a thiol reactive compound (e.g., a maleimide such as those previously illustrated), to introduce a thiol reactive moiety therein; the obtained compound can then be used in the preparation of the microvesicles or other diagnostic or therapeutic conjugates.

In the chimeric protein of the Invention, conjugates are preferably prepared at the C-terminus of the chimeric protein, leaving the N-terminus available for binding with the selectins target.

Diagnostically Effective Moieties for Ultrasound Microvesicles

A class of contrast agents, particularly useful for ultrasound contrast imaging, includes suspensions of gas bubbles of nano- and/or micro-metric size dispersed in an aqueous medium. Of particular interest are those formulations where the gas bubbles are stabilized, for example by using emulsifiers, oils, thickeners or sugars, or by entrapping or encapsulating the gas or a precursor thereof in a variety of systems. These stabilized gas bubbles are generally referred to in the art with various terminologies, depending typically from the stabilizing material employed for their preparation; these terms include, for instance, "microspheres", "microbubbles", "microcapsules" or "microballoons". The term "gas-filled microvesicles", or shortly "microvesicles", as used herein includes any of the above terminology.

Gas-Filled Microvesicles

According to a preferred embodiment of the present invention, the gas-filled microvesicles are prepared with lipids or phospholipids covalently associated to the chimeric protein of the present invention, as selectin targeting ligand and are preferably microbubbles. By microbubbles we refer to bubble of gas suspended in an aqueous carrier, which, at the gas-liquid interface possess a thin envelope (film) with a stabilizing amphiphilic material. Examples of aqueous suspensions of gas microbubbles are disclosed for instance in U.S. Pat. Nos. 5,271,928, 5,445,813, 5,413,774, 5,556, 610, 5,597,549, 5,827,504 and WO 04/069284. The term also comprises precursor of microbubbles in the form of freeze-dried or spray-dried component, preferably comprising phospholipid, dispersions.

At variance with microbubbles according to the above definition, the terms "microballoons" or "microcapsules" include suspensions in which the bubbles of gas are surrounded by a solid material envelope of a lipid or of natural or synthetic polymers. Examples of microballoons and of the preparation thereof are disclosed, for instance, in U.S. Pat. Nos. 5,711,933 and 6,333,021.

Components suitable for forming a stabilizing envelope of microbubbles comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate; tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol aliphatic acid esters including, cholesterol butyrate, cholesterol isobutyrate, cholesterol palmitate, cholesterol stearate, lanosterol acetate, ergosterol palmitate, or phytosterol n-butyrate; sterol esters of sugar acids including cholesterol glucuronides, lanosterol glucoronides, 7-dehydrocholesterol glucoronide, ergosterol glucoronide, cholesterol gluconate, lanosterol gluconate, or ergosterol gluconate; esters of sugar acids and alcohols including lauryl glucoronide, stearoyl glucoronide, myristoyl glucoronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol esters including glycerol tripalmitate, glycerol distearate, glycerol tristearate, glycerol dimyristate, glycerol trimyristate, glycerol dilaurate, glycerol trilaurate, glycerol dipalmitate; long chain alcohols including n-decyl alcohol, lauryl alcohol, myristyl alcohol, cetyl alcohol, or n-octadecyl alcohol; 6-(5-cholesten-30-yloxy)-1-thio-β-D-galactopyranoside; digalactosyldiglyceride; 6-(5-cholesten-3 β-yloxy)hexyl-6-amino-6-deoxy-1-thio-β-D-galactopyranoside; 6-(5-cholesten-3 β-yloxy) hexyl-6-amino-6-deoxyl-1-thio-β-D-mannopyranoside; 12-(((7'-diethylaminocoumarin-3-yl)carbonyl)methylamino) octadecanoic acid; N-[12-(((7'-diethylaminocoumarin-3-yl) carbonyl)methylamino)octadecanoyl]-2-aminopalmitic acid; N-succinyl-dioleoylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

Depending on the combination of components and on the manufacturing process of the microbubbles, the above listed exemplary compounds may be employed as the main compound for forming the microbubble's envelope or as simple additives, thus being present only in minor amounts.

According to a preferred embodiment, at least one of the compounds forming the microbubbles' envelope is an amphiphilic compound (i.e. an organic molecule comprising both a hydrophilic and lipophilic moiety), preferably a phospholipid, optionally in admixture with any of the other above-cited materials. According to the present description, the term phospholipid is intended to encompass any amphiphilic phospholipid compound, the molecules of which are capable of forming a stabilizing film of material (typically in the form of a mono-molecular layer) at the gas-water boundary interface in the final microbubbles suspension. Accordingly, these materials are also referred in the art as "film-forming phospholipids".

Amphiphilic phospholipid compounds typically contain at least one phosphate group and at least one, preferably two, lipophilic long-chain hydrocarbon groups.

Examples of suitable phospholipids include esters of glycerol with one or preferably two (equal or different) residues of fatty acids and with phosphoric acid, wherein the phosphoric acid residue is in turn bound to a hydrophilic group, such as, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol—PI). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipids are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acid di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DSPG, DPPA, DSPA, DMPS, DPPS, DSPS and Ethyl-DSPC. Most preferred are DSPG or DSPC.

Mixtures of phospholipids can also be used, such as, for instance, mixtures of DSPE, DPPE, DPPC, DSPC and/or DAPC with DSPS, DPPS, DSPA, DPPA, DSPG, DPPG, Ethyl-DSPC and/or Ethyl-DPPC.

In preferred embodiments, the phospholipid is the main component of the stabilizing envelope of microbubbles, amounting to at least 50% (w/w) of the total amount of components forming the envelope of the gas-filled microbubbles. In some of the preferred embodiments, substantially the totality of the envelope (i.e. at least 80% and up to 100% by weight) can be formed of phospholipids.

The phospholipids can conveniently be used in admixture with any of the above listed compounds. Thus, for instance, substances such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids in proportions ranging from zero to 50% by weight, preferably up to 25%. Particularly preferred are amphiphilic compounds, such as $C10$-$C_{20}$ carboxylic acids, preferably palmitic acid.

According to a preferred embodiment, the envelope of microbubbles according to the invention includes a compound bearing an overall (positive or negative) net charge. Said compound can be a charged amphiphilic material, preferably a lipid or a phospholipid.

Examples of phospholipids bearing an overall negative charge are derivatives, in particular fatty acid di-ester derivatives, of phosphatidylserine, such as DMPS, DPPS, DSPS; of phosphatidic acid, such as DMPA, DPPA, DSPA; of phosphatidylglycerol such as DMPG, DPPG and DSPG or of phosphatidylinositol, such as DMPI, DPPI or DPPI. Also modified phospholipids, in particular PEG-modified phosphatidylethanolamines, such as DPPE-PEG or DSPE-PEG, can be used as negatively charged molecules. Also the lyso-form of the above cited phospholipids, such as lyso-phosphatidylserine derivatives (e.g. lyso-DMPS, -DPPS or -DSPS), lysophosphatidic acid derivatives (e.g. lyso-DMPA, -DPPA or -DSPA) and lysophosphatidylglycerol derivatives (e.g. lyso-DMPG, -DPPG or -DSPG), can advantageously be used as negatively charged compounds. Other examples of negatively charged compounds are bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salts, stearic acid salts, 1,2-dipalmitoyl-sn-3-succinylglycerol salts or 1,3-dipalmitoyl-2-succinylglycerol salts.

Preferably, the negatively charged compound is selected among DPPA, DPPS, DSPG, DPPG, DSPE-PEG2000, DSPE-PEG5000 or mixtures thereof.

The negatively charged component is typically associated with a corresponding positive counter-ion, which can be mono- (e.g. an alkali metal or ammonium), di- (e.g. an alkaline earth metal) or tri-valent (e.g. aluminium). Preferably the counter-ion is selected among alkali metal cations, such as $Na^+$ or $K^+$, more preferably $Na^+$. Examples of phospholipids bearing an overall positive charge are derivatives of ethylphosphatidylcholine, in particular di-esters of ethylphosphatidylcholine with fatty acids, such as 1,2-distearoyl-sn-glycero-3-ethylphosphocholine (Ethyl-DSPC or DSEPC), 1,2-dipalmitoyl-sn-glycero-3-ethylphosphocholine (Ethyl-DPPC or DPEPC). The negative counter-ion is preferably a halide ion, in particular a chloride or a bromide ion. Examples of positively charged compounds that can be incorporated into the envelope of microbubbles are mono-, di- tri-, or tetra-alkylammonium salts with a halide counter ion (e.g. chloride or bromide) comprising at least one ($C_{10}$-$C_{20}$), preferably ($C_{14}$-$C_{18}$), alkyl chain, such as, for instance mono- or di-stearylammonium chloride, mono or di-hexadecylammonium chloride, dimethyldioctadecylammonium bromide (DDAB) or hexadecyltrimethylammonium bromide (CTAB). Further examples of positively charged compounds that can be incorporated into the envelope of microbubbles are tertiary or quaternary ammonium salts with a halide counter ion (e.g. chloride or bromide) comprising one or preferably two ($C_{10}$-$C_{20}$), preferably ($C_{14}$-$C_{18}$), acyl chains linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP) or 1,2-distearoyl-3-dimethylammonium-propane (DSDAP).

DSEPC, DPEPC and/or DSTAP are preferably employed as positively charged compounds in the microbubble envelope.

The positively charged component is typically associated with a corresponding negative counter-ion, which can be mono- (e.g. halide), di- (e.g. sulphate) or tri-valent (e.g. phosphate). Preferably the counter-ion is selected from among the halide ions, such as $F^-$ (fluorine), $Cl^-$ (chlorine) or $Br^-$ (bromine).

Mixtures of neutral and charged compounds, in particular of phospholipids and/or lipids, can be satisfactorily employed to form the microbubble envelope. The amount of charged lipid or phospholipid may vary from about 95 mol % to about 0.1 mol %, with respect to the total amount of lipid and phospholipid, preferably from 80 mol % to 0.5 mol %.

Preferred mixtures of neutral phospholipids and charged lipids or phospholipids are, for instance, DPPG/DSPC, DSTAP/DAPC, DPPS/DSPC, DPPS/DAPC, DPPE/DPPG, DSPA/DAPC, DSPA/DSPC, DSPC/PA (Distearoylphosphatidylcholine/Palmitic Acid) and DSPG/DSPC.

Any of the above illustrated components useful for forming the stabilizing envelope of the gas-filled microvesicle, in particular phospholipids, preferably pegylated phospholipids, can be modified by inserting a suitable reactive moiety therein, in order to allow binding suitable compounds, such as a targeting ligand comprising the sequence set forth as SEQ ID NO:1, or more preferably a sequence comprising amino acids 1-118 of SEQ ID NO:1. For instance, a pegylated phospholipid (e.g. DSPE-PEG2000) may comprise a terminal reactive moiety (e.g. maleimide, in brief "mal", thus forming a DSPE-PEG-mal component) capable of (covalently) reacting with a corresponding reactive moiety on a compound comprising the above sequence. Examples of additional suitable reactive moieties are illustrated in the following of this specification.

According to an alternative embodiment, the targeting ligand component can be associated with gas-filled microcapsules. Preferred examples of microcapsules are those having a stabilizing envelope comprising a polymer, preferably a biodegradable polymer, or a biodegradable water-insoluble lipid (such as tripalmitine) optionally in admixture with a biodegradable polymer. Examples of suitable microcapsules and of the preparation thereof are disclosed, for instance in U.S. Pat. Nos. 5,711,933 and 6,333,021, herein incorporated by reference in their entirety. Microcapsules having a proteinaceous envelope, i.e. made of natural proteins (albumin, haemoglobin) such as those described in U.S. Pat. No. 4,276,885 or EP-A-0 324 938 (here incorporated by reference), can also be employed. The targeting ligand can be incorporated into the microcapsules e.g. by binding it to an envelope-forming component of the microcapsules, according to the preparation methods illustrated above, or by admixing to the components forming the microcapsules envelope an amphiphilic component, as those previously illustrated, covalently bound to targeting ligand.

Other excipients or additives may be present either in the dry formulation of the microvesicles or may be added together with the aqueous carrier used for the reconstitution thereof, without necessarily being involved (or only partially involved) in the formation of the stabilizing envelope of the microvesicles. These include pH regulators (such as histidine), osmolality adjusters, viscosity enhancers, emulsifiers, bulking agents, etc. and may be used in conventional amounts. For instance compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars and hydrophilic polymers such as polyethylene glycol.

As the preparation of gas-filled microvesicles may involve a freeze drying or spray drying step, it may be advantageous to include in the formulation a lyophilization additive, such as an agent with cryoprotective and/or lyoprotective effect and/or a bulking agent, for example an amino-acid such as glycine; a carbohydrate, e.g. a sugar such as sucrose, mannitol, maltose, trehalose, glucose, lactose or a cyclodextrin, or a polysaccharide such as dextran; or a polyoxyalkyleneglycol such as polyethylene glycol. Typically, the amount of the lyophilization additive may range from about 10 to about 1000 times (w/w) amount of the microvesicle-forming components.

Any biocompatible gas, gas precursor or mixture thereof may be employed to fill the above microvesicles (hereinafter also identified as "microvesicle-forming gas"). The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane).

Preferred saturated perfluorocarbons include, for example, $CF_4$, $C_2F_6$, $C_3F_8$, $C_4F_8$, $C_4F_{10}$, $C_5F_{12}$ and $C_6F_{12}$.

It may also be advantageous to use a mixture of any of the above gases in any ratio. For instance, the mixture may comprise a conventional gas, such as nitrogen, air or carbon dioxide and a gas forming a stable microbubble suspension, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, selected among those previously illustrated, including mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

Particularly preferred gases are $SF_6$, $C_3F_8$, $C_4F_{10}$ or mixtures thereof, optionally in admixture with air, oxygen, nitrogen, carbon dioxide or mixtures thereof.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

For the use in MRI the microvesicles will preferably contain a hyperpolarized noble gas such as hyperpolarized neon, hyperpolarized helium, hyperpolarized xenon, or mixtures thereof, optionally in admixture with air, carbon dioxide, oxygen, nitrogen, helium, xenon, or any of the halogenated hydrocarbons as defined above.

For use in scintigraphy, the microvesicle will preferably contain radioactive gases such as $Xe^{133}$ or $Kr^{81}$ or mixtures thereof, optionally in admixture with air, carbon dioxide, oxygen, nitrogen, helium, kripton or any of the halogenated hydrocarbons as defined above.

Metal Chelating Agents for NMR Imaging and Therapy.

The most reliable and most frequently applied method of linking a metal ion which can be either the imaging probe or radiotherapic effector, to a biomolecule such as the chimeric protein of the invention, is by means of bifunctional chelating agents, which carry the metal chelating cage and a reactive group to covalently link the biomolecule.

Metal coordination cages can be divided into cyclic, such as DOTA (1,4,7,10-tetraazacyclododecane-1,4,7,10-tetraacetic acid) or TETA (1,4,8,11 tetraazacyclododecane-1,4,8,11-tetraacetic acid), or linear such as EDTA (ethylendiaminotetraacetic acid) or DTPA (diethylenetriaminopentaacetic acid).

Once the most suitable metal chelating cage, or "chelating ligand" has been selected, conjugation to the biomolecule of interest via a reactive group, can be carried out by solid phase synthesis or in solution. Lattuada L. et al. reviews in Chem Soc. Rev, 2011, 40, 3019-3049 the synthetic approaches for conjugating metal chelating ligands to other moieties, in particular biomolecules, to prepare targeted metal chelating agents.

According to the embodiment disclosed in this paragraph, the metal is either detectable by an imaging technique or a radionuclide useful for therapy. Metals suitable for imaging specifically include paramagnetic metal ions detectable by Magnetic Resonance Imaging (MRI), or radionuclides detectable by imaging techniques such as Scintigraphy, Single Photon Emission Computed Tomography (SPECT) and Positron Emission Tomography (PET).

In this context, the terms: "chelator", "chelating ligand" or "chelating agent" comprise chemical moieties, agents, compounds, or molecules characterized by the presence of polar groups able to a form a complex containing more than one coordinate bond with a transition metal or another metal. In a preferred aspect of the invention said chelating ligand includes cyclic or linear polyamino polycarboxylic or polyphosphonic acids and contains at least one amino, thiol or carboxyl group present as free or optionally activated functionality, suitable for conjugating the functional groups of the targeting protein or a suitable bifunctional linkers.

Linkers may be used as spacers or to improve the pharmacokinetic properties of the whole molecule. Some of the most frequently used linkers have been summarized in Liu S. and Edwards S. Bioconjugate Chem. 2001, 12: 7-34 as well as disclosed for peptide conjugation, in WO2008/071679.

With the term "labelled" or "complexed" as used herein i.e. in the context of "chelating ligand labelled with a metal", we refer to a ligand that is complexed with the metal, i.e. a ligand that is in the form of a chelate or coordinate complex with the metal element.

Figure 3:
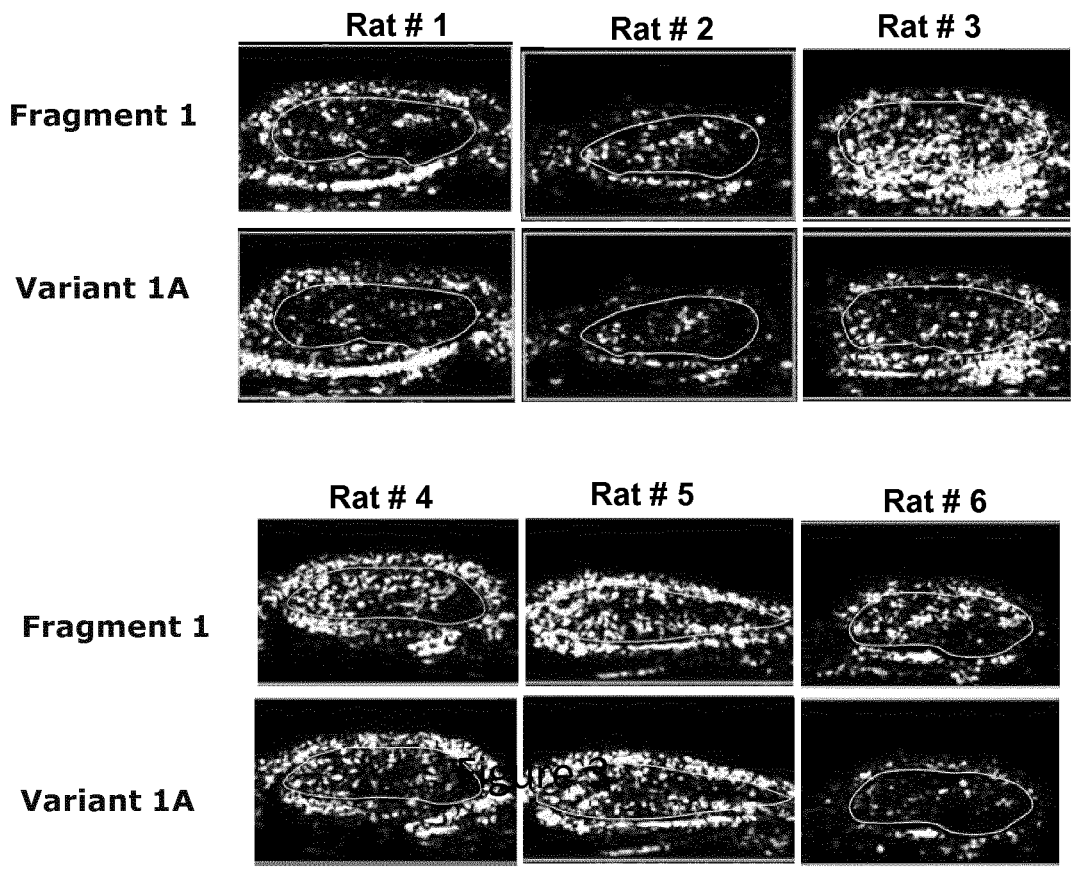
FIG. 3. Ultrasound imaging of rat inflammatory hind limbs. Images were obtained with Fixed Bubble Imaging (FBI), 10 minutes after Fragment-1 or Variant 1A microbubble injection.
Figure 4:
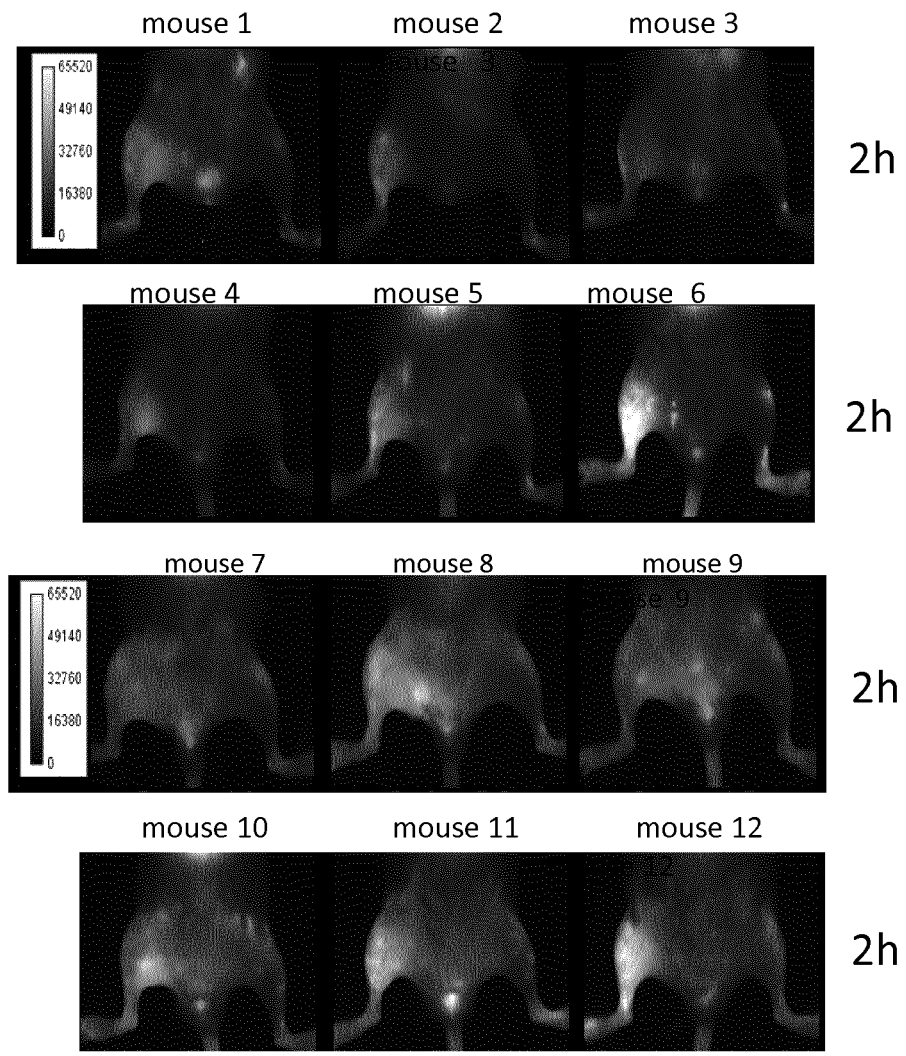
FIG. 4. Optical imaging of mice hind limb inflammatory LPS model after injection of liposomes loaded with either Variant 1A-liposomes-DIR (mice 1 to 6) or Fr-1-liposomes-DIR (mice 7 to 12).

With the terms "metal entity" or "metal element", we refer to a metal ion that is detectable by an imaging technique, or radionuclides for either imaging or therapy. The term comprises paramagnetic metal ions detectable by Magnetic Resonance Imaging (MRI) and radiation emitting metals such as radionuclides, detectable by scintigraphic imaging, Single Photon Emission Computed Tomography (SPECT) and Positron Emission Tomography (PET) or suitable for radiotherapy, as defined below. Suitable chelating ligands are selected from the group consisting of: a polyaminopolycarboxylic acid and the derivative thereof comprising, for example, diethylenetriamine pentaacetic acid (DTPA) and derivative thereof including benzo-DTPA, dibenzo-DTPA, phenyl-DTPA, diphenyl-DTPA, benzyl-DTPA and dibenzyl DTPA, N,N-Bis[2-[(carboxymethyl)[(methylcarbamoyl) methyl]ethyl]-glycine (DTPA-BMA), N-[2-[bis(carboxymethyl)amino]-3-(4-ethoxyphenyl)propyl)]-N-[2-[bis(carboxymethyl) amino]ethyl]glycine (EOB-DTPA), 4-carboxy-5,8,11-tris(carboxymethyl)-1-phenyl-2-oxa-5,8,11-triazatridecan-13-oic acid (BOPTA), N,N-bis[2-[bis (carboxymethyl)amino]ethyl]L-glutamic acid (DTPA-GLU); DTPA-Lys (see compound 1 of FIG. 3a); ethylenediaminetetraacetic acid (EDTA); 1,4,7,10-tetraazacyclododecane 1,4,7-triacetic acid (DO3A) and derivatives thereof including, for example, [10-(2-hydroxypropyl)-1,4, 7,10-tetraazacyclododecane 1,4,7-triacetic acid (HPDO3A); 1,4,7-triazacyclononane N,N',N"-triacetic acid (NOTA); 6-[bis(carboxymethyl)amino]tetrahydro-6-methyl-1H-1,4-diazepine-1,4(5H)-diacetic acid (AAZTA) and derivative thereof, for instance as disclosed in WO03/008390, incorporated herein by reference, 1,4,7,10-tetra-azacyclotetradecane-1,4,7,10-tetraacetic acid (DOTA) and derivatives thereof including, for instance, benzo-DOTA, dibenzo-DOTA, (α,α',α",α'")-tetramethyl-1,4,7,10-tetraazacyclotetradecane-1,4,7,10-tetraacetic acid (DOTMA); or 1,4,8,11-tetraazacyclotetradecane-N,N',N",N'"-tetraacetic acid (TETA); or corresponding compounds wherein one or more of the carboxylic groups is replaced by a phosphonic and/or phosphinic group, including, for instance, N,N'-bis-(pyridoxal-5-phosphate) ethylenediamine-N.N'-diacetic acid (DPDP); ethylenedinitrilo tetrakis(methylphosphonic) acid (EDTP), 1,4,7,10-tetraazacyclotetradecane-1,4,7,10-tetra (methylenephosphonic) acid (DOTP), the phosphonoalkylpolyaza macrocyclic compounds for instance disclosed in U.S. Pat. Nos. 5,362,476 and 5,409,689 and the linear phosphonoalkyl derivatives disclosed in U.S. Pat. No. 6,509, 324; or macrocyclic chelants such as texaphirines, porphyrins, phthalocyanines.

Among the above, particularly preferred are: DTPA, DTPA-Glu, DTPA-Lys, DOTA and DOTA derivatives, such as those disclosed in Price E W and Orvig, Chem. Soc. Rev. 2014, 43:260 and the pyridil-DO3A disclosed in Hermann et al, Dalton Trans., 2008, 3027-3047 or the multidentate ligand AAZTA and its derivatives described, i.e. in WO03/ 008394 and WO2013/135750.

Preferred paramagnetic metal elements for MRI are those having atomic number ranging from 20 to 31, 39, 42, 43, 44, 49 and from 57 to 83.

Even more preferred paramagnetic metal ions are selected from the following: $Fe(2^+)$, $Fe(3^+)$, $Cu(2^+)$, $Ni(2^+)$, $Rh(2^+)$, $Co(2^+)$, $Cr(3^+)$, $Gd(3^+)$, $Eu(3^+)$, $Dy(3^+)$, $Tb(3^+)$, $Pm(3^+)$, $Nd(3^+)$, $Tm(3^+)$, Ce(3+), Y(3+), Ho(3+), Er(3+), La(3+), Yb(3+), Mn(3+), Mn(2+; Gd(3+) being the most preferred.

Nuclear Imaging (Radionuclide Imaging) and Radiotherapy

In another embodiment of the invention, the moiety to which the selectin targeting chimeric protein of the present invention is linked, is a radionuclide, for radioimaging (diagnostic) or radiotherapy (therapeutic application).

The main features of a radiometal chelating moiety relates to its use in vivo at extremely diluted conditions, i.e. from nM to pM concentrations; however some of the most suitable matches between chelating moiety and radiometal are known and summarized in Price E W and Orvig C Chem. Soc. Rev, 2014, 43, 260.

For radioimaging, the targeting agent can be linked to a "radioimaging detectable moiety" i.e. a moiety that is detectable by imaging techniques such as scintigraphic imaging, Single Photon Emission Computed Tomography (SPECT) or Positron Emission Tomography (PET).

Preferably, said radioimaging detectable moiety comprises a radionuclide chelated to a chelating agent which is usually bifunctional and which comprises the chelating moiety with metal complexing properties and a functional group for attachment to the biomolecule, such as the Selectin targeting agent of the present invention or, alternatively, is directly linked to the biomolecule (i.e. iodine).

Functional groups forming an amide, thiourea, urea, Schiff base or thioether bonds with amine or thiol groups on proteins may be prepared carrying the chelating agent, labelled with a radionuclide detectable by the said scintigraphic, SPECT or PET imaging techniques.

In any case, the most preferred chelating ligands are linear or more preferably macrocyclic chelating ligands and are those discussed above, such as DTPA or, more preferably, DOTA which still represents a gold standard for a number of isotopes including $^{111}$In, $^{177}$Lu, $^{86/90}$Y, $^{225}$Ac and $^{44/47}$Sc and which has been extensively used with $^{67/68}$Ga, even though more recently replaced by the more stable NOTA and DOTA derivatives thereof.

Further suitable examples of chelating ligands for radionuclides may be selected from linear, macrocyclic, terpyridine, and $N_3S$, $N_2S_2$, $N_2S_3$, $N_2S_4$, $N_3S_3$ or $N_4$ chelators including, for instance, the ligands disclosed in U.S. Pat. Nos. 5,367,080, 5,364,613, 5,021,556, 5,075,099 and 5,886, 142, and other chelating ligands known in the art including, but not limited to, 6-Hydrazinopyridine-3-carboxylic acid (HYNIC), or 1,4,8,11-tetraazacyclotetradecane-N,N',N", N'"-tetraacetic acid (TETA); and bis-amino bis-thiol (BAT) chelators such as, for instance, those disclosed in U.S. Pat. No. 5,720,934, or phospho-derivatives of polyazamacrocyclic compounds, such as those described in WO2005/ 062828.

$N_4$ chelating ligands are also described, for instance, in U.S. Pat. Nos. 5,608,110, 5,665,329, 5,656,254 and 5,688, 487. Certain $N_3S$ or $N_2S_2$ chelators are described, for instance, in U.S. Pat. Nos. 5,659,041, 5,574,140, 5,780,006, 5,662,885 and 5,976,495. The chelators may also include derivatives of the chelating ligand mercapto-acetyl-acetylglycyl-glycine (MAG3), which contains an $N_3S$ and $N_2S_2$ system such as MAMA (monoamidemonoaminedithiols), DADS ($N_2S$ diaminedithiols), CODADS, and the like. These ligand systems and a variety of others are described in Liu and Edwards, Chem Rev, 1999, 99, 2235-2268 and references cited therein.

The chelating may also include complexes containing ligand atoms that are not donated to the metal in a tetradentate array. These include the boronic acid adducts of technetium and rhenium dioximes, for instance described in U.S. Pat. Nos. 5,183,653, 5,387,409 and 5,118,797.

In another embodiment, disulfide bonds of the fusion protein or polypeptide of the invention are used as ligands for chelation of a radionuclide such as $^{99m}$Tc. In this way, the peptide loop is expanded by the introduction of Tc (peptide-S—S-peptide changed to peptide-S—Tc—S-peptide).

Preferred radionuclides according to the present invention include, for instance: $^{99m}$Tc, $^{51}$Cr, $^{67}$Ga, $^{68}$Ga, $^{47}$Sc, $^{167}$Tm, $^{141}$Ce, $^{111}$In, $^{113}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{61}$Cu, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au, $^{111}$Ag, $^{199}$Au, $^{51}$Mn, $^{52m}$Mn, $^{52}$Fe, $^{60}$Cu, $^{72}$As, $^{94m}$Tc, or $^{110}$In, $^{142}$Pr, $^{159}$Gd.

The choice of the radionuclide will be based on the desired therapeutic or diagnostic application. For example, for therapeutic purposes (e.g., to provide radiotherapy for primary tumors and metastasis), the preferred radionuclides may include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/181}$Re, and $^{199}$Au, with $^{186/188}$Re, $^{177}$Lu and $^{90}$Y being particularly preferred. For diagnostic purposes (e.g., to locate inflammation and to monitor its development after therapy) the preferred radionuclides may include $^{64}$Cu, $^{67}$Ga, $^{68}$Ga, $^{99m}$Tc, and $^{111}$In. $^{99m}$Tc is particularly preferred for diagnostic applications because of its low cost, availability, imaging properties and high specific activity. In particular, the nuclear and radioactive properties of $^{99m}$Tc make this isotope an ideal scintigraphic imaging agent. This isotope, in fact, has a single photon energy of 140 keV and a radioactive half-life of about 6 hours, and is readily available from a $^{99}$Mo-$^{99m}$Tc generator.

Preferred metal radionuclides for use in PET imaging are positron emitting metal ions such as, for instance: $^{51}$Mn, $^{52}$Fe, $^{60}$Cu, $^{68}$Ga, $^{72}$As, $^{94m}$Tc or $^{110}$In.

Preferred chelating ligands are for $^{111}$In and radioactive lanthanides such as, for instance, $^{177}$Lu, $^{90}$Y, $^{153}$Sm, and $^{166}$Ho or for $^{67}$Ga, $^{68}$Ga, $^{61}$Cu, $^{62}$Cu, $^{64}$Cu or $^{67}$Cu) selected from the group consisting of:

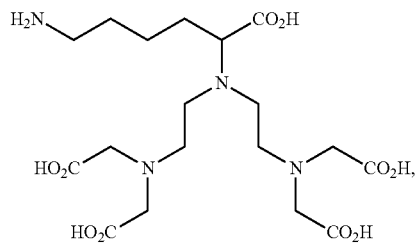

Bioconj. Chem (1999), 10, 137

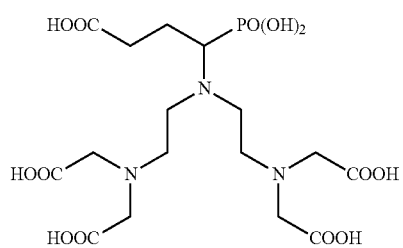

WO 01/46207

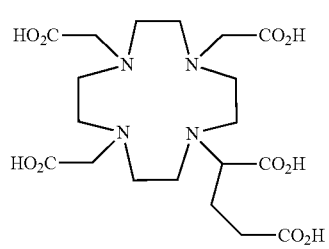

Bioorg Med Chem Lett (2000), 10: 2133

In particular, for metal entities including $^{111}$In and radioactive lanthanides such as, for example $^{17}$Lu, $^{90}$Y, $^{113}$Sm, and $^{166}$Ho, particularly preferred are the following ligand residues:

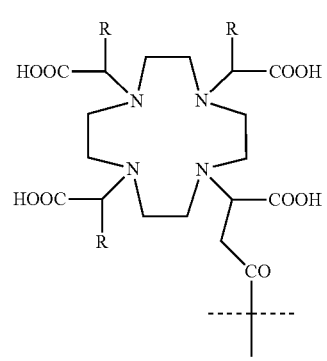
a)

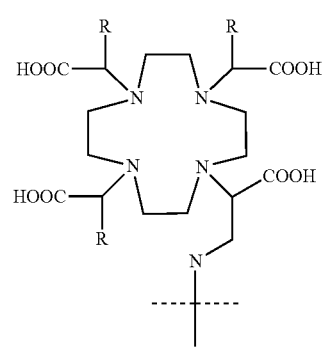
b)

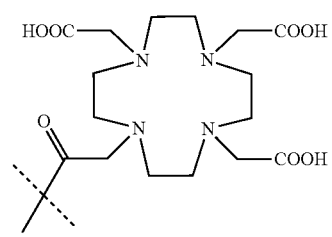
c)

where in the above formulae a) and b), R is alkyl, preferably methyl.

For radioactive $^{99m}$Tc, $^{186}$Re, $^{188}$Re, particularly preferred are the following chelating moieties from d) to l) below:

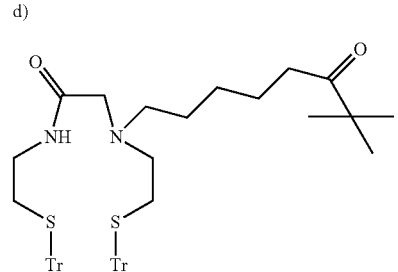
d)

e)

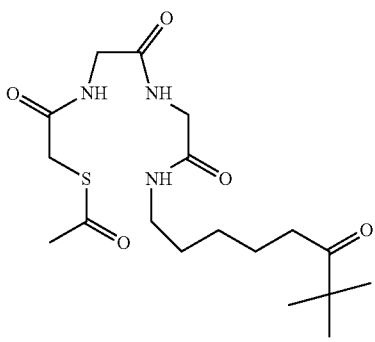

f)

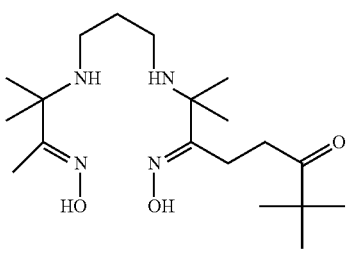

g)

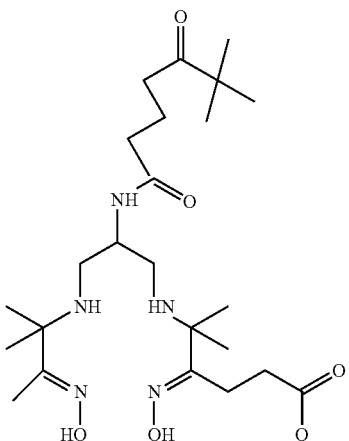

h)

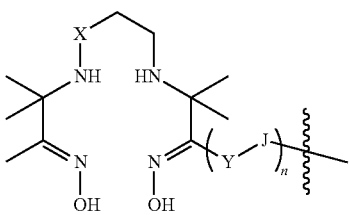

i)

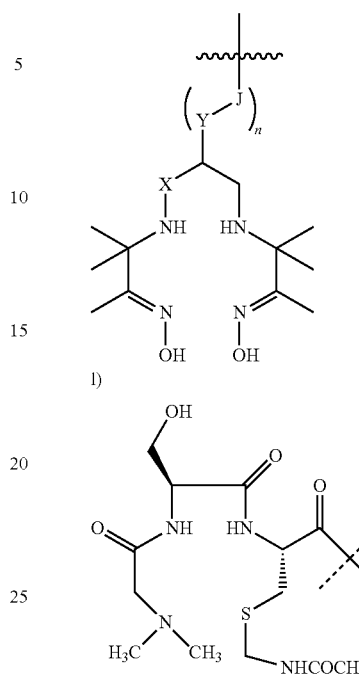

l)

These and other metal chelating groups are for instance described in U.S. Pat. Nos. 5,608,110, 6,143,274, 5,627,286, 5,662,885, 5,780,006 and 5,976,495.

Additionally, the above chelating group of formula c) is described in U.S. Pat. No. 6,143,274; the chelating groups of the above formulae h) and i) are described in U.S. Pat. Nos. 5,627,286 and 6,093,382; and the chelating group of formula I) is described in U.S. Pat. Nos. 5,662,885, 5,780,006 and 5,976,495.

In the formulae h) and i), X is either $CH_2$ or O, Y is either $C_1$-$C_{10}$ branched or unbranched alkyl; Y is aryl, aryloxy, arylamino, arylaminoacyl; Y is arylkyl where the alkyl group or groups attached to the aryl moiety are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is >C(=O), —OC(=O)—, —$SO_2$—, >NC(=O)—, >NC(=S)—, —N(Y)—, —NC(=$NCH_3$)—, —NC(=NH)—, —N=N—, homopolyamides or heteropolyamines derived from synthetic or naturally occurring amino acids; all where n is 1-100. Folate derivatives of these structures are described, for example, in U.S. Pat. No. 6,093,382.

More preferred for scintigraphy, are radioimaging contrast agents comprising one of the above ligand residues from a) to l) above labelled with $^{99m}$Tc as imaging detectable moiety.

PET Imaging with Labelled Sugars

In a still further embodiment of the invention, the fusion protein is linked to a labelled sugar moiety for use in PET Imaging.

Preferably, the sugar moiety is labelled by halogenation with radionuclides such as, for instance: $^{124}$I, $^{125}$I, $^{131}$I, $^{123}$I, $^{77}$Br, $^{76}$Br and $^{18}$F; $^{18}$F being as particularly preferred.

Optical Imaging

In some embodiments, an optical imaging agent is conjugated to the chimeric protein of the invention. Among optical imaging agents, fluorescent dyes for imaging applications in vivo, ex vivo and in vitro are well known by the skilled artisan and a wide range of fluorochromes which are optimal for the in vivo fluorescence imaging have been developed and are also commercially available. These reagents maximise to different extents, the depth of tissue penetration, the light scattering and fluorescence emission properties of fluorescent chromophores, to provide optimal signal-to-background ratios. In general, light absorption and scattering decrease with increasing wavelength; below about 700 nm, these effects result in shallow penetration depths of few millimeters, while above 900 nm water absorption can interfere with signal-to-background ratio. Therefore fluorochromes with excitation/emission in the near infrared (NIR) region (700-900 nm) have been mostly exploited up to now for in vivo imaging in small animals and, potentially, in humans.

Among these the most used are: Indocyanin Green, cyanine derivatives Cy3, Cy3.5, Cy5 and Cy5.5, Cy7 (cyanine dyes and derivatives are made available, i.e. by GE Healthcare), LS-287, LS-288, IRDye® 800CW, IR-820, IR®-806, IR-786, IRDye® 800RS, IRDye® 750, IRDye® 650 (IRDye®s are made available from Li-Cor Bioscience), Alexa Fluor® 647, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 568, Alexa Fluor® 594, Alexa Fluor® 680, Alexa Fluor® 750 (Alexa Fluor® dyes are made available, i.e. from Invitrogen), combination thereof and others, whose chemical structures have been reported for example in WO2014/191467. The structure of most of the compounds for image-guided surgery and their commercial availability has been described, i.e. in Gibbs S. L. Quant Imaging Med Surg 2012, 2(3):177-187. Particularly preferred are cyanine dyes and their chemical derivatives developed for NIR imaging, such as: Cy5.5, IRDye® 800CW, IRDye® 800RS and IRDye® 750.

Uses

The above described targeted diagnostic agents are particularly useful for imaging in vivo and ex vivo. The chimeric targeting protein of the invention can further be used for therapeutic purposes, which include any method for the treatment of a disease in a patient where the chimeric targeting protein of the invention is used, optionally in association with an imaging agent, to deliver ex-vivo and/or in vivo, a therapeutic compound, i.e. a molecule which is capable of exerting or is responsible to exert a biological effect, to selectin expressing cell, tissue or organ.

Typically, this use involve the conjugation of the chimeric protein of the invention with an agent/moiety/molecule endowed with a biological activity, such as a cytokine, cytostatic agent (such as doxorubicin, methotrexate, cisplatin, vinblastin, vincristin, etc.) toxin, anti-inflammatory agent, immunomodulator such as a cytokine inhibitor, anti-aggregant, corticosteroid, monoclonal antibody, growth factor and the above described radiotherapic agents comprising metal chelating moieties carrying a radionuclide, and is effected to target the biologically active moiety to the selectin expressing tissue/cell/organ, where an inflammation is observed or detected.

The pathological inflammatory condition, either for diagnostic and/or therapeutic purposes, should be characterized by selectin expression levels above physiological; the selectin is preferably E-selectin and/or P-selectin, more preferably P-selectin. In particular the imaging agents of the invention are useful to detect inflammatory conditions of the vascular endothelium such as the ones listed below.

More preferably, the pathological inflammatory condition is selected among the following, characterized for selectin expression levels above physiological: Acute Coronary Syndrome (ACS), Inflammatory Bowel Disease (IBD), Ulcerative colitis, Crohn's disease, neo-angiogenesis associated with tumors, rheumatoid arthritis, ischemia reperfusion injury, graft rejection or, more in general, of any organ or tissue expressing P-selectin and/or E-selectin above physiological levels.

More preferably, the chimeric protein of the invention is a useful targeting agent for IBD, ACS, tumour detection and graft rejection.

Furthermore, the targeted imaging agents according to the invention is employed as an efficient diagnostic tool during the (therapeutic) treatment of a patient suffering from an inflammatory disease or pathology, where "during" includes any time before the beginning of the treatment, in the course of said treatment and/or at the end of said treatment, to monitor and evaluate it. For instance the targeted imaging agents of the invention can advantageously be employed in the monitoring and/or follow-up of an anti-inflammatory treatment (e.g. of any of the above cited diseases or pathologies), e.g. to determine or evaluate the effects of the administration of an anti-inflammatory or inflammatory-inhibitor drug on the disease or pathology.

For example, in IBD, the targeted imaging agents of the invention can be used to follow-up the response to the therapeutic treatment with, i.e. mesalamine, corticosteroids, methotrexate or infliximab and to stratify patients according to their response to the therapeutic treatment or to monitor the remission maintenance therapy. Preferably, the imaging technique is based on the chimeric soluble protein-targeted microbubbles for ultrasound detection.

In a preferred embodiment, during a treatment a region of interest of the patient is subjected to the imaging detection system of choice upon administration of the targeted imaging agents of the invention, for instance at regular time intervals, at a predetermined time interval after each drug administration or therapeutic intervention and/or after a selected number of drug administrations or treatments; a final imaging of the region of interest is then preferably performed at the end or conclusion of the treatment.

The targeted imaging agents of the invention can be further used in ultrasound-related techniques, i.e. in therapeutic-associated imaging, in which they are advantageously associated with a controlled localized destruction of the gas-filled microvesicles, e.g. by means of ultrasound waves at high acoustic pressure (typically higher than the one generally employed in non-destructive diagnostic imaging methods). This controlled destruction may be used, for instance, for the treatment of blood clots (a technique also known as sonothrombolysis), optionally in combination with the release of a suitable therapeutic compound associated with the contrast agent. Alternatively, said therapeutic-associated imaging may include the delivery of a therapeutic agent into cells, as a result of a transient membrane permeabilization at the cellular level induced by the localized burst or activation of the microvesicles. This technique can be used, for instance, for an effective delivery of genetic material into the cells; alternatively, a drug can be locally delivered, optionally in combination with genetic material, thus allowing a combined pharmaceutical/genetic therapy of the patient (e.g. in case of tumor treatment). The therapeutic agent can be associated with the gas-filled microvesicle according to conventional methods, or can be administered as a separate compound of the composition. In addition, the targeting agent could be used to facilitate the delivery of therapeutic agent into the brain tissue by transient opening of the Blood Brain Barrier following exposure to ultrasound.

Typically, an effective amount of the targeted diagnostic agent is administered (e.g. by injection) to a patient in need thereof and the body part or tissue of the patient to be imaged or treated ("region of interest") is subjected to the desired imaging method. Preferably, the contrast agent is administered intravenously. The term patient includes any subject (human or animal) undergoing the administration of the contrast agent, either for diagnostic/therapeutic purposes or for experimental purposes (including, for instance, use of a contrast agent in laboratory animals, e.g. to follow an experimental therapeutic treatment).

According to a preferred embodiment, an effective amount of targeted microvesicles is administered to a patient, typically by injection of a suspension thereof. The imaging of the region of interest will thus be enhanced by the presence of the microvesicles bound to the target in the region of interest.

A variety of imaging techniques may be employed in ultrasound applications, for example including fundamental and non-linear (e.g. harmonic) B-mode imaging, pulse or phase inversion imaging and fundamental and non-linear Doppler imaging; if desired three- or four-dimensional imaging techniques may be used. Furthermore, diagnostic techniques entailing the destruction of gas-filled microvesicles (e.g. by means of ultrasound waves at high acoustical pressure) which are highly sensitive detection methods are also contemplated.

Microvesicles according to the invention can typically be administered in a concentration of from about 0.01 to about 5.0 µl of gas (entrapped inside the microvesicles) per kg of patient, depending e.g. on their respective composition, the tissue or organ to be imaged and/or the chosen imaging technique. This general concentration range can of course vary depending from specific imaging applications, e.g. when signals can be observed at very low doses such as in color Doppler or power pulse inversion. Possible other diagnostic imaging applications include scintigraphy, optical imaging, photo-acoustic imaging, magnetic resonance imaging and X-ray imaging, including X-ray phase contrast imaging.

Ultrasound imaging methods can be also conveniently used in association with MRI as mentioned above for combined- (or fusion-) imaging methods to achieve better mapping of the affected lesion.

Pharmaceutical Compositions

The invention further comprises pharmaceutical compositions comprising the above disclosed chimeric protein, either conjugated or modified according to the uses envisaged, which may be administered topically, or parenterally including intranasal, subcutaneous, intramuscular, intravenous, intra-arterial, intraarticular, or intralesional administration. Ordinarily, intravenous (i.v.), intraarterial, intraarticular, intracardiac administration is preferred.

The molecules of the present invention, as the active ingredient, are dissolved, dispersed or admixed in a diluent or excipient that is pharmaceutically acceptable and compatible with the active ingredient, as well known in the art. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, stabilizing and/or pH buffering agents.

Pharmaceutical compositions according to the present invention may be manufactured by means, i.e. of conventional mixing, dissolving, granulating, grinding, pulverizing, dragee-making, levigating, emulsifying, encapsulating, entrapping or lyophilizing processes.

Pharmaceutical compositions for use in accordance with the present invention thus, may be formulated using one or more physiologically acceptable carriers comprising excipients and auxiliaries, which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer further comprising suitable excipients or stabilizing compounds.

Oral administration can be achieved by liquid or solid compositions. Among the latter dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Orally administered solid compositions include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

In one embodiment according to the present invention, the peptides are administered orally (e.g. as a syrup, capsule, or tablet). In certain embodiments, peptide delivery can be enhanced by the use of protective excipients. This is typically accomplished either by complexing the peptide with a composition to render it resistant to acidic and enzymatic hydrolysis or by packaging the peptide in an appropriately resistant carrier such as a liposome. Means of protecting peptides for oral delivery are well known in the art.

Compressed tablets may be prepared by compressing in a suitable machine the active peptide(s) in a free-flowing form such as a powder or granules, optionally mixed with a binder, (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose), surface active or dispersing agent. Molded tablets may be made by molding in a suitable machine a mixture of the powdered peptide(s) moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile.

Syrup may be made by adding the active peptide(s) to a concentrated, aqueous solution of a sugar, for example, sucrose, to which may also be added any necessary ingredients. Such accessory ingredients may include flavorings, an agent to retard crystallization of the sugar or an agent to increase the solubility of any other ingredients, such as a polyhydric alcohol, for example, glycerol or sorbitol.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflators may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable natural or synthetic carriers are well known in the art. The suspension may also contain suitable stabilizers or agents, which increase the solubility of the compounds or the stability of the chimeric protein or the conjugated group, to allow for the preparation of concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

Elevated serum half-life can be maintained by the use of sustained-release protein or lipids as "packaging" systems. Such sustained release systems are well known to those of skill in the art and may comprise formulation of the chimeric protein as such or in a conjugated form into nanospheres, nanovesicles or liposomes.

The foregoing formulations and administration methods are intended to be illustrative and not limiting. It will be appreciated that, using the teaching provided herein, other suitable formulations and modes of administration can be readily devised.

Pharmaceutical compositions suitable for use in context of the present invention include compositions wherein the active ingredients are contained in an amount effective to achieve the intended purpose. More specifically, a therapeutically effective amount means an amount of a compound effective to prevent, delay, alleviate or ameliorate symptoms of a disease of the subject being treated. Determination of a therapeutically effective amount is well within the capability of those skilled in the art according, i.e. to Goodman & Gilman, 9$^{th}$ ed, JG Hardman, A. Gilman, L E Limbird, Chapter I "Pharmacokinetics", pp 3-27.

Accordingly, the present invention further comprises methods for administration of the chimeric protein above disclosed either as such or preferably as a conjugate to persons in need thereof, for therapeutic or, preferably, diagnostic purposes.

For diagnostic purposes the pharmaceutical compositions of the invention may be pre-administered in a suitable dosage, depending on the administration route and sensibility of the diagnostic method, and then imaging carried out by the most suited technique.

EXPERIMENTAL PART

Example 1: Preparation and Expression of Flagged Recombinant Fusion Proteins

A number of DNA constructs were prepared:
PSGL Variant 1: the sequence encodes for aminoacids 1-47 of the mature PSGL-1 protein, the IgG1 hinge region, the Leucine Zipper domain of NRL, a glycine ($G_4SG_4$) spacer and a FLAG sequence for affinity recognition. The mouse IgH signal peptide was used for secretion. The Variant 1 chimeric protein has amino acid sequence SEQ ID NO:2.
The PSGL Variant 2, which encodes for amino acids 1-47 of the mature PSGL-1 protein, a IgG1 hinge region, a IgG1CH3 region with K→A sequence replacements. The mouse IgH signal peptide was used for secretion. A FLAG Sequence (SEQ ID NO:35) at the C-term, was used for purification purposes. The chimeric protein has SEQ ID NO:4.
PSGL Variant 3: encoding for amino acids 1-47 of the mature PSGL-1 protein, covalently linked to the IgG1 hinge region, to region 275-290 of the mature PSGL-1 protein and a FLAG Sequence (SEQ ID NO:35) at the C-term, used for identification and purification purposes. The mouse IgH signal peptide was used for secretion. The chimeric protein has SEQ ID NO:6.
The PSGL Variant 4 encodes for amino acids 1-47 of the mature PSGL-1 protein, covalently linked to the IgG1 Hinge region and aa 1-15 of the human IgG1 Fc region. The mouse IgH signal peptide was used for secretion. A FLAG Sequence (SEQ ID NO:35) at the C-term, was used for purification purposes. The chimeric protein has SEQ ID NO:8.
The PSGL Variant 5 encodes for amino acids 1-88 of the PSGL-1 protein (according to GI:2498904) with the endogenous signal and propeptide sequence covalently linked to the IgG1 Hinge region and aa 1-15 of the human IgG1 Fc region. A FLAG Sequence (SEQ ID NO:35) at the C-term for affinity recognition, was used for purification purposes. The chimeric protein has SEQ ID NO:10.

Small-Scale Transient Transfection

CHO-S, a suspension-adapted Chinese hamster ovary cell line (Freedom™ CHO-S™ Kit, GIBCO ThermoFisher Scientific) was cultured according to the Manufacturer's instruction (July 2015) in a humidified 5% $CO_2$ incubator at 37° C. in chemically defined media CD-CHO (Invitrogen, Carlsbad Calif., Catalog #12490-025, Lot #1149771) supplemented with L-glutamine (Cellgro, Catalog #61-030-RO, Lot #61030158). No serum or other animal-derived products were used in culturing the CHO-S cells. 24 hours before transfection cells were seeded in shake flask, and grown using serum-free chemically defined media. Variants 1-5 expression constructs (250 µg of each plasmid) were transiently transfected into 0.05 liter suspension CHO cells by electroporation. Briefly: 250×10$^6$ CHO cells were transfected using a Maxcyte Electroporator with 50% EP buffer and QC400 cuvette. Cells were grown using serum free media for seven days prior to harvest.

Figure 1:
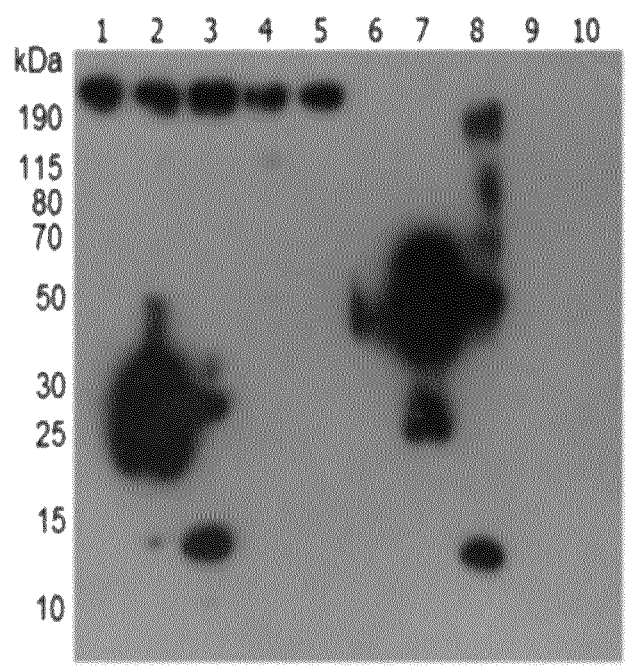
FIG. 1. Western-blot of the conditioned medium from Variants 1-5 under reducing and non-reducing conditions. Lanes 1 and 6: variant 5, respectively under reducing and non-reducing conditions; lanes 2 and 7: Variant 1, respectively under reducing and non-reducing conditions; lanes 3 and 8: Variant 2, respectively under reducing and non-reducing conditions; lanes 4 and 9: Variant 3, respectively under reducing and non-reducing conditions; lanes 5 and 10: Variant 2, respectively under reducing and non-reducing conditions. MW markers are on the left.

A Western blot performed at harvest demonstrated relative expression of PSGL-1 variants. Western blot analysis specific for the FLAG tag on conditioned media in non-reducing conditions confirmed protein dimerization. Variant 1 in the conditioned media showed under reducing conditions the expected molecular weight of ~22 kDa (FIG. 1, Lane 2). It correctly formed a dimer under non reducing conditions (FIG. 1, Lane 7). High molecular bands found in bands 1-5 are most likely molecules bound non-specifically to the anti-FLAG antibody (Anti-FLAG antibody, monoclonal mouse IgG1, Sigma-Aldrich, catalog #F1804).

In the case of lane 3 (Variant 2), the lower molecular weight bands might be a degradation product.

The western blot on the conditioned medium was carried out with an antibody which recognizes the Flag epitope placed at the C-terminus of all variants and is therefore indicative of the relative quantity of the different constructs of the chimeric protein secreted into the medium.

Purification of the FLAGGED Variants

Purification was carried out by ion exchange and anti-FLAG affinity purification. For each of the five variants, following clarification by 0.2 μM filtration the conditioned media was adjusted to pH 6 by the addition of 1 M HCl, and the volume was doubled with distilled water. The CM was then loaded onto a 1 mL anion exchange chromatography column (Q column, GE) and eluted in 20 mM Tris pH 7.5, 1 M HCl. The elution fraction was applied to 0.5 mL of anti-FLAG affinity M2 resin and rocked at room temperature for 5 hours. The resin was washed with 10 mL of Tris buffered saline. The protein was eluted with five column volumes of 100 μg/mL FLAG peptide in Tris buffered saline. For PSGL Variant 1, the flow-through was reincubated with anti-FLAG M2 resin overnight at 4° C., and elution was achieved using 0.25% acetic acid pH 3.5.

The Silver staining SDS-PAGE and $OD_{220}$ analysis of the purified PSGL Variants 1-5 suggests that Variant 1 has the highest purity and expression level among five constructs.

Protein concentration at $OD_{220}$, calculated by creating a standard curve with serial dilution of Bovine serum albumin and fitting the data from PSGL variants to that curve is given below in Table 3.

TABLE 3 recovery of protein Variants 1-5 after ion exchange and affinity purification

| | Variant 1 | Variant 2 | Variant 3 | Variant 4 | Variant 5 |
|---|---|---|---|---|---|
| Amount (mg) | 0.41 | 0.07 | 0.02 | 0.02 | 0.03 |

Among the five constructs, PSGL Variant 1 had the better yields: highest expression level and resulting purity by at least one log compared to the other Variants. Both western blot and silver staining SDS-PAGE under reducing and non-reducing conditions suggested that PSGL Variant 1 dimerized correctly.

Example 2: Expression and Purification of Variant 1A (without FLAG)

Stable CHO-S cells stable transformants, co-expressing the DNA sequence encoding the core 2 beta-1,6-N-acetyl-glucosaminyltransferase (C2GnT-M), the FTVII (fucosyltransferase VII) (Fugang Li et al. J. Biol. Chem, 1996, 271:3255-3264) and the chimeric protein encompassing aa 1-118 of SEQ ID NO:1 without FLAG sequence, was then produced according to the Freedom™ CHO-S™ Kit Manual (Cat. N A13696-01 Lifescience Thermofisher Scientific, July 2015).

CHO-S clones were allowed to grow for at least 7 days, usually up to 14 days, using OptiCHO™ medium (other serum-free chemically defined media were successfully used, e.g., ActiCHO™, CD FortiCHO™, and the likes) and in the absence of selection pressure. Glutamine (or the analogue GlutMax) was supplemented at 1-10 mM, preferably 4-8 mM.

100 mL of the supernatant from a pool of 6 stable CHO clones was collected, filtered on 0.2 μm PES membrane and loaded onto a strong anion exchange Capto Q column (GE 17-5316-02, 1.6×6 cm, 12 mL) previously equilibrated with 20 mM TRIS-HCl pH 7.5.

The bound proteins were eluted with a linear gradient of up to 1 M NaCl over 8 column volumes. The eluted fractions that contained the target protein, as shown by SDS-PAGE analysis were used for a second Phenyl hydrophobic interaction chromatography purification step.

The column was washed with 1 M NaOH, then equilibrated with and stored at 4° C. in 20% EtOH.

NaCl was dissolved in the pooled fractions to a concentration of 4 M. This pool was then loaded on 1 mL HIC column (HiTrap Phenyl HP™, GE Healthcare Life Sciences, Catalog #17-1351-01) previously equilibrated with 20 mM TRIS-HCl pH 7.5, 4 M NaCl, according to the manufacturer's instructions for a hydrophobic interaction chromatography. Elution was achieved by linearly decreasing the sodium chloride concentration to zero in 10 column volumes. Fractions containing the target protein as shown by SDS-PAGE analysis were pooled together for a third size exclusion chromatography (SEC) step. The SEC column (HiLoad 16/600 Superdex 200™ pg, GE Healthcare Life Sciences, Catalog #28-9893-35) was pre-equilibrated with 20 mM Tris-HCl pH 7.5, 150 mM NaCl, which was used as the mobile phase. Fractions containing the chimeric PSGL Variant 1 as shown by SDS-PAGE analysis were pooled and concentrated (Amicon Ultra Centrifugal Filter Unit, EMD Millipore).

As a more sensitive alternative to SDS-PAGE, Western Blot analysis was performed with Phast-System (GE) as described in the instruction manual. Nitrocellulose membrane was saturated with PBS+1% BSA (1 h at room temperature). The membrane was incubated 1 h at room temperature with PBS+0.5% Triton X-100+1% BSA containing an anti-P-Selectin Glycoprotein Ligand-1 antibody 1:1000 (anti-P-Selectin Glycoprotein Ligand-1 Antibody, clone KPL-1, EMD Millipore, cod. MAB4092).

After 3 washes with PBS+0.5% Triton X-100 the membrane was incubated with anti-mouse IgG-HRP as secondary antibody.

After 3 washings, the HRP signal was developed with ECL, showing positive anti-PSGL-1 antibody recognition.

The chimeric PSGL Variant 1A, from different subclones appeared as a single band at approximately 60 kDa, which shifted at about 30 kDa under reducing conditions, as expected. Neither additional bands nor degradation products were visible in Coomassie stained SDS-PAGE gels of purified product.

One clone was selected for further sub-cloning, medium scale growth and purification on a 2 L culture medium scale.

Example 3: Characterization of Purified Variant 1A

The PSGL Variant 1A recombinant protein, is highly heterogeneous due to different post-translational modifications, including sulfation and both N- and O-glycosylation. For its full characterization and correct quantification a set of analytical methods including UPLC, MS and peptide mapping procedures with specific enzymes was used. PSGL Variant 1A structural features, essential to its bioactivity, were also carefully monitored.

3.1. UPLC-UV

Reversed phase chromatography was used to determine the target protein content and to quantitate possible impurities or degradation products. For reverse phase chromatography experiments, an Acquity UPLC BEH300 column (2.1×100 mm, 1.7 µm) was used at 50° C. in gradient mode. The mobile phases were (A) 0.1% TFA in water and (B) 0.1% TFA in acetonitrile. UV detection was performed at 216 nm. The use of UPLC technology combined with a dedicated sub 2 m column allowed improved resolution, higher sensitivity, excellent peak shape and significant reduction in analysis times. The UPLC-UV method showed that the PSGL Variant 1A purity achieved by the purification process was higher than 90%.

3.2. SEC-UV

Size Exclusion Chromatography (SEC), also called Gel Permeation Chromatography (GPC), coupled to UV detection, which allows the separation of proteins on the basis of their effective size or shape (hydrodynamic radius), was used. In this case, the method was used to measure possible aggregates and other size Variants. For size exclusion chromatography experiments, TSK gel super SW mAb HTP 4.6×150 mm (Tosoh), 4 µm column was used at 30° C. in isocratic mode. The mobile phase was 50 mM $NaH_2PO_4$, 50 mM $Na_2HPO_4$, 100 mM $Na2SO_4$ and UV detection was performed at 216 nm. The use of UPLC instrumentation optimized to reduce extra-column band broadening allowed high column efficiency and increased sensitivity. The SEC-UV method was applied for the analysis of PSGL variant A-1: no aggregation was observed.

3.3. Sialic Acid Content

Sialylation is well known as a critical feature to biopharmaceutical products' bioavailability, stability, metabolism and immunogenicity. To this aim, a HPLC MS method was developed for the sialic acid determination of the chimeric protein Variant 1A.

The analysis was based on the combination of chemical hydrolysis method coupled with a derivatization-free liquid chromatography interfaced with electrospray ionization tandem mass spectrometry (LC-MS/MS). Sialic acid (N-Acetyl neuraminic acid NANA) was firstly released from PSGL Variant 1A by acid hydrolysis under mild acidic conditions. Once the sialic acid was released, its quantitation was carried out thanks to the use of LC-MS/MS method. The sialic acid amount was determined by comparing the response in the sample to a reference standard calibration curve. In experiments carried out with protein purified from other CHO subclones, sialylation was found to be typically comprised from 9.6 to 17.9% w/w.

3.4. MALDI-TOF-MS

Matrix Assisted Laser Desorption Ionization-Time Of Flight mass spectrometry (MALDI-TOF-MS), analyses were also performed to determine the PSGL Variant 1A molecular weight. This technique involves mixing the sample with a matrix, which is then coated onto a plate or probe, and subjected to a collimated focused laser beam, causing ionization and desorption. MALDI has the advantage of producing large mass ions, with high sensitivity and little fragmentation. MALDI-TOF experiments were performed on PSGL Variant 1A, under intact and reduced forms. As determined by MALDI experiments, the mean molecular weight of PSGL Variant 1A was measured at around 35.4 kDa. Reduction with DTT led to a 2-fold decrease of the PSGL Variant 1A mass, indicating the dimeric nature of the purified protein.

3.5. Peptide Mapping (Enzymatic Digestion)

Peptide mapping (PMAP) was used to elucidate the post-translational modifications (PTMs) of the chimeric glycoprotein, including sulfation and N- and O-glycosylation. To this aim, both Chymotrypsin and Asp-N were applied for protein digestion, followed by LC-MS Liquid Chromatography-Mass Spectrometry.

3.5.1. Fragmentation with Chymotrypsin

Chymotrypsin fragmentation was performed following the protocol provided by the manufacturer (Chymotrypsin Endoproteinase MS Grade, Cat. N. 90056, Thermo Scientific). One vial of dry chymotrypsin was reconstituted in 25 µL of HCl 0.1 M and stored at −18° C. before use as 2 µL aliquots in 500 µL eppendorf tubes. To prepare digestion buffer, consisting in 100 mM Tris-HCl pH (8, 10 mM $CaCl_2$, 3.03 g of Tris Base (M 121.4 g/mol) and 368 mg $CaCl_2$ (M 147.02 g/mol) were dissolved in water. The pH was adjusted to 8.0 using 1.2 M HCl and the volume was completed to 250 mL.

Fifty (50) µL of a PSGL-1 Variant 1A stock solution (0.5-1.0 mg/mL) were added to 2 µL of chymotrypsin and 48 µL of digestion buffer. The solution was incubated for 18 hours at 37° C. before injection in LC-MS.

3.5.2. Fragmentation with Endoproteinase Asp-N

Endoproteinase Asp-N fragmentation was performed following the protocol provided by the manufacturer (Asp N sequencing grade Roche, Cat. N. 11054589001). One vial of dry Asp-N was reconstituted in 50 µL of water and stored at −18° C. before use as 5 µL aliquots in 500 µL Eppendorf tubes. To prepare digestion buffer, consisting in 50 mM Sodium Phosphate, 1.5 g of $Na_2HPO_4$ (M 119.98 g/mol) was dissolved in water. The pH was adjusted to 8.0 using 1 M NaOH and the volume was completed to 250 mL.

Ten (10) µL of a PSGL-1 Variant 1A stock solution (0.5-1.0 mg/mL) were added to 5 µL of chymotrypsin and 35 µL of digestion buffer. The solution was incubated for 18 hours at 37° C. before injection in LC-MS.

Similar LC-MS analyses were used for the characterization of Asp-N and chymotrypsin digests. These experiments were performed using a Waters Acquity® UPLC system consisting of a temperature controlled sample manager, a binary solvent manager and a heated column compartment. The column outlet was connected directly to the mass spectrometer. The analytical column was a Poroshell® 120 EC-C18 2.1×150 mm i.d., particle size 2.7 µm from Agilent® at 40° C. The elution of the compounds from the column was carried out in the gradient mode using a mobile phase consisting of ultrapure water with 0.1% TFA and acetonitrile with 0.1% of TFA. The flow rate and injection volume were set at 0.3 mL/min and 10 µL, respectively. Detection was performed on a Waters Xevo TQ-S tandem quadrupole mass spectrometer equipped with electrospray ionization source in the positive and negative ionization mode according to compound. Nitrogen and argon were used as nebulizing and collision gases, respectively. Analyses were performed in the scan mode. Data acquisition and processing were performed with the help of MassLynx software package.

All the above assays allowed the following conclusions:
- the N-term structure of the PSGL-1 Variant 1A glycoprotein is dominated by the pyroglutamic form pQATEYEYL.
- the dimeric character of the PSGL Variant 1A was confirmed by the presence of $(M+2H)^{+2}=728.5$ attributed to the $(^{50}TCPPCPL^{56})_2$ sequence. Ions corresponding to the monomeric form of this peptide were not detected, suggesting that PSGL Variant 1A is entirely in the dimeric form.

the structure of the O-glycan residues on Thr$^{16}$ was confirmed: in fact, the expected Sialyl-Lewis-X motif, a Core 2 structure comprising N-Acetylgalactosamine, N-Acetylglucosamine, galactose, fucose and sialic acid was identified.

sulfation of Tyrosines 5, 7 and 10 was also demonstrated by mass spectrometry in the negative scan mode.

Most of the post-translation modifications (PTM) have been reported in SEQ ID NO:38.

Example 4: Affinity Binding on P-Selectin by Surface Plasmon Resonance (SPR)

The experiments were carried out with purified protein Fri as described in Example 2 of WO2012/020030 and Variant 1A as described in Example 2 above.

The binding strength of PSGL Variant 1A was evaluated by Surface Plasmon Resonance (SPR) using a Biacore X100 from GE Healthcare Bio-Sciences AB (General Electric, Piscataway, N.J.). The SPR technology allows monitoring the process of binding between biomolecules in real time and without labels. While P-selectin (target ligand) was attached to a sensor chip surface, the proteins of interest flowed in solution over the surface using a microfluidic system to ensure reproducible sample delivery and low sample consumption. SPR detects binding events as changes in mass at the chip surface. As a result, a sensogram is generated by plotting the SPR response against time.

Firstly, biotinylation of P-selectin/Fc (R&D Systems Europe Ltd) was performed in house. Then, immobilization of P-selectin/Fc on the working sensor (Fc2) of SA Chip (Streptavidin chip, GE Healthcare Bio-Sciences) was carried out as follows: One volume of the 10×HBS-N buffer (GE Healthcare Bio-Sciences AB) (50 mL) was diluted with 9 volumes of Milli-Q water (450 mL). Five hundred microliters of $CaCl_2$ 1.5 M (Fluka), pH about 5.6 were added to the diluted buffer (1.5 mM final) and filtered through 0.2 μm PES filter. The running buffer was prepared with 48.75 mL of HBS-N, $CaCl_2$ 1.5 mM buffer and 1.250 mL of surfactant P20 (GE Healthcare Bio-Sciences AB) in a 50 mL Falcon tube. HBS-N buffer and $CaCl_2$ 1.5 mM not immediately used were stored at +4° C.

Each sample to test was diluted in running buffer to achieve the indicated concentration of 125 nM. A manual run was started on the reference sensor (Fc1) and Fc2 with a flow rate of 30 μL/min. Reference subtraction 2-1 was selected. As soon as the base line was stable, analyte was injected for 30 sec. or longer if binding equilibrium was not reached. To directly compare binding of different analytes or different concentrations of the same analyte, it was necessary to program the same cycle parameters for each sample, for example:

Wait 120 sec.
Injection 30 sec.
Wait 300 sec.

When the manual run was finished, the Biacore X100 Evaluation software version 1.0 was opened, to create an overlay of each cycle.

Figure 2:
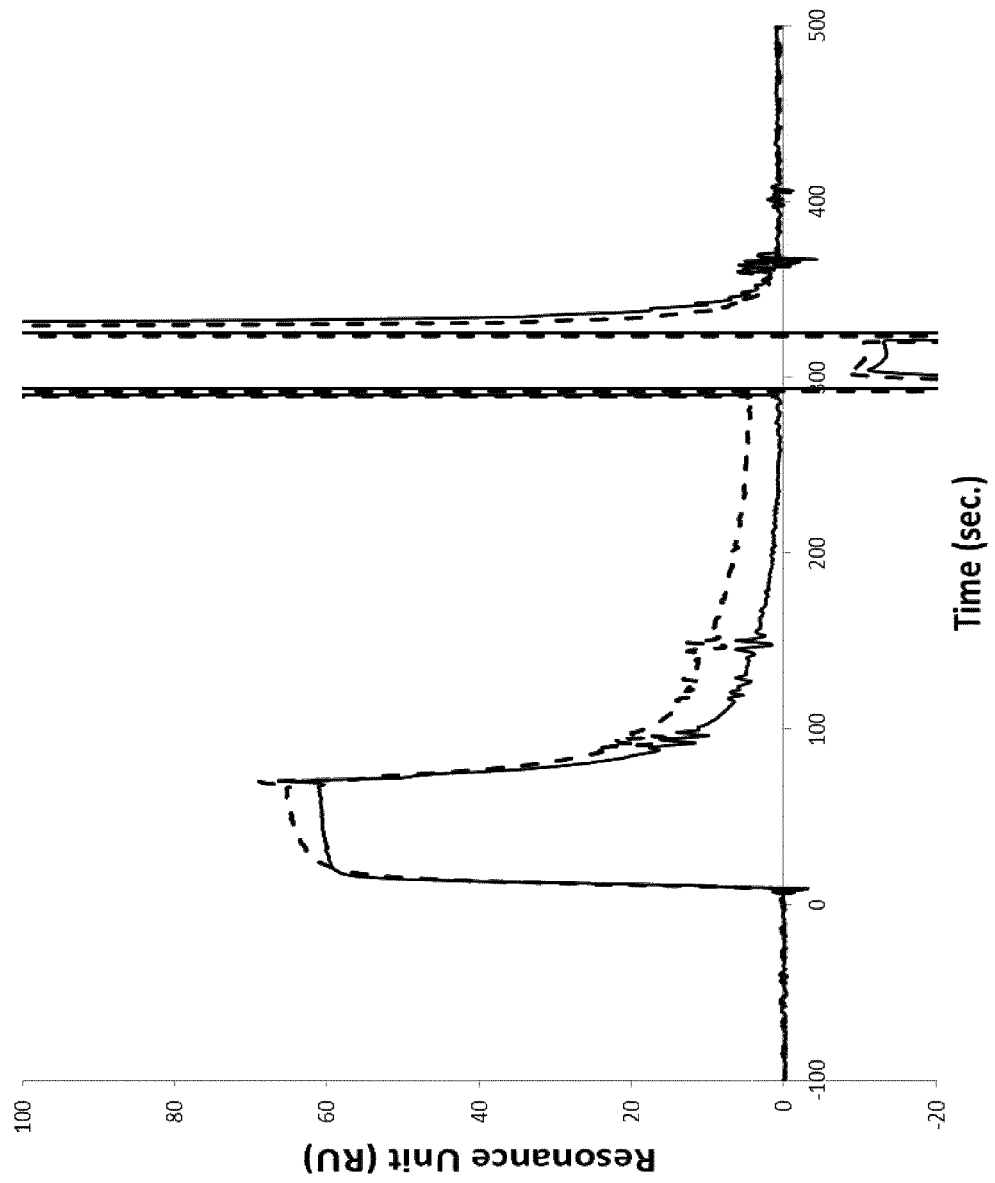
FIG. 2. SPR Biacore (protein binding response on P-selectin) comparison between Fragment 1 (Fr-1, solid line) and the chimeric protein of the invention (Variant 1A, hatched line) at 125 nM each. Y axis: Resonance Unit (RU) response including association/dissociation/regeneration as a function of time (secs) on the X axis.

Based on SPR experiments the binding affinity towards P-selectin was measured and the binding strength of the chimeric proteins to the target found to be equivalent or better than the Fri binding. FIG. 2 shows the result of the Biacore run, where the chimeric protein of the present invention (hatched line) showed an improved binding to the P-selectin ligand with respect to Fr.1.

SPR was also used for Variant 1A titration in the cell supernatant, according to the method described in Chou T-H. et al. Cytokine 51, 2010, 107-111. The sensor chip was overlayed with streptavidin and a mouse α-PSGL-1 antibody (KPL-1, Abcam, cat. N. ab78188) biotinylated at Bracco, used to quantitate Variant 1A in the supernatant.

Example 5: Preparation of Variant 1A-SMCC for Phospholipid Conjugation

The process was carried out according to example 9 of WO2012/020030.

Briefly, Variant 1 (65 nmoles) from example 2 was dissolved in 1 mL of Phosphate buffer 0.2 M pH 7.5 with 1 mM EDTA. A solution of Sulfo-SMCC (Sulfo-SMCC: sulfosuccinimidyl 4-[N-maleimidomethyl]cyclohexane-1-carboxylate) (Pierce) (55 mg/mL-125 mM) was prepared in anhydrous Dimethylsulfoxide (DMSO, Fluka) and 52 μL of the solution was added to the Variant 1 solution. The solution was incubated at room temperature for 45'. Then the solution was spun through a spin-column (Zeba spin-column 5 mL, Pierce #89890) equilibrated in phosphate buffer 20 mM pH 6. Isopropanol was added to the solution to obtain a solution containing 35% isopropanol.

Example 6: Preparation of the Conjugate DSPE-PEG-SH

DSPE-PEG2000-SH (DSPE: distearoyl phosphatidylethanolamine modified with PEG2000) was prepared from DSPE-PEG2000-PDP (1,2 Distearoyl-sn-glycero-3-phosphoethanolamine-N-[3-(2-pyridyldithio)propionate (polyethylene glycol)-2000]ammonium salt) according to example 10 of WO2012/020030. The final solution of DSPE-PEG2000-SH was diluted with Isopropanol to obtain a solution containing 35% Isopropanol.

Example 7: Preparation of DSPE-PEG-SH/Variant 1A-SMCC Conjugate 1.7 mL of Variant 1A-SMCC (65 nmoles) solution obtained in example 5 was added to a solution of DSPE-PEG2000-SH (325 nmoles-5 equivalents) obtained in example 6. The solution was incubated for three hours at room temperature with stirring (rotating wheel).

The solution was then purified by anion exchange chromatography with an ANX Sepharose gel (GE Healthcare). The solution containing the purified Variant 1 conjugate was spun through a spin column (Zeba spin column 10 mL, Pierce #89893) equilibrated in TRIS buffer 20 mM pH 7.5.

Example 8: Preparation of Microvesicles with the Conjugates of Example 7

10 mg of a mixture of DSPC (DSPC: Distearoylphosphatidylcholine) and Palmitic acid (80/20 molar ratio) were dissolved in cyclooctane (0.8 mL) at 70° C. Separately, the DSPE-PEG-SH/Variant 1-SMCC conjugate solution prepared according to example 7 (28 nmoles-1.3 mL) was added to 8.7 mL of PEG4000 10% solution in distilled water. A solution of DPPE-PEG5000 (DPPE: dipalmitoylphosphatidylethanolamine), (0.85 mg in 85 μL of water) was added to this aqueous phase.

The above prepared organic and aqueous solutions were admixed by using a high speed homogenizer (Polytron PT3000) to obtain an emulsion. The resulting emulsion was heated under stirring at 60° C. for one hour then cooled to room temperature (about 22° C.).

The obtained emulsion was diluted twice with a solution of PEG4000 10% in distilled water and sampled in DIN8R vials (0.5 mL emulsion/vial). Vials were frozen at −50° C. for 1 hour (Lyobeta 35 freeze dryer—TELSTAR), then freeze-dried at −20° C. and 0.2 mbar for 12 h. The lyophilized product was then exposed to an atmosphere of perfluoro-n-butane and nitrogen (35/65 v/v) mixture and the vials were sealed.

The product was dispersed in a volume of saline 150 mM (1 mL/vial) by gentle hand mixing.

Example 9: In Vitro Binding Activity of Targeted Microvesicles in a Flow-Chamber Setting To test the effective binding, targeted microvesicles prepared as described in WO2012/020030 (Example 6) and those prepared according to the present invention (example 8) were injected in a flow chamber set up comprising a coating of mouse Fc P-Selectin (catalog number 737-PS, R&D Systems, Minneapolis, Minn., USA) or human Fc P and E selectins (R&D catalog numbers 137-PS 50 and 724 ES 100) at 4 µg/mL. Microvesicles (at equivalent number of 80×10$^6$/400 µL TBS++) were injected through the flow chamber (FCS2, Bioptech, USA) in a bolus fashion and their adhesion onto the mouse P-selectin (or human P- or E-selectin) coating layer assessed over a period of 10 min at a flow rate of 1.0 mL/min (shear rate of 714 s$^{-1}$) in the presence of 50% (v:v) human plasma (Stehelin & Cie AG) in TBS. A quantitative analysis of microvesicles accumulation was performed by counting the number of microvesicles adhering in the observed area at 2 min intervals over the total 10 min infusion, using the image processing program Analysis FIVE (SIS, Germany). After 10 min, five pictures were taken randomly and the number of bound microvesicles was measured and expressed as the number of bound bubbles (NBB) at 10 min. Each observed area was 183×137 µm, as measured with the aid of a stage micrometer. Measurement was performed between the middle and the exit of the chamber.

Similarly, suspensions of targeted microvesicles prepared according to example 8 (Variant 1A as targeting ligand) was injected in a flow chamber as described above, and their binding activity determined according to the above procedure.

The experiment was repeated on coatings of human E-selectin and mouse P-selectin at the same concentration as above (4 µg/ml). The results are shown in Table 4.

TABLE 4

Number of Bound Microvesicles at 10 min (NBM 10 min)

| | NBM 10 min | | |
|---|---|---|---|
| Preparation | Mouse P selectin | Human E selectin | Human P selectin |
| microbubble Fr-1 | 74.30 ± 4.27 | 54.1 ± 7.23 | 77.0 ± 4.83 |
| microbubble Variant 1A | 73.60 ± 5.87 | 53.00 ± 4.37 | 65.40 ± 4.93 |

As inferable from the above results, the binding behavior of newly prepared MB-PSGL-1 Variant 1A is similar to microbubble carrying Fr 1: they display firm binding without aggregation in plasma and bind both human and mouse P-selectin as well as human E-selectin.

Example 10: In Vivo Experiments of Microvesicles with Fragment 1 (Comparative) and Variant 1A Microvesicles with Variant 1A prepared according to example 8 above and those carrying Fragment 1 (Fr-1) prepared according to WO2012/020030, example 6, were compared in an inflammatory rat model. Inflammation was induced in the rat hind limb by injection of lipopolysaccharide (LPS, 0.26:B6 Sigma L-8274, 2.1 mg/kg). The effective binding of the targeted microvesicles was evaluated by ultrasound contrast imaging 24 h after the induction of the inflammatory process. Contrast enhanced ultrasound imaging was performed using Logiq E9 ultrasound scanner (General Electric Healthcare, Fairfield, Conn., USA) equipped with the 9L linear transducer (transmit frequency, 4.0 MHz (Res); dynamic range, 48 dB; depth, 20 mm; Time-Gain Compensation (TGC), linear) operating in contrast mode. One image every second was recorded at low mechanical index (MI=0.06) during 30 s and then one image every 15 seconds up ten minutes. Ten minutes after single dose injection, contrast enhanced signal was acquired during 10 seconds at a frame rate of 4 Hz. Contrast enhanced images were recorded as Dicom files and analyzed using a dedicated software developed in-house (VueBox, Bracco Suisse SA, Geneva, Switzerland). This software allows a quantitative analysis of the echographic signal after linearization of the log compressed video sequences at the pixel level and provides contrast echo-power amplitude (expressed as arbitrary unit, A.U.) within an area of interest (AOI). The fixed bubble imaging (FBI) algorithm integrated in the software developed at Bracco (VueBox commercial kit) and helping to detect bound bubbles was applied on frames recorded at 10 minutes. The FBI processing relies on a minimum intensity projection function applied on a subset of images which is dependent on the window length (40 frames). The resulting images (FIG. 3) showed that microbubble carrying Variant 1A are able to visualize inflammation in the inflamed paw of rat and the signal observed is very similar to the one observed with microbubbles carrying Fr-1.

Example 11: Preparation of Fluorescent Liposomes with the Conjugates of Example 7

Cholesterol (28.25 mg—Merck #3672) was dissolved in 1 mL of chloroform. DSPE-PEG2000 (13.9 mg—Genzyme #LP-R4-039) was dissolved in 1 mL of chloroform. DiR (1,1'-Dioctadecyl-3,3,3',3'-Tetramethylindotricarbocyanine Iodide—Molecular Probes #D12731) was dissolved in ethanol to obtain a 10 mg/mL solution.

DSPC (79.7 mg-101 µmoles—Genzyme #LP-04-013) was weighed in a 100 mL-round balloon and dissolved in 30 mL of chloroform/methanol mixture (2/1 v/v). Samples of the cholesterol solution (575 µL-42 µmoles), of the DSPEPEG2000 solution (290 µL-1.5 µmole) and of the DiR solution (100 µL-1 µmole) were added to the DSPC solution. The obtained solution was stirred at 65° C. for 10 min and the solvents were removed under reduced pressure to obtain a lipid blend. This blend was dried at 65° C. under 20 mmHg then overnight at 25° C. under 0.2 mBar.

The dried lipid blend was redispersed in 10 mL of 20 mM Tris buffer (pH 7.4) at 70° C. under stirring (rotavapor) for 20 min. The obtained suspension was then extruded at 70° C. several times on Nuclepore filters (1×1 µm, 1×0.6 µm and 4×0.4 µm). This extrusion step could be adapted to obtain various liposome sizes. The liposomal suspension was then cooled to room temperature and stored at 4° C. in the dark.

The incorporation of the variant conjugate was carried out by a postinsertion procedure. Briefly, 500 µL of liposome suspension was mixed with 1 mL of Variant 1A conjugate solution prepared in example 7 (22 nmoles) at room temperature for 16 hours in the dark. The obtained liposome suspension was used without purification for in vivo experiments.

Fr-1 liposomes were obtained using the same procedure described above, replacing Variant 1A conjugates by Fr-1 conjugates (prepared as described in WO2012/020030, Example 6). The characteristics of the two liposome suspensions were compared in Table 6.

Size and Zeta potential of liposomes were determined using a Nanosizer ZetaZSP (Malvern instruments). The density of ligand per liposome was determined after liposomes washing (centrifugation 20000 g/30 min) by sialic acid determination (according example 3.3)

TABLE 5

Characteristics of control, Variant 1A and Fr-1 liposomes

| Liposomes | Size (nm) | Zeta potential (mV) | Ligand molecules/liposome |
|---|---|---|---|
| Without postinsertion | 268 | −6.4 | — |
| Variant 1A conjugate postinsertion | 278 | −39.1 | 780 |
| Fr-1 conjugate postinsertion | 291 | −34.7 | 700 |

Example 12. Optical Imaging Experiments Using Liposomes with Fragment 1 (Comparative) and Variant 1A in Mouse LPS Model Liposomes carrying Variant 1A were compared to liposomes with Fragment 1 in two groups of animals with hind limb inflammation. Inflammation was induced in the mouse hind limb by intramuscular injection of lipopolysaccharide (LPS, 0.26:B6 Sigma L-8274). Optical imaging was performed using the preclinical Fluobeam 700 system. The optical head was placed above the animal so that its hind limbs were placed in the center of the field of view of the camera (distance between mouse and camera 15 cm). Twenty-four hours after the induction of the inflammatory process, the targeted liposomes were injected and the fluorescent signal was followed over time (up to 24 h). The injection and the early phase were recorded as a sequence with one image every 5 seconds during 16 minutes (with fixed exposure time), followed by individual images at 20, 30, 45 min, 1, 2, and 4 hours. The images were analyzed using Image J software. In all the capture frames, same area of interest (AOI) was drawn to outline the inflamed and contralateral paws. The mean fluorescence intensity per millisecond was calculated in the AOI of each image. Fluorescent images are presented in FIG. 4 and quantification results expressed as ratio (Inflamed paw divided by contralateral paw) are presented in Table 7. Fluorescent images recorded 2 hours after Variant 1A-liposomes-DIR injection showed a higher signal in the inflamed paw compared to signal in the contralateral paw. In case of animal 3, the signal observed in the inflamed paw is low probably due to a low inflammation induced by LPS in this mouse. On the contrary, animal 6 presents a high signal indicative of a high inflammation. The calculated inflamed paw/contralateral paw ratio is higher for the Variant 1A compared to the Fragment-1 (Fr-1) indicative of a good specificity of the agent.

TABLE 6

Inflamed paw to contralateral paw Ratio in LPS inflammatory mouse model, 2h after injection of either Variant A1-liposomes-DIR or Fr-1-liposomes-DIR

| | Inflamed/contralateral paw ratio (2h) | | |
|---|---|---|---|
| Mouse N. | Variant 1A | Mouse N. | Fr-1 |
| 1 | 13.2 | 7 | 4.3 |
| 2 | 23.0 | 8 | 6.0 |
| 3 | 3.9 | 9 | 3.5 |
| 4 | 18.0 | 10 | 4.1 |
| 5 | 6.6 | 11 | 4.7 |
| 6 | 12.8 | 12 | 5.3 |
| Mean | 12.9 | | 4.7 |
| S.D. | 5.4 | | 7.9 |

Example 13. Optimization of the Purification Conditions by HA Chromatography (Negative or Positive)

Purification by AE/HI and HA (negative) 600 mL of Conditioned Medium was filtered on 0.22 μm membrane and loaded onto AEX column (Capto Q™, GE, 2.6×7 cm, 37 mL) equilibrated with 20 mM TRIS pH 7.5. The bound proteins were eluted with 2 step elution at 30% and 100% of 20 mM TRIS, 1 M NaCl, pH 7.5. The target protein was eluted in the 100% fraction. The column was cleaned with 1 M NaOH, and stored at 4° C. in 20%. EtOH.

Conductivity of the conditioned medium was below 10 mS/cm.

Solid NaCl was added to the pool from the 100% elution step of the AEX purification to a final concentration of 4 M. The sample was divided in two parts in order not to overload the column. Then it was loaded on a hydrophobic interaction chromatographic column (Phenyl Sepharose™, GE, 1.6×9 cm, 18 mL volume) previously equilibrated with 20 mM TRIS, 4 M NaCl, pH 7.5. The bound proteins were eluted with 2 steps at 50% and 100% of 20 mM TRIS pH 7.5. The target protein was eluted in the 50% fraction.

After the second run, the column was cleaned with 0.2 M NaOH and stored at 4° C. in 20% EtOH.

The pools from the first elution step in the two HIC runs were combined and the phosphate/$CaCl_2$ concentrations were adjusted to 10 and 0.3 mM, respectively, by addition of 500 mM phosphate pH 6.8 and 1 M $CaCl_2$. The pool was then diafiltered against 10 mM Phosphate, 0.3 mM $CaCl_2$, pH 6.8 in an Amicon™ ultrafiltration stirred cell (Merck, assembled with membrane YM10, with 10 kDa nominal molecular weight cut off). Then, the diafiltered pool was loaded onto a Hydroxyapatite column (BioRad, 2.2×5 cm, 19 mL volume) previously equilibrated with 10 mM Phosphate, 0.3 mM $CaCl_2$, pH 6.8. The PSGL Variant 1A was eluted in the FT fraction (negative chromatography).

The FT fraction was concentrated with Amicon™ Centrifugal Filter Unit, according to manufacturer's instructions. The purified protein was frozen at −40° C. The final concentration was 0.89 mg/mL for a total yield of 38.7 mg (73%) and a purity of 99.7% (FIG. 5).

Residual DNA and protein contaminants were measured after each chromatographic step, by a DNA quantitation assay (DNA Quantitation Kit, Fluorescence Assay, Sigma, detection limit 2 mg/L) and RP-HPLC (purity vs other proteins) respectively.

Values are summarized in the following table:

TABLE 7

Purity and residual DNA content after 3-steps chromatography

| Purification Step | PSGL Variant 1A Purity by RP-HPLC | Residual DNA content |
|---|---|---|
| Anion exchange (AE) | <58% | 97% |
| Hydrophobic Interaction (HI) | 72.6% | 2% |
| Hydroxyapatite (HA) | 99.3% | Below the detection limit |

Purification by AE/HI and HA (Positive)

1000 mL of Conditioned Medium was filtered on 0.22 μm membrane and loaded onto AE column (Capto Q™, GE, 2.6×7 cm, 37 mL) equilibrated with 20 mM TRIS pH 7.5. The bound proteins were eluted with 2 step elution at 30% and 100% of 20 mM TRIS, 1 M NaCl, pH 7.5. The target protein was eluted in the 100% fraction. The column was cleaned with 1 M NaOH, and stored at 4° C. in 20% EtOH.

Solid NaCl was added to the pool from the 100% elution step of the AE purification to a final concentration of 4 M. The sample was divided in two parts in order not to overload the column. Then it was loaded on a hydrophobic interaction chromatographic column (Phenyl Sepharose™, GE, 1.6×9 cm, 18 mL volume) previously equilibrated with 20 mM TRIS, 4 M NaCl, pH 7.5. The bound proteins were eluted with 2 steps at 50% and 100% of 20 mM TRIS pH 7.5. The target protein was eluted in the 50% fraction.

After the third run, the column was cleaned with 0.2 M NaOH and stored at 4° C. in 20% EtOH.

The pools from the first elution step of each HIC runs were combined and diluted 4-fold with water. Then, the diluted pool was loaded onto a Hydroxyapatite column (BioRad, 2.2×5 cm, 19 mL volume) previously equilibrated with 5 mM Phosphate, 1 mM $MgCl_2$, pH 6.8. The bound proteins were eluted with a gradient from 0-12.5% of 500 mM phosphate buffer. The PSGL Variant 1A was eluted as the first peak.

The fractions containing the target protein were concentrated with Amicon Centrifugal Filter Unit (Ultracel-10 membrane, 10 kDa MWCO), according to the manufacturer's instructions.

The purified protein was frozen at −40° C. The final concentration was 1.09 mg/mL for a total yield of 25 mg, corresponding to about 70% of the total target protein content and a purity of 98.7%.

The invention claimed is:

1. A dimeric protein comprising two recombinant chimeric P-Selectin Glycoprotein Ligand-1 (PSGL-1) proteins, wherein each recombinant chimeric PSGL-1 protein comprises at least: a selectin Binding domain comprising at least amino acids 5-16 of SEQ ID NO:11 (mature PSGL-1 sequence) and capable of specifically binding a selectin protein, a leucine zipper domain comprising an amino acid sequence at least 90% homologous or identical to amino acids 187-208 of SEQ ID NO:12 (Neural Retina-specific Leucine Zipper) and a disulfide bonds promoting region comprising at least one cysteine, such that the two recombinant chimeric PSGL-1 proteins are covalently linked to each other by at least a disulfide bond, and wherein the dimeric protein further comprises a poly-glycine spacer of SEQ ID NO:17.

2. The dimeric protein according to claim 1 wherein the selectin Binding domain comprises at least amino acids 1-47 of SEQ ID NO:11 (PSGL-1 sequence).

3. The dimeric protein according to claim 1 wherein said leucine Zipper comprises an amino acid sequence at least 90% homologous or identical to amino acids 181-215 of SEQ ID NO:12.

4. The dimeric protein according to claim 1 wherein said disulfide bonds promoting region comprises an amino acid sequence defined by the following general formula:

$(X_1)n\text{-}C(X_2)m\text{-}(X_3)$ wherein:
- $X_1$, $X_2$ represents any amino acid or amino acid sequence with the exclusion of cysteine (Cys),
- C is Cys
- $X_3$ is any amino acid and
- n, m are integer numbers comprised from 1-6.

5. The dimeric protein according to claim 4 wherein:
$X_1$ comprises a Proline, Histidine or Threonine;
n is at most 5 and
$X_2$ comprises at least one Proline.

6. The dimeric protein according to claim 5 wherein:
$X_2$ is Pro-Pro;
$X_3$ comprises a Cysteine and at least a Proline.

7. The dimeric protein according to claim 6 wherein said disulfide bonds promoting region is a IgG1 Hinge region (SEQ ID NO:20).

8. The dimeric protein according to claim 1 further comprising a signal peptide sequence suitable for secretion and for being cleaved off before secretion.

9. The dimeric protein according to claim 8 wherein said signal peptide is selected from the group consisting of: SEQ ID NO:18 and SEQ ID NOs: 21-34.

10. A pharmaceutical composition comprising the dimeric protein according to claim 1.

* * * * *